US011376320B2

(12) United States Patent
Cho

(10) Patent No.: US 11,376,320 B2
(45) Date of Patent: Jul. 5, 2022

(54) IMMUNOGENIC AND VACCINE COMPOSITIONS AGAINST SARS-COV-2

(71) Applicant: Iowa State University Research Foundation, Inc., Ames, IA (US)

(72) Inventor: Michael Wan Cho, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 17/249,546

(22) Filed: Mar. 4, 2021

(65) Prior Publication Data

US 2021/0275665 A1    Sep. 9, 2021

Related U.S. Application Data

(60) Provisional application No. 63/198,922, filed on Nov. 23, 2020, provisional application No. 62/989,404, filed on Mar. 13, 2020, provisional application No. 62/985,631, filed on Mar. 5, 2020.

(51) Int. Cl.
*A61K 39/215* (2006.01)
*C07K 14/165* (2006.01)
*A61K 39/00* (2006.01)

(52) U.S. Cl.
CPC .......... *A61K 39/215* (2013.01); *C07K 14/165* (2013.01); *A61K 2039/545* (2013.01)

(58) Field of Classification Search
None
See application file for complete search history.

(56) References Cited

U.S. PATENT DOCUMENTS

2018/0244756 A1 * 8/2018 Graham ................ C07K 14/005

FOREIGN PATENT DOCUMENTS

| CN | 111217917 A | * | 6/2020 |
| WO | 2015080973 A1 | | 6/2015 |
| WO | 2018094241 A1 | | 5/2018 |

OTHER PUBLICATIONS

Tian et al., Emerging Microbes & Infections, Feb. 2020, 9(1):382-385. (Year: 2020).*
Garton et al., PNAS Feb. 13, 2018 115 (7) 1505-1510. (Year: 2018).*
Walls et al., bioRxiv Preprint, posted Feb. 20, 2020, https://doi.org/10.1101/2020.02.19.956581. (Year: 2020).*
Liu et al., ThermoFisher Scientific Poster, No. date provided.*
Bisht et al., "Severe acute respiratory syndrome coronavirus spike protein expressed by attenuated vaccinia virus protectively immunizes mice", PNAS, vol. 101, No. 17, pp. 6641-6646, Apr. 27, 2004.
Callendret et al., "Heterologous virus RNA export elements improve expression of severe acute respiratory syndrome (SARS) coronavirus spike protein and protective efficacy of DNA vaccines against SARS", Virology, vol. 363, pp. 288-302, 2007.
Cao et al., "Potent and persistent antibody responses against the receptor-binding domain of SARS-CoV spike protein in recovered patients", Virology Journal, vol. 7, No. 299, pp. 1-6, 2010.
Chen et al., "Yeast-expressed recombinant protein of the receptor-binding domain in SARS-CoV spike protein with deglycosylated forms as a SARS vaccine candidate", Human Vaccines & Immunotherapeutics, vol. 10, No. 3, pp. 648-658, Mar. 2014.
Coughlin et al., "Neutralizing Human Monoclonal Antibodies to Severe Acute Respiratory Syndrome Coronavirus: Target, Mechanism of Action and Therapeutic Potential", Rev. Med. Virol., vol. 22, No. 1, pp. 2-17, doi:10.1002/rmv.706, Jan. 2012.
Du et al., "Antigenicity and immunogenicity of SARS-CoV S protein receptor-binding domain stably expressed in CHO cells", Biochem Biophys Res. Commun., vol. 384, No. 4, pp. 486-490, doi:10.1016/j.bbrc.2009.05.003, Jul. 10, 2009.
Du et al., "Receptor-binding domain of SARS-CoV spike protein induces long-term protective immunity in an animal model", Vaccine, vol. 25, pp. 2832-2838, 2007.
He et al., "Inactivated SARS-CoV vaccine elicits high titers of spike protein-specific antibodies that block receptor binding and virus entry", Biochemical and Biophysical Research Communications, vol. 325, pp. 445-452, 2004.
Huang et al., "Clinical features of patients infected with 2019 novel coronavirus in Wuhan, China", Articles, vol. 395, pp. 497-506, Feb. 15, 2020.
Hwang et al., "Structural Basis of Neutralization by a Human Anti-severe Acute Respiratory Syndrome Spike Protein Antibody, 80R*", Journal of Biological Chemistry, vol. 281, No. 45, downloaded from http://www.jbc.org/ at Iowa State University on Mar. 3, 2020, Nov. 10, 2006.
Lamirande et al., "A LIve Attenuated Severe Acute Respiratory Syndrome Coronavirus is Immunogenic and Efficacious in Golden Syrian Hamsters", Journal of Virology, vol. 82, No. 15, pp. 7721-7724, Aug. 2008.
Li et al., "Structure of SARS Coronavirus Spike Receptor-Binding Domain Complexed with Receptor", Science, vol. 309, downloaded from http://science.sciencemag.org/ on Mar. 3, 2020, Sep. 16, 2005.
Lin et al., "Safety and immunogenicity from a Phase I trial of inactivated severe acute respiratory syndrome coronavirus vaccine", Antiviral Therapy, vol. 12, pp. 1107-1113, 2007.
Martin et al., "A SARS DNA Vaccine Induces Neutralizing Antibody and Cellular Immune Reponses in Healthy Adults in a Phase I Clinical Trial", Vaccine, vol. 26, No. 50, pp. 6338-6343, doi:10.1016/j.vaccine.2008.09.026, Nov. 25, 2008.

(Continued)

*Primary Examiner* — Nicole Kinsey White
(74) *Attorney, Agent, or Firm* — McKee, Voorhees & Sease, PLC

(57) ABSTRACT

Disclosed herein are immunogenic and/or vaccine compositions and methods for treating or preventing Severe acute respiratory syndrome (SARS). The compositions and methods include an immunogenic portion of the receptor-binding domain (RBD) of the SARS-CoV-2-2 (COVID-19) spike protein. In at least particular cases, a mutated version of a portion of the RBD is utilized, such as a deglycosylated, or amino acid substituted mutant of the spike protein.

Figure 1A:
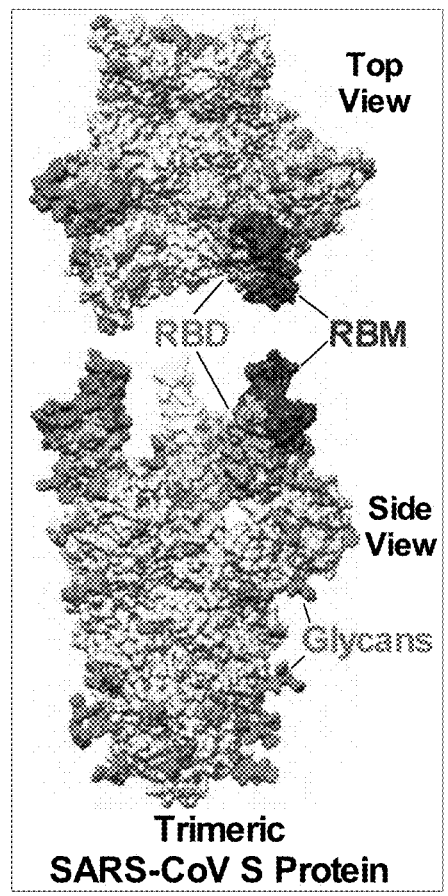

14 Claims, 35 Drawing Sheets
Specification includes a Sequence Listing.

(56) References Cited

OTHER PUBLICATIONS

Pak et al., "Structural Insights into Immune Recognition of the Severe Acute Respiratory Syndrome Coronavirus S Protein Receptor Binding Domain", J. Mol. Biol., vol. 388, pp. 815-823, doi:10.1016/j.jmb.2009.03.042, 2009.

Prabakaran et al., "Structure of Severe Acute Respiratory Syndrome Coronavirus Receptor-binding Domain Complexed with Neutralizing Antibody", The Journal of Biological Chemistry, vol. 281, No. 23, downloaded from http://www.jbc.org/ at Iowa State University on Mar. 3, 2020, Jun. 9, 2006.

Qu et al., "Intranasal immunization with inactivated SARS-CoV (SARS-associated coronavirus) induced local and serum antibodies in mice", Vaccine, vol. 23, pp. 924-931, 2005.

Quinlan et al., "The SARS-CoV-2 receptor-binding domain elicits a potent neutralizing response without antibody-dependent enhancement", https://doi.org/10.1101/2020.04.10.036418, Apr. 12, 2020.

Takasuka et al., "A subcutaneously injected UV-inactivated SARS coronavirus vaccine elicits systemic humoral immunity in mice", International Immunology, vol. 16, No. 10, pp. 1423-1430, doi:10.1093/intimm/dxh143, 2004.

Walls et al., "Unexpected receptor functional mimicry elucidates activation of coronavirus fusion", Cell, vol. 176, No. 5, pp. 1026-1039, doi:10.1016/j.cell.2018.12.028, Feb. 2019.

Xiong et al., "Immunogenicity of SARS inactivated vaccine in BALB/c mice", Immunology Letters, vol. 95, pp. 139-143, 2004.

Yang et al., "A DNA vaccine induces SARS coronavirus neutralization and protective immunity in mice", NATURE, vol. 428, pp. 561-564, Apr. 2004.

Yuan et al., "Cryo-EM structures of MERS-CoV and SARS-CoV spike glycoproteins reveal the dynamic receptor binding domains", Nature Communications, vol. 8, No. 15092, pp. 1-9, Apr. 10, 2017.

Zeng et al., "Characterization of humoral responses in mice immunized with plasmid DNAs encoding SARS-CoV spike gene fragments", Biochemical and Biophysical Research Communications, vol. 315, pp. 1134-1139, 2004.

Zhang et al., "Immune responses in Balb/c mice induced by a candidate SARS-CoV inactivated vaccine prepared from F69 strain", Vaccine, vol. 23, pp. 3196-3201, 2005.

Zhou et al., "A pneumonia outbreak associated with a new coronavirus of probable bat origin", Nature, https://doi.org/10.1038/s41586-020-2012-7, Jan. 2020.

Zhu et al., "Receptor-binding domain as a target for developing SARS vaccines", Journal of Thoracic Disease, vol. 5, Suppl. 2, pp. S142-S148, doi:l0.3978/j.issn.2072-1439.2013.06.06, Aug. 2013.

CD Creative Diagnostics Safety Data Sheet—"Recombinant 2019-nCoV Spike Protein Receptor Binding Domain [Fc]", 6 pages, Jan. 28, 2018.

CD Creative Diagnostics, "Recombinant SARS-CoV-2 Spike Protein Receptor Binding Domain [Fc] (DAGC089)", https://www.creative-diagnostics.com, 2 pages, Jan. 1, 2020.

International Searching Authority in connection with PCT/US2021/020826 filed Mar. 4, 2021, "International Search Report", 18 pages, dated Jul. 2, 2021.

Lan et al., "Structure of the SARS-CoV-2 spike receptor-binding domain bound to the ACE2 receptor", Nature, vol. 581, 16 pages, May 14, 2020.

Liu et al., "Enhanced elicitation of potent neutralizing antibodies by the SARS-CoV-2 spike receptor binding domain Fc fusion protein in mice", Vaccine, vol. 38, Issue 46, pp. 7205-7212, Oct. 27, 2020.

Gao et al., "Development of an inactivated vaccine candidate for SARS-CoV-2", Science, vol. 369, pp. 77-81, Jul. 3, 2020.

Shang et al., "Structural basis of receptor recognition by SARS-CoV-2", Nature, vol. 581, pp. 221-224, May 14, 2020.

Sun et al., "SARS-CoV-2 and SARS-CoV Spike-RBD Structure and Receptor Binding Comparison and Potential Implications on Neutralizing Antibody and Vaccine Development", https://doi.org/10.1101/2020.02.16.951723, pp. 1-18, Feb. 20, 2020.

Tai et al., "Characterization of the receptor-binding domain (RBD) of 2019 novel coronavirus: implication for development of RBD protein as a viral attachment inhibitor and vaccine", Cellular & Molecular Immunology, pp. 613-620, Mar. 19, 2020.

Walls et al., "Structure, Function, and Antigenicity of the SARS-CoV-2 Spike Glycoprotein", Cell, vol. 180, pp. 281-292, Apr. 16, 2020.

Yan et al., "Structural basis for the recognition of SARS-CoV-2 by full-length human ACE2", Science, vol. 367, pp. 1444-1448, Mar. 27, 2020.

Yang et al., "A vaccine targeting the RBD of the S protein of SARS-CoV-2 induces protective immunity", Nature, vol. 586, pp. 572-577, Oct. 22, 2020.

Zheng et al., "Novel antibody epitopes dominate the antigenicity of spike glycoprotein in SARS-CoV-2 compared to SARS-CoV", Cellular & Molecular Immunology, vol. 17, pp. 536-538, Mar. 4, 2020.

* cited by examiner

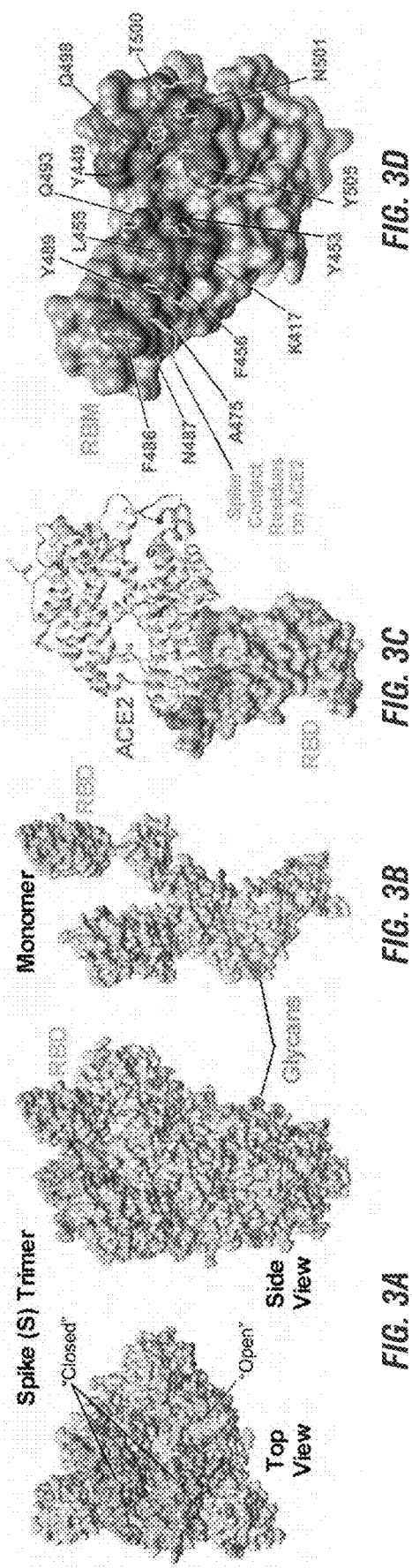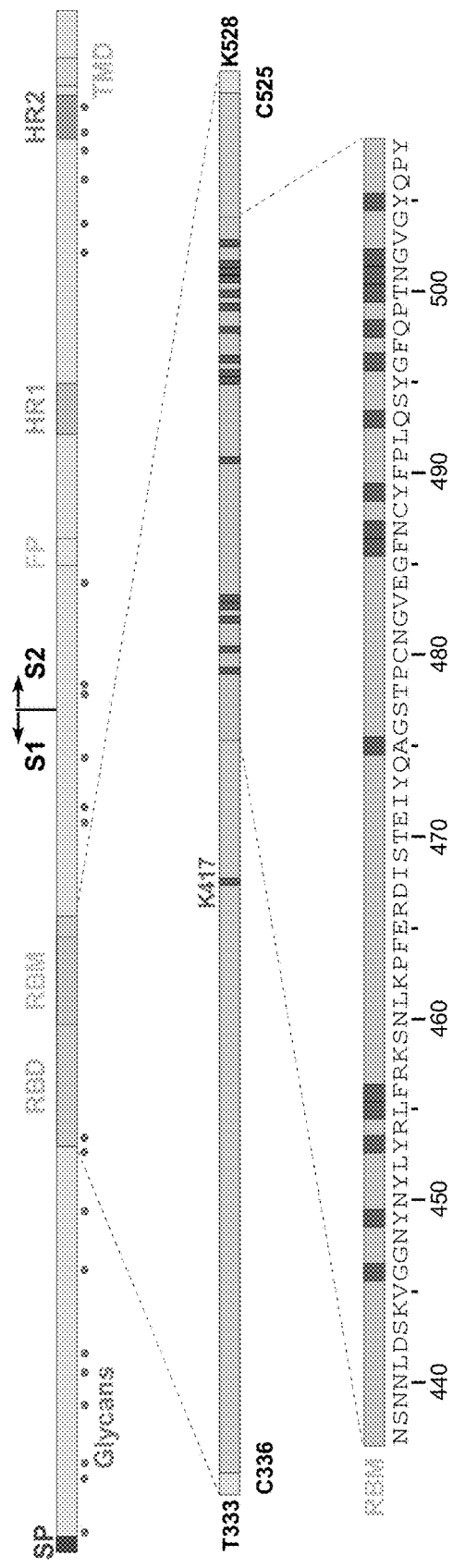

```
                EcoRI        NcoI
        5□  GAATTCGCCACCATGGGAATACTTCCTTCCCCTGGTATGCCTGCGCTTCTTTCACTCGTGTCCCT
         ▸••  ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼        65
        3□  CTTAAGCGGTGGTACCCTTATGAAGGAAGGGGACCATACGGACGCGAAGAAAGTGAGCACAGGGA
                         1        5         10           15
                         M  G  I  L  P  S  P  G  M  P  A  L  L  S  L  V  S  L
                         └─────────────────── Signal Peptide ─────────────────>

▓▓▓▓▓▓▓▓▓▓▓▓▓▓▓
                         Kozak sequence

M  G  I  L  P  S  P  G  M  P  A  L  L  S  L  V  S  L   ⇒
```

```
                                 HindIII      AgeI        Acc65I    KpnI
            TCTTAGCGTACTTCTCATGGGCTGCGTCGCCGAAAAGCTTACCGGTGGTACCACAAATCTCTGCC
            ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼           130
            AGAATCGCATGAAGAGTACCCGACGCAGCGGCTTTTCGAATGGCCACCATGGTGTTTAGAGACGG
                  20           25            1         5         1
             L  S  V  L  L  M  G  C  V  A  E  K  L  T  G  G  T  T  N  L  C
             ──── Signal Peptide ────>  ── N-term Linker ──>  ── SARS-CoV-2 RBD >

L  S  V  L  L  M  G  C  V  A  E  K  L  T  G  G  T  T  N  L  C   ⇒
```

```
                                                  AccI
            CATTTGGGGAAGTTTTCAATGCGACAAGATTCGCTAGTGTCTACGCATGGAACCGGAAACGAATC
            ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼           195
            GTAAACCCCTTCAAAAGTTACGCTGTTCTAAGCGATCACAGATGCGTACCTTGGCCTTTGCTTAG
              5          10          15          20          25
             P  F  G  E  V  F  N  A  T  R  F  A  S  V  Y  A  W  N  R  K  R  I
             ─────────────────── SARS-CoV-2 RBD ─────────────────────────>

P  F  G  E  V  F  N  A  T  R  F  A  S  V  Y  A  W  N  R  K  R  I   ⇒
```

```
            AGCAACTGCGTAGCGGATTACTCCGTCTTGTATAATTCCGCGTCATTCTCTACGTTCAAGTGCTA
            ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼           260
            TCGTTGACGCATCGCCTAATGAGGCAGAACATATTAAGGCGCAGTAAGAGATGCAAGTTCACGAT
                   30          35          40          45
             S  N  C  V  A  D  Y  S  V  L  Y  N  S  A  S  F  S  T  F  K  C  Y
             ─────────────────── SARS-CoV-2 RBD ─────────────────────────>

S  N  C  V  A  D  Y  S  V  L  Y  N  S  A  S  F  S  T  F  K  C  Y   ⇒
```

```
            TGGTGTATCCCCCACCAAACTCAACGACTTGTGCTTTACGAATGTCTATGCCGATTCATTCGTTA
            ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼           325
            ACCACATAGGGGGTGGTTTGAGTTGCTGAACACGAAATGCTTACAGATACGGCTAAGTAAGCAAT
                 50          55          60          65
             G  V  S  P  T  K  L  N  D  L  C  F  T  N  V  Y  A  D  S  F  V
             ─────────────────── SARS-CoV-2 RBD ─────────────────────────>

G  V  S  P  T  K  L  N  D  L  C  F  T  N  V  Y  A  D  S  F  V   ⇒
```

*FIG. 11A*

```
                      TACGCGGAGACGAGGTAAGACAAATAGCTCCAGGGCAGACCGGGAAAATTGCGGATTATAACTAC
                      ++++++++++++++++++++++++++++++++++++++++++++++++++++++++++++++++++    390
                      ATGCGCCTCTGCTCCATTCTGTTTATCGAGGTCCCGTCTGGCCCTTTTAACGCCTAATATTGATG
                      ....70........75........80........85........90....
                        I  R  G  D  E  V  R  Q  I  A  P  G  Q  T  G  K  I  A  D  Y  N  Y
                        ═══════════════════════ SARS-CoV-2 RBD ═══════════════════════>
                        I  R  G  D  E  V  R  Q  I  A  P  G  Q  T  G  K  I  A  D  Y  N  Y  ➡

AAACTGCCAGACGACTTTACTGGGTGTGTTATCGCCTGGAACAGTAACAATTTGGACTCCAAAGT
                      ++++++++++++++++++++++++++++++++++++++++++++++++++++++++++++++++++    455
                      TTTGACGGTCTGCTGAAATGACCCACACAATAGCGGACCTTGTCATTGTTAAACCTGAGGTTTCA
                      ......95........100.......105.......110....
                        K  L  P  D  D  F  T  G  C  V  I  A  W  N  S  N  N  L  D  S  K  V
                        ═══════════════════════ SARS-CoV-2 RBD ═══════════════════════>
                        K  L  P  D  D  F  T  G  C  V  I  A  W  N  S  N  N  L  D  S  K  V  ➡

CGGGGGTAACTATAATTACTTGTATAGACTGTTCCGCAAAAGCAATCTCAAACCCTTCGAGCGGG
                      ++++++++++++++++++++++++++++++++++++++++++++++++++++++++++++++++++    520
                      GCCCCCATTGATATTAATGAACATATCTGACAAGGCGTTTTCGTTAGAGTTTGGGAAGCTCGCCC
                      ......115.......120.......125.......130....
                        G  G  N  Y  N  Y  L  Y  R  L  F  R  K  S  N  L  K  P  F  E  R
                        ═══════════════════════ SARS-CoV-2 RBD ═══════════════════════>
                        G  G  N  Y  N  Y  L  Y  R  L  F  R  K  S  N  L  K  P  F  E  R  ➡

PflMI
                      ATATTTCCACCGAGATTTATCAGGCGGGGAGTACTCCATGCAATGGGGTTGAGGGATTTAACTGC
                      ++++++++++++++++++++++++++++++++++++++++++++++++++++++++++++++++++    585
                      TATAAAGGTGGCTCTAAATAGTCCGCCCCTCATGAGGTACGTTACCCCAACTCCCTAAATTGACG
                      ......135.......140.......145.......150.......155....
                        D  I  S  T  E  I  Y  Q  A  G  S  T  P  C  N  G  V  E  G  F  N  C
                        ═══════════════════════ SARS-CoV-2 RBD ═══════════════════════>
                        D  I  S  T  E  I  Y  Q  A  G  S  T  P  C  N  G  V  E  G  F  N  C  ➡

XcmI         EcoRV
                      TATTTTCCATTGCAATCTTACGGTTTCCAGCCTACGAATGGAGTCGGATATCAACCCTACAGGGT
                      ++++++++++++++++++++++++++++++++++++++++++++++++++++++++++++++++++    650
                      ATAAAAGGTAACGTTAGAATGCCAAAGGTCGGATGCTTACCTCAGCCTATAGTTGGGATGTCCCA
                      .......160.......165.......170.......175....
                        Y  F  P  L  Q  S  Y  G  F  Q  P  T  N  G  V  G  Y  Q  P  Y  R  V
                        ═══════════════════════ SARS-CoV-2 RBD ═══════════════════════>
                        Y  F  P  L  Q  S  Y  G  F  Q  P  T  N  G  V  G  Y  Q  P  Y  R  V  ➡
```

*FIG. 11B*

```
                  GCATTGGCGCAGAAAAAAATGCCTGATGCGACGCTGCGCGTCTTATACTCCCACATATGCCAGAT
                  ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖    1170
                  CGTAACCGCGTCTTTTTTTACGGACTACGCTGCGACGCGCAGAATATGAGGGTGTATACGGCTA
                  ┌────────────────────── rrnG terminator ──────────────────────────
                                                  M   R   R   C   A   S   Y   T   P   T   Y   A   R    ⟹

TCAGCAACGGATACGGCTTCCCCAACTTGCCCACTTCCATACGTGTCCTCCTTACCAGAAATTTA
                  ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖    1235
                  AGTCGTTGCCTATGCCGAAGGGGTTGAACGGGTGAAGGTATGCACAGGAGGAATGGTCTTTAAAT
                  ──────────────────────── rrnG terminator ──────────────────────────
                    F   S   N   G   Y   G   F   P   N   L   P   T   S   I   R   V   L   L   T   R   N   L    ⟹

SbfI
                  TCCTTAAGGTCGTCAGCTATCCTGCAGGCGATCTCTCGATTTCGATCAAGACATTCCTTTAATGG
                  ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖    1300
                  AGGAATTCCAGCAGTCGATAGGACGTCCGCTAGAGAGCTAAAGCTAGTTCTGTAAGGAAATTACC
                  ─────────┐                                            ┌── 3' β-globin insulator ──
                  rrnG terminator
                    S   L   R   S   S   A   I   L   Q   A   I   S   R   F   R   S   R   H   S   F   N   G    ⟹

TCTTTTCTGGACACCACTAGGGGTCAGAAGTAGTTCATCAAACTTTCTTCCCTCCCTAATCTCAT
                  ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖    1365
                  AGAAAAGACCTGTGGTGATCCCCAGTCTTCATCAAGTAGTTTGAAAGAAGGGAGGGATTAGAGTA
                  ──────────────────── 3' β-globin insulator ─────────────────────
                    L   F   W   T   P   L   G   V   R   S   S   S   S   N   F   L   P   S   L   I   S    ⟹

PacI
                  TGGTTACCTTGGGCTATCGAAACTTAATTAACCAGTCAAGTCAGCTACTTGGCGAGATCGACTTG
                  ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖    1430
                  ACCAATGGAACCCGATAGCTTTGAATTAATTGGTCAGTTCAGTCGATGAACCGCTCTAGCTGAAC
                    L   V   T   L   G   Y   R   N   L   I   N   Q   S   S   Q   L   L   G   E   I   D   L    ⟹

TCTGGGTTTCGACTACGCTCAGAATTGCGTCAGTCAAGTTCGATCTGGTCCTTGCTATTGCACCC
                  ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖    1495
                  AGACCCAAAGCTGATGCGAGTCTTAACGCAGTCAGTTCAAGCTAGACCAGGAACGATAACGTGGG
                    S   G   F   R   L   R   S   E   L   R   Q   S   S   S   S   I   W   S   L   L   L   H   P    ⟹

GTTCTCCGATTACGAGTTTCATTTAAATCATGTGAGCAAAAGGCCAGCAAAAGGCCAGGAACCGT
                  ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖    1560
                  CAAGAGGCTAATGCTCAAAGTAAATTTAGTACACTCGTTTTCCGGTCGTTTTCCGGTCCTTGGCA
                    F   S   D   Y   E   F   H   L   N   H   V   S   K   R   P   A   K   G   Q   E   P    ⟹

AAAAGGCCGCGTTGCTGGCGTTTTTCCATAGGCTCCGCCCCCCTGACGAGCATCACAAAAATCG
                  ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖    1625
                  TTTTCCGGCGCAACGACCGCAAAAAGGTATCCGAGGCGGGGGGACTGCTCGTAGTGTTTTTAGC
                                                               ⟵──────── ori ──────────
                  ▪                                                                              ⟹
```

*FIG. 11D*

```
ACGCTCAAGTCAGAGGTGGCGAAACCCGACAGGACTATAAAGATACCAGGCGTTTCCCCCTGGAA
                                                                    1690
TGCGAGTTCAGTCTCCACCGCTTTGGGCTGTCCTGATATTTCTATGGTCCGCAAAGGGGGACCTT
                                ori GCTCCCTCGTGCGCTCTCCTGTTCCGACCCTGCCGCTTACCGGATACCTGTCCGCCTTTCTCCCT
                                                                    1755
CGAGGGAGCACGCGAGAGGACAAGGCTGGGACGGCGAATGGCCTATGGACAGGCGGAAAGAGGGA
                                ori TCGGGAAGCGTGGCGCTTTCTCATAGCTCACGCTGTAGGTATCTCAGTTCGGTGTAGGTCGTTCG
                                                                    1820
AGCCCTTCGCACCGCGAAAGAGTATCGAGTGCGACATCCATAGAGTCAAGCCACATCCAGCAAGC
                                ori CTCCAAGCTGGGCTGTGTGCACGAACCCCCGTTCAGCCCGACCGCTGCGCCTTATCCGGTAACT
                                                                    1885
GAGGTTCGACCCGACACACGTGCTTGGGGGGCAAGTCGGGCTGGCGACGCGGAATAGGCCATTGA
                                ori ATCGTCTTGAGTCCAACCCGGTAAGACACGACTTATCGCCACTGGCAGCAGCCACTGGTAACAGG
                                                                    1950
TAGCAGAACTCAGGTTGGGCCATTCTGTGCTGAATAGCGGTGACCGTCGTCGGTGACCATTGTCC
                                ori ATTAGCAGAGCGAGGTATGTAGGCGGTGCTACAGAGTTCTTGAAGTGGTGGCCTAACTACGGCTA
                                                                    2015
TAATCGTCTCGCTCCATACATCCGCCACGATGTCTCAAGAACTTCACCACCGGATTGATGCCGAT
                                ori CACTAGAAGAACAGTATTTGGTATCTGCGCTCTGCTGAAGCCAGTTACCTTCGGAAAAAGAGTTG
                                                                    2080
GTGATCTTCTTGTCATAAACCATAGACGCGAGACGACTTCGGTCAATGGAAGCCTTTTTCTCAAC
                                ori GTAGCTCTTGATCCGGCAAACAAACCACCGCTGGTAGCGGTGGTTTTTTGTTTGCAAGCAGCAG
                                                                    2145
CATCGAGAACTAGGCCGTTTGTTTGGTGGCGACCATCGCCACCAAAAAACAAACGTTCGTCGTC
                                ori ATTACGCGCAGAAAAAAGGATCTCAAGAAGATCCTTTGATCTTTTCTACGGGGTCTGACGCTCA
                                                                    2210
TAATGCGCGTCTTTTTTCCTAGAGTTCTTCTAGGAAACTAGAAAAGATGCCCCAGACTGCGAGT
                 ori BspHI
GTGGAACGAAAACTCACGTTAAGGGATTTTGGTCATGAGATTATCAAAAGGATCTTCACCTAGA
                                                                    2275
CACCTTGCTTTTGAGTGCAATTCCCTAAAACCAGTACTCTAATAGTTTTCCTAGAAGTGGATCT
```

*FIG. 11E*

```
TCCTTTTAAATTAAAAATGAAGTTTTAAATCAATCTAAAGTATATATGAGTAAACTTGGTCTGAC
                                                                                2340
AGGAAAATTTAATTTTTACTTCAAAATTTAGTTAGATTTCATATATACTCATTTGAACCAGACTG

AGTTACCAATGCTTAATCAGTGAGGCACCTATCTCAGCGATCTGTCTATTTCGTTCATCCATAGT
                                                                                2405
TCAATGGTTACGAATTAGTCACTCCGTGGATAGAGTCGCTAGACAGATAAAGCAAGTAGGTATCA

TGCATTTAAATTTCCGAACTCTCCAAGGCCCTCGTCGGAAAATCTTCAAACCTTTCGTCCGATCC
                                                                                2470
ACGTAAATTTAAAGGCTTGAGAGGTTCCGGGAGCAGCCTTTTAGAAGTTTGGAAAGCAGGCTAGG

NaeI    FseI
                              NgoMIV
ATCTTGCAGGCTACCTCTCGAACGAACTATCGCAAGTCTCTTGGCCGGCCTTGCGCCTTGGCTAT
                                                                                2535
TAGAACGTCCGATGGAGAGCTTGCTTGATAGCGTTCAGAGAACCGGCCGGAACGCGGAACCGATA

TGCTTGGCAGCGCCTATCGCCAGGTATTACTCCAATCCCGAATATCCGAGATCGGGATCACCCGA
                                                                                2600
ACGAACCGTCGCGGATAGCGGTCCATAATGAGGTTAGGGCTTATAGGCTCTAGCCCTAGTGGGCT

GAGAAGTTCAACCTACATCCTCAATCCCGATCTATCCGAGATCCGAGGAATATCGAAATCGGGGC
                                                                                2665
CTCTTCAAGTTGGATGTAGGAGTTAGGGCTACATAGGCTCTAGGCTCCTTATAGCTTTAGCCCCG

SacII                                AfeI
GCGCCTGGCCTCCGCGCCGGGTTTTGGCGCCTCCCGCGGGCGCCCCCTCGTCACGGCGAGCGCT
                                                                                2730
CGCGGACCGGAGGCGCGGCCCAAAACCGCGGAGGGCGCCCGCGGGGGAGCAGTGCCGCTCGCGA
        └─────────────────────── UbC promoter ───────────────────────>

Bpu10I
GCCACGTCAGACGAAGGGCGCAGGAGCGTCCTGATCCTTCCGCCCGGACGCTCAGGACAGCGGCC
                                                                                2795
CGGTGCAGTCTGCTTCCCGCGTCCTCGCAGGACTAGGAAGGCGGGCCTGCGAGTCCTGTCGCCGG
        ─────────────────────── UbC promoter ───────────────────────>

CGCTGCTCATAAGACTCGGCCTTAGAACCCCAGTATCAGCAGAAGGACATTTTAGGACGGGACTT
                                                                                2860
GCGACGAGTATTCTGAGCCGGAATCTTGGGGTCATAGTCGTCTTCCTGTAAAATCCTGCCCTGAA
        ─────────────────────── UbC promoter ───────────────────────>

GGGTGACTCTAGGGCACTGGTTTTCTTTCCAGAGAGCGGAACAGGCGAGGAAAAGTAGTCCCTTC
                                                                                2925
CCCACTGAGATCCCGTGACCAAAAGAAAGGTCTCTCGCCTTGTCCGCTCCTTTTCATCAGGGAAG
        ─────────────────────── UbC promoter ───────────────────────>
<──       P   V   P   K   R   E   L   S   R   F   L   R   P   F   T   T   G   E
```

*FIG. 11F*

*FIG. 11G*

```
                  AGGTCTTGAGCCCTTCGCTAATGCGGGAAAGCTCTTATTCGGGTGAGATGGGCTGGGCACCATCT
                  ++++++++++++++++++++++++++++++++++++++++++++++++++++++++++++++++++  3380
                  TCCAGAACTCGGGAAGCGATTACGCCCTTTCGAGAATAAGCCCACTCTACCCGACCCGTGGTAGA
                                            UbC promoter                                  >
                                   M  R  E  S  S  Y  S  G  E  M  G  W  A  P  S         →
         ⇐  P  R  S  G  K  A  L  A  P  F  S  K  N  P  H  S  P  S  P  V  M GGGGACCCTGACGTGAAGTTTGTCACTGACTGGAGAACTCGGTTTGTCGTCTGTTGCGGGGCGG
                  ++++++++++++++++++++++++++++++++++++++++++++++++++++++++++++++++++  3445
                  CCCCTGGGACTGCACTTCAAACAGTGACTGACCTCTTGAGCCAAACAGCAGACAACGCCCCGCC
                                            UbC promoter                                  >
            G  D  P  D  V  K  F  V  T  D  W  R  T  R  F  V  V  C  C  G  G             →

CAGTTATGGCGGTGCCGTTGGGCAGTGCACCCGTACCTTTGGGAGCGCGCGCCCTCGTCGTGTCG
                  ++++++++++++++++++++++++++++++++++++++++++++++++++++++++++++++++++  3510
                  GTCAATACCGCCACGGCAACCCGTCACGTGGGCATGGAAACCCTCGCGCGCGGGAGCAGCACAGC
                                            UbC promoter                                  >
            S  Y  G  G  A  V  G  Q  C  T  R  T  F  G  S  A  R  P  R  R  V             →

AarI
                  TGACGTCACCCGTTCTGTTGGCTTATAATGCAGGGTGGGGCCACCTGCCGGTAGGTGTGCGGTAG
                  ++++++++++++++++++++++++++++++++++++++++++++++++++++++++++++++++++  3575
                  ACTGCAGTGGGCAAGACAACCGAATATTACGTCCCACCCCGGTGGACGGCCATCCACACGCCATC
                                            UbC promoter                                  >
            V  T  S  P  V  L  L  A  Y  N  A  G  W  G  H  L  P  V  G  V  R  *          →

AvrII        EcoNI
                  GCTTTTCTCCGTCGCAGGACGCAGGGTTCGGGCCTAGGGTAGGCTCTCCTGAATCGACAGGCGCC
                  ++++++++++++++++++++++++++++++++++++++++++++++++++++++++++++++++++  3640
                  CGAAAAGAGGCAGCGTCCTGCGTCCCAAGCCCGGATCCCATCCGAGAGGACTTAGCTGTCCGCGG
                                            UbC promoter                                  >

GGACCTCTGGTGAGGGGAGGGATAAGTGAGGCGTCAGTTTCTTTGGTCGGTTTTATGTACCTATC
                  ++++++++++++++++++++++++++++++++++++++++++++++++++++++++++++++++++  3705
                  CCTGGAGACCACTCCCCTCCCTATTCACTCCGCAGTCAAAGAAACCAGCCAAAATACATGGATAG
                                            UbC promoter                                  >

TTCTTAAGTAGCTGAAGCTCCGGTTTTGAACTATGCGCTCGGGGTTGGCGAGTGTGTTTTGTGAA
                  ++++++++++++++++++++++++++++++++++++++++++++++++++++++++++++++++++  3770
                  AAGAATTCATCGACTTCGAGGCCAAAACTTGATACGCGAGCCCCAACCGCTCACACAAAACACTT
                                            UbC promoter                                  >

GTTTTTAGGCACCTTTTGAAATGTAATCATTTGGGTCAATATGTAATTTTCAGTGTTAGACTTG
                  ++++++++++++++++++++++++++++++++++++++++++++++++++++++++++++++++++  3835
                  CAAAAAATCCGTGGAAAACTTTACATTAGTAAACCCAGTTATACATTAAAGTCACAATCTGAAC
                                            UbC promoter                                  >
```

*FIG. 11H*

FIG. 11I

```
               TCCCGCCGTGCACAGGGTGTCACGTTGCAAGACCTGCCTGAAACCGAACTGCCCGCTGTTCTGCA
               ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  4225
               AGGGCGGCACGTGTCCCACAGTGCAACGTTCTGGACGGACTTTGGCTTGACGGGCGACAAGACGT
                       95          100         105         110
                  S  R  R  A  Q  G  V  T  L  Q  D  L  P  E  T  E  L  P  A  V  L  Q
                                                   HygR                                    >
                  S  R  R  A  Q  G  V  T  L  Q  D  L  P  E  T  E  L  P  A  V  L  Q     ➡
       ⬅          G  A  T  C  L  T  D  R  Q  L  V  Q  R  F  G  F  Q  G  S  N  Q  L

GCCGGTCGCGGAGGCAATGGATGCCATCGCTGCCGCCGATCTTAGCCAGACGAGCGGGTTCGGCC
               ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  4290
               CGGCCAGCGCCTCCGTTACCTACGGTAGCGACGGCGGCTAGAATCGGTCTGCTCGCCCAAGCCGG
                       115         120         125         130         135
                  P  V  A  E  A  M  D  A  I  A  A  A  D  L  S  Q  T  S  G  F  G
                                                   HygR                                    >
                  P  V  A  E  A  M  D  A  I  A  A  A  D  L  S  Q  T  S  G  F  G     ➡
       ⬅          R  D  R  L  C  H  I  G  D  S  G  G  I  K  A  L  R  A  P  E  A

RsrII
               CATTCGGACCGCAAGGAATCGGTCAATACACTACATGGCGTGATTTCATATGCGCGATTGCTGAT
               ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  4355
               GTAAGCCTGGCGTTCCTTAGCCAGTTATGTGATGTACCGCACTAAAGTATACGCGCTAACGACTA
                       140         145         150         155
                  P  F  G  P  Q  G  I  G  Q  Y  T  T  W  R  D  F  I  C  A  I  A  D
                                                   HygR                                    >
                  P  F  G  P  Q  G  I  G  Q  Y  T  T  W  R  D  F  I  C  A  I  A  D    ➡
       ⬅          W  E  S  R  L  S  D  T  L  V  S  C  P  T  I  E  Y  A  R  N  S  I

CCCCATGTGTATCACTGGCAAACTGTGATGGACGACACCGTCAGTGCGTCCGTCGCGCAGGCTCT
               ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  4420
               GGGGTACACATAGTGACCGTTTGACACTACCTGCTGTGGCAGTCACGCAGGCAGCGCGTCCGAGA
                       160         165         170         175
                  P  H  V  Y  H  W  Q  T  V  M  D  D  T  V  S  A  S  V  A  Q  A  L
                                                   HygR                                    >
                  P  H  V  Y  H  W  Q  T  V  M  D  D  T  V  S  A  S  V  A  Q  A  L    ➡
       ⬅          G  M  H  I  V  P  L  S  H  H  V  V  G  D  T  R  G  D  R  L  S  E

CGATGAGCTGATGCTTTGGGCCGAGGACTGCCCCGAAGTCCGGCACCTCGTGCACGCGGATTTCG
               ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  4485
               GCTACTCGACTACGAAACCCGGCTCCTGACGGGGCTTCAGGCCGTGGAGCACGTGCGCCTAAAGC
                       180         185         190         195         200
                  D  E  L  M  L  W  A  E  D  C  P  E  V  R  H  L  V  H  A  D  F
                                                   HygR                                    >
                  D  E  L  M  L  W  A  E  D  C  P  E  V  R  H  L  V  H  A  D  F    ➡
       ⬅          I  L  Q  H  K  P  G  L  V  A  G  F  D  P  V  E  H  V  R  I  E
```

*FIG. 11J*

FIG. 11K

```
ATCTCAACAGCGGTAAGATCCTTGAGAGTTTTCGCCCCGAAGAACGCTTTCCAATGATGAGCACT
                                                                              5460
TAGAGTTGTCGCCATTCTAGGAACTCTCAAAAGCGGGGCTTCTTGCGAAAGGTTACTACTCGTGA
         50           55           60           65
 D  L  N  S  G  K  I  L  E  S  F  R  P  E  E  R  F  P  M  M  S  T
                              AmpR
 D  L  N  S  G  K  I  L  E  S  F  R  P  E  E  R  F  P  M  M  S  T  →

TTTAAAGTTCTGCTATGTGGCGCGGTATTATCCCGTATTGACGCCGGGCAAGAGCAACTCGGTCG
                                                                              5525
AAATTTCAAGACGATACACCGCGCCATAATAGGGCATAACTGCGGCCCGTTCTCGTTGAGCCAGC
      70           75           80           85           90
 F  K  V  L  L  C  G  A  V  L  S  R  I  D  A  G  Q  E  Q  L  G  R
                              AmpR
 F  K  V  L  L  C  G  A  V  L  S  R  I  D  A  G  Q  E  Q  L  G  R  →

CCGCATACACTATTCTCAGAATGACTTGGTTGAGTATTCACCAGTCACAGAAAAGCATCTTACGG
                                                                              5590
GGCGTATGTGATAAGAGTCTTACTGAACCAACTCATAAGTGGTCAGTGTCTTTTCGTAGAATGCC
          95          100          105          110
 R  I  H  Y  S  Q  N  D  L  V  E  Y  S  P  V  T  E  K  H  L  T
                              AmpR
 R  I  H  Y  S  Q  N  D  L  V  E  Y  S  P  V  T  E  K  H  L  T  →

ATGGCATGACAGTAAGAGAATTATGCAGTGCTGCCATAACCATGAGTGATAACACTGCGGCCAAC
                                                                              5655
TACCGTACTGTCATTCTCTTAATACGTCACGACGGTATTGGTACTCACTATTGTGACGCCGGTTG
       115          120          125          130
 D  G  M  T  V  R  E  L  C  S  A  A  I  T  M  S  D  N  T  A  A  N
                              AmpR
 D  G  M  T  V  R  E  L  C  S  A  A  I  T  M  S  D  N  T  A  A  N  →

TTACTTCTGACAACGATTGGAGGACCGAAGGAGCTAACCGCTTTTTTGCACAACATGGGGGATCA
                                                                              5720
AATGAAGACTGTTGCTAACCTCCTGGCTTCCTCGATTGGCGAAAAAACGTGTTGTACCCCCTAGT
    135          140          145          150          155
 L  L  L  T  T  I  G  G  P  K  E  L  T  A  F  L  H  N  M  G  D  H
                              AmpR
 L  L  L  T  T  I  G  G  P  K  E  L  T  A  F  L  H  N  M  G  D  H  →
←
```

*FIG. 11M*

FIG. 11N

```
CAGGCAACTATGGATGAACGAAATAGACAGATCGCTGAGATAGGTGCCTCACTGATTAAGCATTG
++++++++++++++++++++++++++++++++++++++++++++++++++++++++++++++++   6110
GTCCGTTGATACCTACTTGCTTTATCTGTCTAGCGACTCTATCCACGGAGTGACTAATTCGTAAC
   265          270          275          280          285
    Q  A  T  M  D  E  R  N  R  Q  I  A  E  I  G  A  S  L  I  K  H  W
                              AmpR
    Q  A  T  M  D  E  R  N  R  Q  I  A  E  I  G  A  S  L  I  K  H  W

GTAACCGATTCTAGGTGCATTGGCGCAGAAAAAAATGCCTGATGCGACGCTGCGCGTCTTATACT
++++++++++++++++++++++++++++++++++++++++++++++++++++++++++++++++   6175
CATTGGCTAAGATCCACGTAACCGCGTCTTTTTTTACGGACTACGCTGCGACGCGCAGAATATGA

>                           rrnG terminator
 AmpR

M  R  R  C  A  S  Y  T

CCCACATATGCCAGATTCAGCAACGGATACGGCTTCCCCAACTTGCCCACTTCCATACGTGTCCT
++++++++++++++++++++++++++++++++++++++++++++++++++++++++++++++++   6240
GGGTGTATACGGTCTAAGTCGTTGCCTATGCCGAAGGGGTTGAACGGGTGAAGGTATGCACAGGA
                              rrnG terminator
  P  T  Y  A  R  F  S  N  G  Y  G  F  P  N  L  P  T  S  I  R  V  L CCTTACCAGAAATTTATCCTTAAGATCGTTTAAACTCGACTCTGGCTCTATCGAATCTCCGTCGT
++++++++++++++++++++++++++++++++++++++++++++++++++++++++++++++++   6305
GGAATGGTCTTTAAATAGGAATTCTAGCAAATTTGAGCTGAGACCGAGATAGCTTAGAGGCAGCA
       rrnG terminator
  L  T  R  N  L  S  L  R  S  F  K  L  D  S  G  S  I  E  S  P  S TTCGAGCTTACGCGAACAGCCGTGGCGCTCATTTGCTCGTCGGGCATCGAATCTCGTCAGCTATC
++++++++++++++++++++++++++++++++++++++++++++++++++++++++++++++++   6370
AAGCTCGAATGCGCTTGTCGGCACCGCGAGTAAACGAGCAGCCCGTAGCTTAGAGCAGTCGATAG

F  R  A  Y  A  N  S  R  G  A  H  L  L  V  G  H  R  I  S  S  A  I

PvuI
               AsiSI
GTCAGCTTACCTTTTTGGCAGCGATCGCGGCTCCCGACATCTTGGACCATTAGCTCCACAGGTAT
++++++++++++++++++++++++++++++++++++++++++++++++++++++++++++++++   6435
CAGTCGAATGGAAAAACCGTCGCTAGCGCCGAGGGCTGTAGAACCTGGTAATCGAGGTGTCCATA
                                         5' β-globin insulator
  V  S  L  P  F  W  Q  R  S  R  L  P  T  S  W  T  I  S  S  T  G  I CTTCTTCCCTCTAGTGGTCATAACAGCAGCTTCAGCTACCTCTCAATTCAAAAAACCCCTCAAGA
++++++++++++++++++++++++++++++++++++++++++++++++++++++++++++++++   6500
GAAGAAGGGAGATCACCAGTATTGTCGTCGAAGTCGATGGAGAGTTAAGTTTTTTGGGGAGTTCT
             5' β-globin insulator                  T7 terminator
  F  F  P  L  V  V  I  T  A  A  S  A  T  S  Q  F  K  K  P  L  K
```

*FIG. 110*

```
CCCGTTTAGAGGCCCCAAGGGGTTATGCTATCAATCGTTGCGTTACACACACAAAAAACCAACAC
                                                                                6565
GGGCAAATCTCCGGGGTTCCCCAATACGATAGTTAGCAACGCAATGTGTGTTTTTTGGTTGTG
     [T7 terminator]                                  [poly(A) signal]
 T  R  L  E  A  P  R  G  Y  A  I  N  R  C  V  T  H  T  K  N  Q  H →

ACATCCATCTTCGATGGATAGCGATTTTATTATCTAACTGCTGATCGAGTGTAGCCAGATCAGT
                                                                                6630
TGTAGGTAGAAGCTACCTATCGCTAAAATAATAGATTGACGACTAGCTCACATCGGTCTAGATCA
     [poly(A) signal]
 T  S  I  F  D  G  SS                                                         →

AATCAATTACGGGGTCATTAGTTCATAGCCCATATATGGAGTTCCGCGTTACATAACTTACGGTA
                                                                                6695
TTAGTTAATGCCCCAGTAATCAAGTATCGGGTATATACCTCAAGGCGCAATGTATTGAATGCCAT
                                                           [CMV enhancer]

AATGGCCCGCCTGGCTGACCGCCCAACGACCCCCGCCCATTGACGTCAATAATGACGTATGTTCC
                                                                                6760
TTACCGGGCGGACCGACTGGCGGGTTGCTGGGGGCGGGTAACTGCAGTTATTACTGCATACAAGG
                       [CMV enhancer]

CATAGTAACGCCAATAGGGACTTTCCATTGACGTCAATGGGTGGAGTATTTACGGTAAACTGCCC
                                                                                6825
GTATCATTGCGGTTATCCCTGAAAGGTAACTGCAGTTACCCACCTCATAAATGCCATTTGACGGG
                       [CMV enhancer]

ACTTGGCAGTACATCAAGTGTATCATATGCCAAGTACGCCCCCTATTGACGTCAATGACGGTAAA
                                                                                6890
TGAACCGTCATGTAGTTCACATAGTATACGGTTCATGCGGGGATAACTGCAGTTACTGCCATTT
                       [CMV enhancer]

TGGCCCGCCTGGCATTATGCCCAGTACATGACCTTATGGGACTTTCCTACTTGGCAGTACATCTA
                                                                                6955
ACCGGGCGGACCGTAATACGGGTCATGTACTGGAATACCCTGAAAGGATGAACCGTCATGTAGAT
                       [CMV enhancer]

SnaBI
CGTATTAGTCATCGCTATTACCATGCTGATGCGGTTTTGGCAGTACATCAATGGGCGTGGATAGC
                                                                                7020
GCATAATCAGTAGCGATAATGGTACGACTACGCCAAAACCGTCATGTAGTTACCCGCACCTATCG
      [CMV enhancer]                   [CMV promoter]                          >

GGTTTGACTCACGGGGATTTCCAAGTCTCCACCCCATTGACGTCAATGGGAGTTTGTTTTGGCAC
                                                                                7085
CCAAACTGAGTGCCCCTAAAGGTTCAGAGGTGGGGTAACTGCAGTTACCCTCAAACAAAACCGTG
                       [CMV promoter]                                          >
```

*FIG. 11P*

```
CAAAATCAACGGGACTTTCCAAAATGTCGTAACAACTCCGCCCCATTGACGCAAATGGGCGGTAG
++++++|++++++|++++++|++++++|++++++|++++++|++++++|++++++|++++++|++++++|  7150
GTTTTAGTTGCCCTGAAAGGTTTTACAGCATTGTTGAGGCGGGGTAACTGCGTTTACCCGCCATC
                         CMV promoter                                  >

GCGTGTACGGTGGGAGGTCTATATAAGCAGAGCTGGTTTAGTGAACCGTCAGATCAGATCTTTGT
++++++|++++++|++++++|++++++|++++++|++++++|++++++|++++++|++++++|++++++|  7215
CGCACATGCCACCCTCCAGATATATTCGTCTCGACCAAATCACTTGGCAGTCTAGTCTAGAAACA
         CMV promoter         >
```

```
                                         NotI
                                         EagI
CGATCCTACCATCCACTCGACACACCCGCCAGCGGCCGC    30
++++++|++++++|++++++|++++++|++++++|+++++  ...  7254
GCTAGGATGGTAGGTGAGCTGTGTGGGCGGTCGCCGGCG    50
```

FIG. 11Q

IMMUNOGENIC AND VACCINE COMPOSITIONS AGAINST SARS-COV-2

CROSS REFERENCE TO RELATED APPLICATIONS

This application claims priority to provisional applications U.S. Ser. No. 62/985,631 filed Mar. 5, 2020, U.S. Ser. No. 62/989,404 filed Mar. 13, 2020, and U.S. Ser. No. 63/198,922 filed Nov. 23, 2020, which are incorporated herein by reference in their entireties.

SEQUENCE LISTING

The instant application contains a Sequence Listing which has been submitted in ASCII format by electronic submission and is hereby incorporated by reference in its entirety. Said ASCII copy, created on Mar. 2, 2021, is named 2021-03-02_CHO_P13196US03_SEQLISTING_ST25.txt and is 59,200 bytes in size.

FIELD OF THE INVENTION

This invention relates generally to novel immunogenic compositions that protect humans from disease caused by Severe Acute Respiratory Syndrome Coronavirus-2 (SARS-CoV-2).

BACKGROUND OF THE INVENTION

In December 2019, an outbreak of severe pneumonia (referred to as COVID-19) began in Wuhan, in the Hubei Province of China. The causative pathogen was identified as a novel coronavirus (CoV) designated as SARS-CoV-2 (a.k.a. 2019-nCoV). Early symptoms are similar to those of flu (e.g. fever, cough and sore throat). SARS-CoV-2 caused clusters of fatal pneumonia with clinical presentation greatly resembling 2002-03 epidemic of SARS-CoV, which includes persistent fever, chills/rigor, myalgia, malaise, dry cough, headache and dyspnoea. The virus is believed to have emerged through zoonosis from a Huanan seafood market that also sells various wild animals. The virus is transmitted efficiently from human to human, even prior to onset of symptoms, via droplets from coughing or sneezing, or direct contact. Consequently, the virus has been able to spread rapidly. Cases have been reported in over 115 countries beyond China and World Health Organization (WHO) has officially declared pandemic. The epidemiologic picture has been changing on a daily basis and it is expected to have a significant negative impact on global economy and public health system. Although the mortality rate is lower than that of SARS-CoV, SARS-CoV-2 has shown to be deadlier because of its high transmissibility. Development of a potent vaccine, antiviral drugs and/or immunotherapeutic agents is urgently needed.

The present disclosure provides a solution to this latest threat by providing a SARS immunogenic composition that can be used to develop a vaccine or to treat or prevent SARS-CoV-2 in animals.

BRIEF SUMMARY

As disclosed herein, a subunit protein vaccine candidate based on the receptor binding domain (RBD) of Spike (S) glycoprotein of SARS-CoV-2 was successfully designed, constructed, produced and purified. It is expected that its potential to induce neutralizing antibodies against SARS-CoV-2 and protective efficacy of these neutralizing antibodies is very high.

Embodiments of the disclosure concern methods and/or compositions related to COronaVIrus Disease-19 (COVID-19) preferably SARS-CoV-2, treatment or prevention, including complete prevention or reduction in severity of one or more symptoms or delay in onset of one or more symptoms of SARS-CoV-2, for example. In particular aspects, there are methods and/or compositions related to the SARS-CoV-2 spike protein useful for treatment or prevention of SARS. In certain embodiments, the receptor-binding domain (RBD) of the SARS-CoV-2 spike protein is related to COVID-19 treatment or prevention. In specific embodiments, there are methods and/or compositions concerning one or more modified RBDs of the SARS-CoV-2 spike protein for treatment or prevention of COVID-19. In some cases, modified RBD compositions may have amino acid substitutions, deletions, inversion, and so forth. In particular embodiments, the modified RBD composition has a modification at a glycosylation site. Some embodiments include RBDs that are modified to include deletion of an amino acid that is glycosylated under normal conditions. In specific embodiments, the composition is isolated, recombinant, synthetic, and/or not found in nature and may be operatively linked to heterologous sequences such as targeting sequences, promoters, spacers and the like.

In specific embodiments, one or more immunogenic compositions and/or methods are employed in an individual for the prevention of COVID-19 or delay in onset of COVID-19 and/or reduction of severity of at least one symptom of COVID-19.

Embodiments of the disclosure include development of a COVID-19 immunogenic composition, such as a vaccine, comprising a receptor-binding domain of the SARS-CoV-2 spike protein. The vaccine or immunogenic composition may comprise one or more adjuvants. In particular cases, the vaccine or immunogenic composition may be expressed as recombinant protein in yeast, insect cells, bacteria or in a mammalian system, for example.

In embodiments of the invention, yeast-expressed recombinant protein of the receptor-binding domain in SARS-CoV-2 spike protein with deglycosylation is useful as a SARS immunogenic composition or vaccine.

In particular aspects of the invention, the infection being addressed by methods and/or compositions of the disclosure is infection by a SARS- or SARS-related virus, such as a genetically related virus for Middle East Respiratory Syndrome (MERS). In some cases, the infection is a coronavirus that may or may not be SARS.

In specific embodiments, one or more immunogenic compositions and/or methods of the disclosure are employed in an individual for the treatment or prevention of MERS or delay in onset of MERS and/or reduction of severity of at least one symptom of MERS.

In some cases, an individual is of any age who is possibly exposed to SARS or a SARS-related infection or a SARS or SARS-related bioweapon, including a child, an elderly person, a member of the military, or a health care worker, for example. The individual may be in or may have been present in a geographical area known to have individuals with COVID-19 or prone to having individuals with COVID-19.

In embodiments of the disclosure, there is an isolated composition comprising the receptor-binding domain (RBD) of the Severe acute respiratory syndrome coronavirus (SARS-CoV-2) protein. In some cases, the domain is comprised within the full-length SARS-CoV-2 spike protein, whereas in other cases, the domain is a fragment of the SARS-CoV-2 spike protein.

Figure 9A:
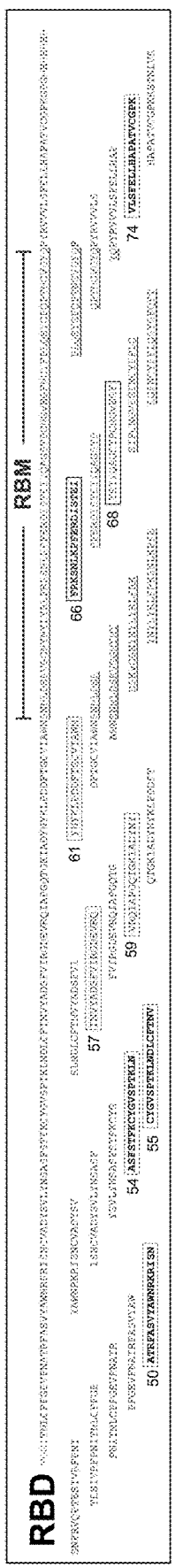
Figure 9B:
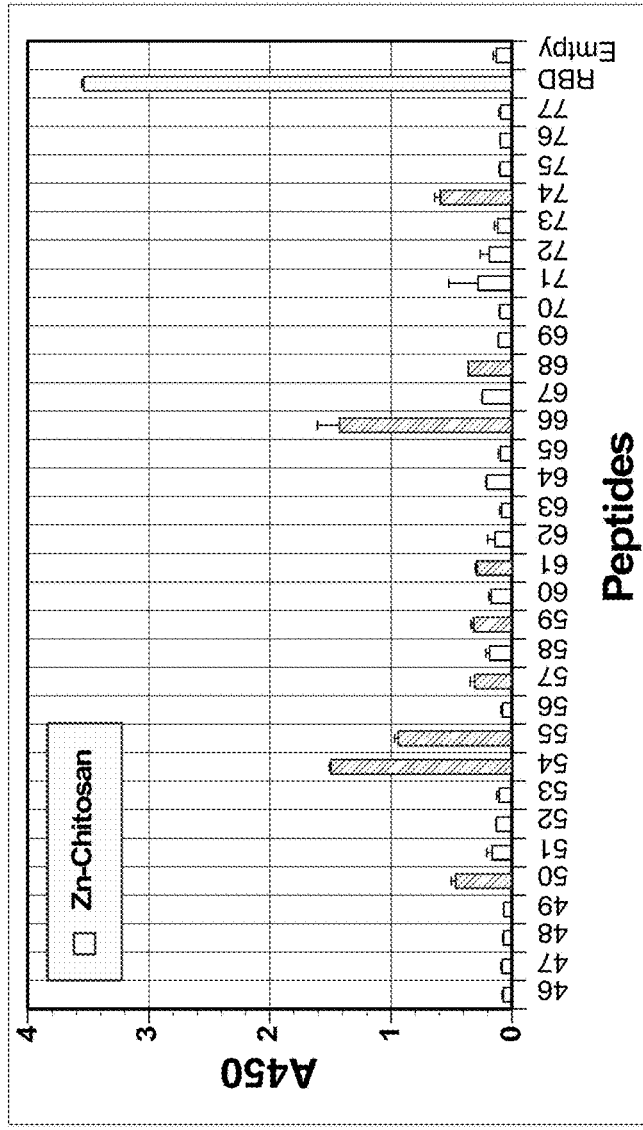
Figure 9C:
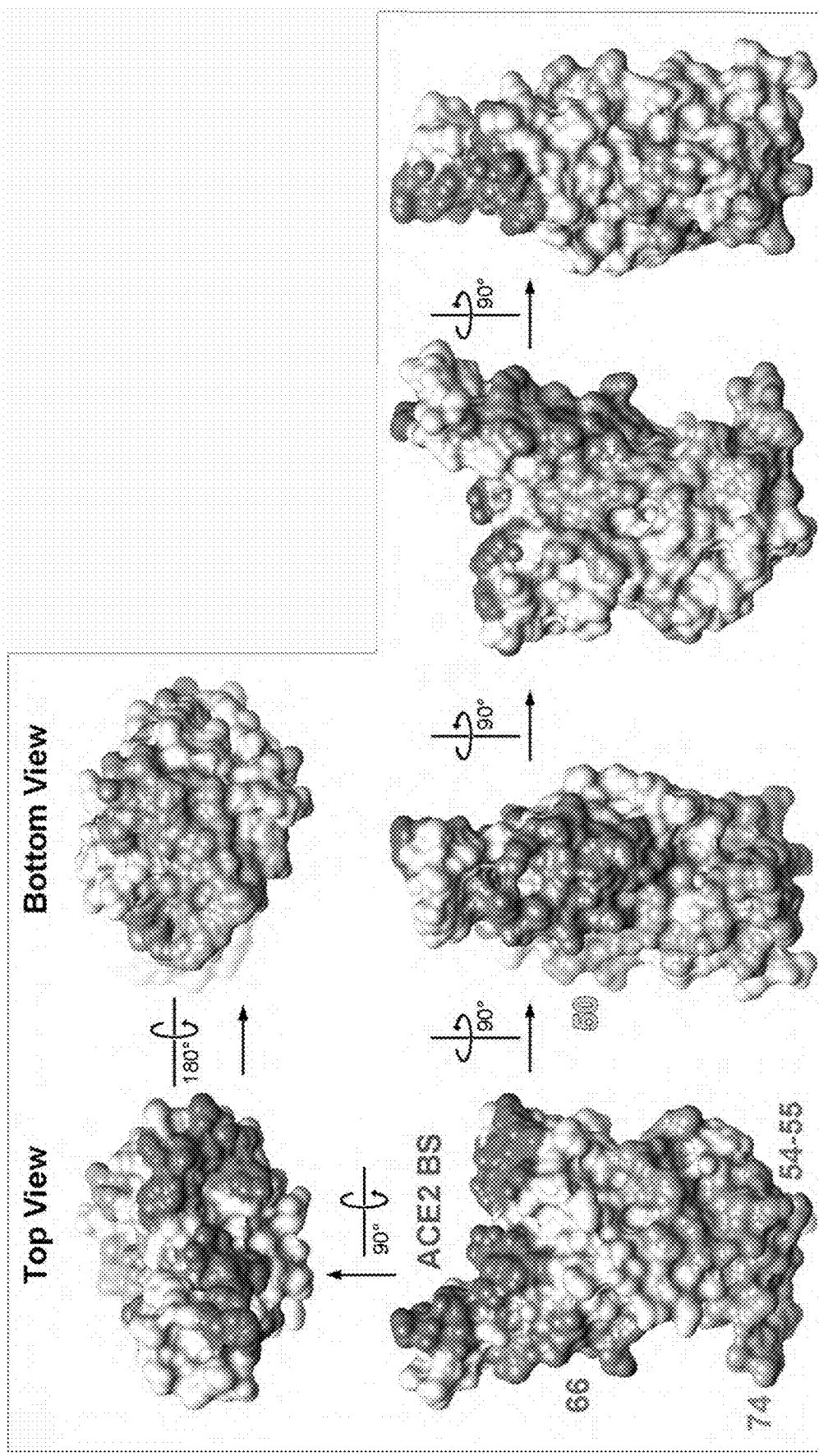

Any composition of the disclosure may be comprised in a pharmaceutically acceptable vehicle.

In one embodiment, there is a method of preventing or delaying the onset of COVID-19 or of reducing at least one symptom of COVID-19 in an individual, comprising the step of providing an effective amount of any of the compositions of the disclosure to the individual. In particular aspects, a composition is provided to the individual once or more than once. The composition may be provided subsequently to the individual within weeks, months, or years of the first providing step. In some cases, an individual displays one or more symptoms of COVID-19, lacks any symptoms of COVID-19, or has been exposed to COVID-19. In certain aspects, the individual has come into contact with an individual that has COVID-19. In particular facets, the individual is a child, an elderly person, exposed to a bioweapon or at risk thereof, or is a health care worker.

In one embodiment, there is a method of preventing or delaying the onset of MERS or of reducing at least one symptom of MERS in an individual, comprising the step of providing an effective amount of any of the compositions of the disclosure to the individual. In particular aspects, a composition is provided to the individual once or more than once. The composition may be provided subsequently to the individual within weeks, months, or years of the first providing step. In some cases, an individual displays one or more symptoms of MERS, lacks any symptoms of MERS, or has been exposed to MERS. In certain aspects, the individual has come into contact with an individual that has MERS. In particular facets, the individual is a child, an elderly person, exposed to a bioweapon or at risk thereof, or is a health care worker.

While multiple embodiments are disclosed, still other embodiments of the present invention will become apparent to those skilled in the art from the following detailed description, which shows and describes illustrative embodiments of the invention. Accordingly, the figures and detailed description are to be regarded as illustrative in nature and not restrictive.

DESCRIPTION OF THE FIGURES

FIG. 1A-B show structural features of SARS-CoV spike (S) glycoprotein. FIG. 1A shows a cryo-EM structure of trimeric S protein (PDB: 6NB7). Critical features are indicated. FIG. 1B shows co-crystal structures of SARS-CoV RBD with ACE2 (PDB: 2AJF) or nAb 80R (PDB: 2GHW). 80R, which efficiently neutralizes SARS-CoV binds directly on the RBM where ACE2 binds.

FIG. 2 shows purification of SARS-CoV-2 RBD. RBD was expressed in 293F cells transfected with a plasmid that encodes the protein. Culture supernatant was harvested on day 5 and the protein was purified using Ni-NTA, which binds to 6×His tag at the C-terminal end of the protein. U: unbound. W: wash fraction. E1-3: elution fractions.

FIG. 3A-G show structural features of SARS-CoV-2 S protein and RBD immunogen. FIG. 3A shows a cryo-EM structure of a trimer (PDB: 6VSB). Top and side views are shown, and the “open” and “closed” conformational states of the RBD are indicated. FIG. 3B shows a monomeric S protein in an “open” state. FIG. 3C shows a cocrystal structure of the RBD with ACE2 (PDB: 6M0J). FIG. 3D shows details of amino acid residues involved in ACE2 binding. FIG. 3E shows schematic diagrams of S protein, RBD and RBM showing major functional domains and features (SEQ ID NO: 47). The RBM and ACE2-contact residues are indicated. Glycosylation sites are shown as hexagons. FIG. 3F shows SDS-PAGE of purified RBD and after treatment with endoglycosidase H and PNGase F. FIG. 3G shows ELISA showing binding of the RBD to neutralizing mAb CR3022.

FIG. 4A-C show antibody responses against the RBD immunogen. FIG. 4A shows immunization and blood collection schedule. FIG. 4B shows ELISA of pooled antisera collected about 2 weeks after each immunization. ELISA was also done using HIV-1 gp41-28×3 to assess antibodies elicited against the 6×His tag (right panel). FIG. 4C shows ELISA of antisera from individual animals after the third immunization.

FIG. 5A-D show SARS-CoV-2 neutralization assay. Vero E6 cells ($2\times10^4$ cells/well) in 96-well plates were infected with 50 pfu with various dilutions of pooled sera collected before (PRE) or after three immunizations (indicated as $1^{st}$, $2^{nd}$ and $3^{rd}$). Virus infection was monitored by CyQuant LDH (lactate dehydrogenase) Cytotoxicity Assay, which measures the level of cytosolic LDH released into the culture medium when cells die from virus infection. The assay was done in triplicate. Results from three vaccine groups are shown: FIG. 5A shows Zn-chitosan, FIG. 5B shows Alhydrogel, and FIG. 5C shows Adju-Phos. FIG. 5D shows brightfield photomicrographs of cell cultures from the neutralization assay. Results from the Alhydrogel group (for indicated immunizations and dilutions) are shown as examples.

FIG. 6A-B show detailed analyses of neutralizing antibody responses. FIG. 6A shows RT-qPCR analyses of virus neutralization assay. Cell culture supernatants from neutralization assays using antisera after the $2^{nd}$ immunization were evaluated in triplicate. Viral RNA was harvested from culture media of virus-infected cells. Following reverse transcription, qPCR was carried out using IDT 2019-nCoV RUO Kit. FIG. 6B shows extended nAb titration of antiserum from individual mouse in the Alhydrogel group after $3^{rd}$ immunizations. Pooled sera were also analyzed for comparison.

FIG. 7A-F show durability of antibody responses against the RBD. FIG. 7A-C show RBD-binding antibody levels monitored by ELISA in duplicate. FIG. 7D-F show antiviral activity assessed by neutralization assays against live, infectious SARS-CoV-2 in triplicate. Time indicates weeks after the third immunization.

FIG. 8A-C show avidity of antibodies against the RBD. ELISA was done in the presence of 1M, 2M or 3M NaSCN and compared to without to determine relative avidity index. FIG. 8A shows 1M 3M NaSCN, FIG. 8B shows 2M 3M NaSCN, and FIG. 8C shows 3M NaSCN. Serum samples collected 2 weeks after the second and 2, 12 or 20 weeks after the third immunizations were evaluated at 1:1800 dilution.

FIG. 9A-C show identification of immunogenic epitopes using overlapping peptides. FIG. 9A shows sequence of the RBD and overlapping peptides (obtained from BEI Resources) used in ELISA (SEQ ID NOs: 5-33 and 48). Amino acid residues located within the RBM are underlined. Immunogenic epitopes are highlighted in boxes. FIG. 9B shows ELISA was done using serum samples (1:300 dilution) from mice immunized with Zn-chitosan, collected six weeks after the third immunization. 200 ng of peptides were coated in each well. RBD was used as a positive control. A negative control without any peptides is indicated as “Empty”. No immunoreactive peptides were identified using serum samples from Alhydrogel or Adju-Phos groups. Peptide numbers represent those from the 181-peptide array of the S protein. FIG. 9C shows locations of the five most immunogenic linear epitopes are mapped onto the RBD structure (PDB: 6M0J).

Figure 10A:
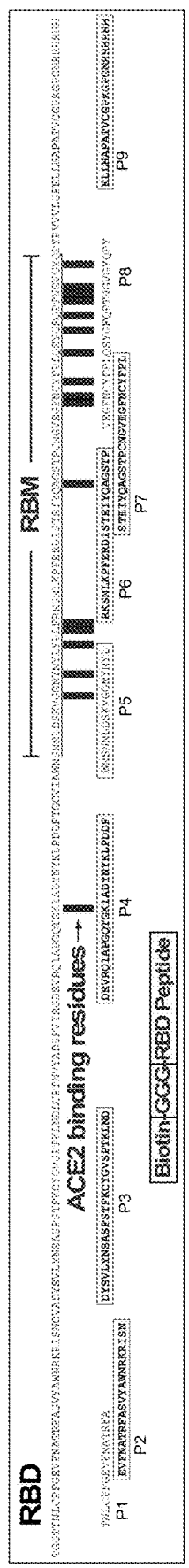
Figure 10B:
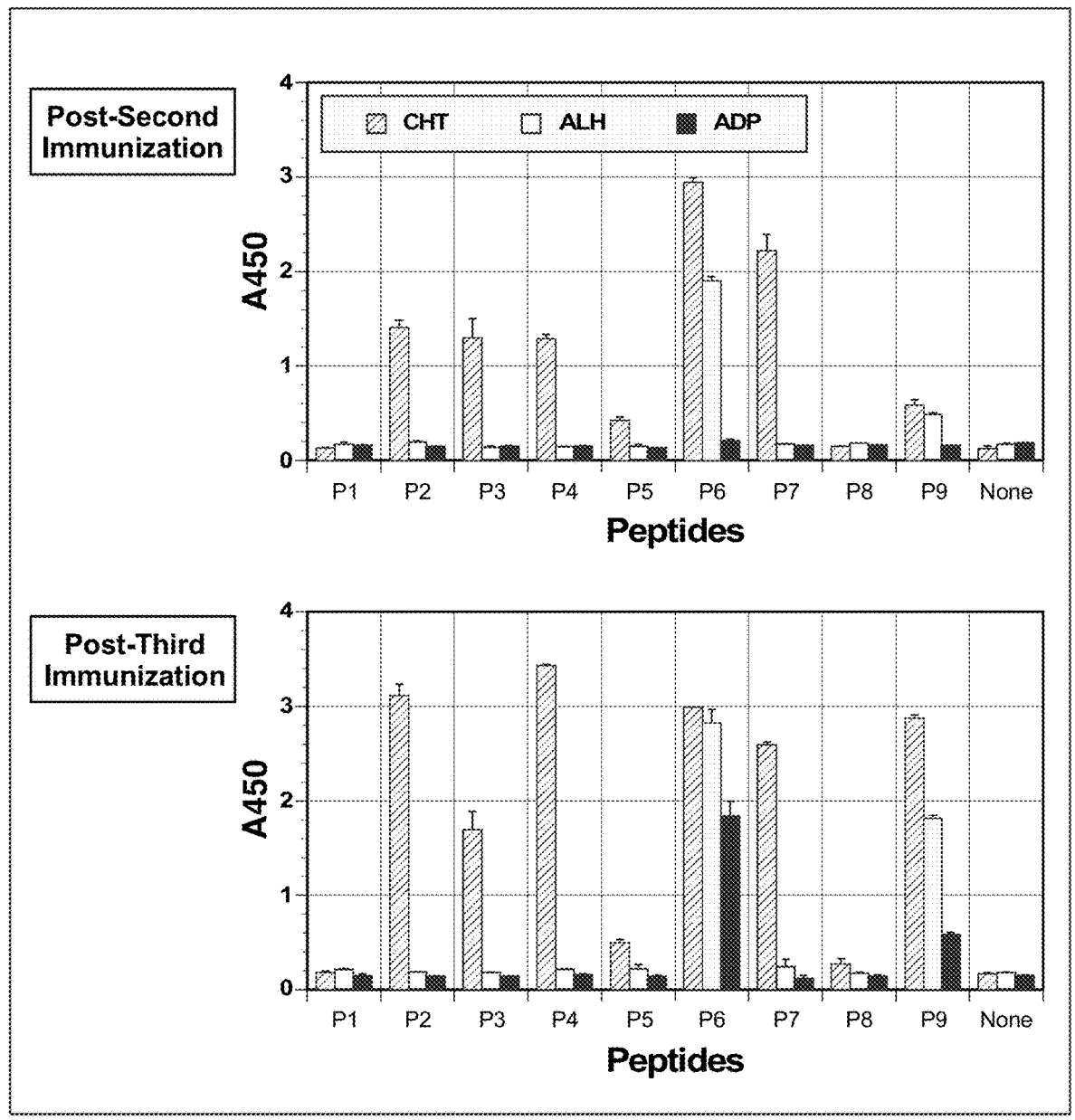
Figure 10C:
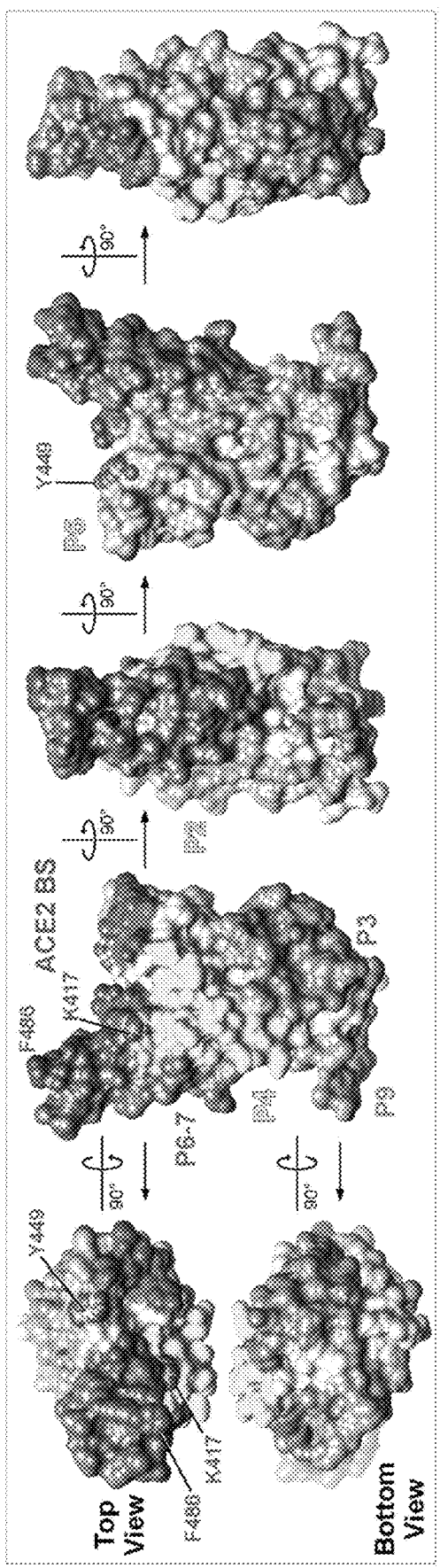
Figure 10D:
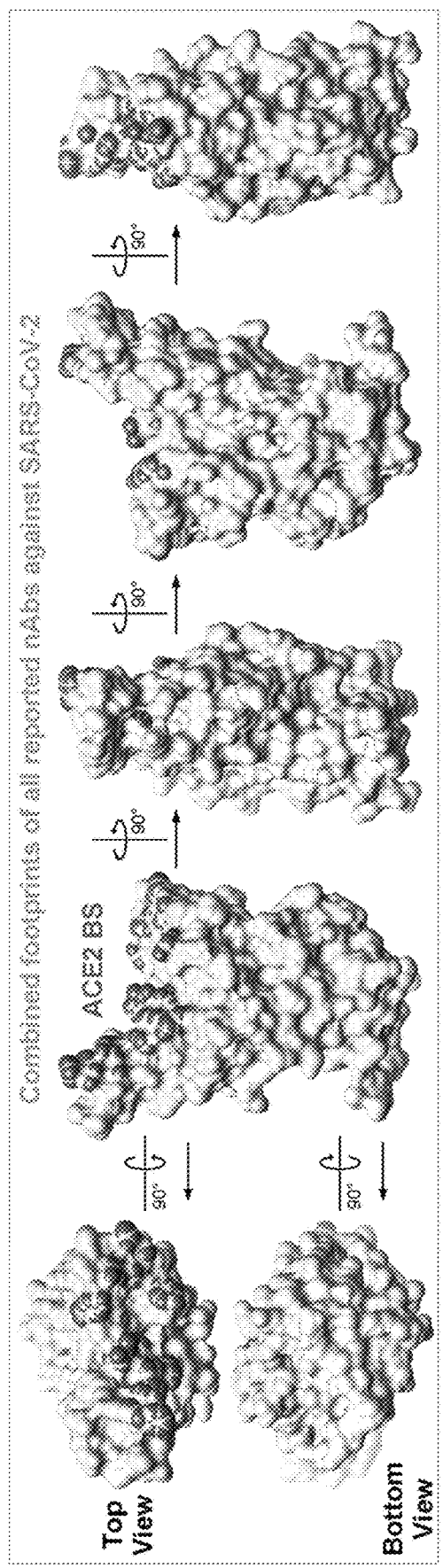

FIG. 10A-D shows identification of immunogenic epitopes using biotinylated peptides. FIG. 10A shows sequences of the RBD and biotinylated peptides used (SEQ ID NOs: 34-42 and 48). Amino acid residues located within the RBM are indicated underlined. Immunogenic epitopes are highlighted in boxes. FIG. 10B shows ELISA was done using serum samples collected two weeks after the second or third immunization (1:300 dilution). ELISA plates were coated with streptavidin (300 ng per well) and 100 ng peptides were attached to streptavidin. Negative controls without any peptides are indicated as "None". FIG. 10C shows locations of immunogenic peptides mapped onto the RBD structure (PDB: 6M0J). FIG. 10D shows combined footprints of 32 neutralizing mAbs with known crystal structures.

Figure 11C:
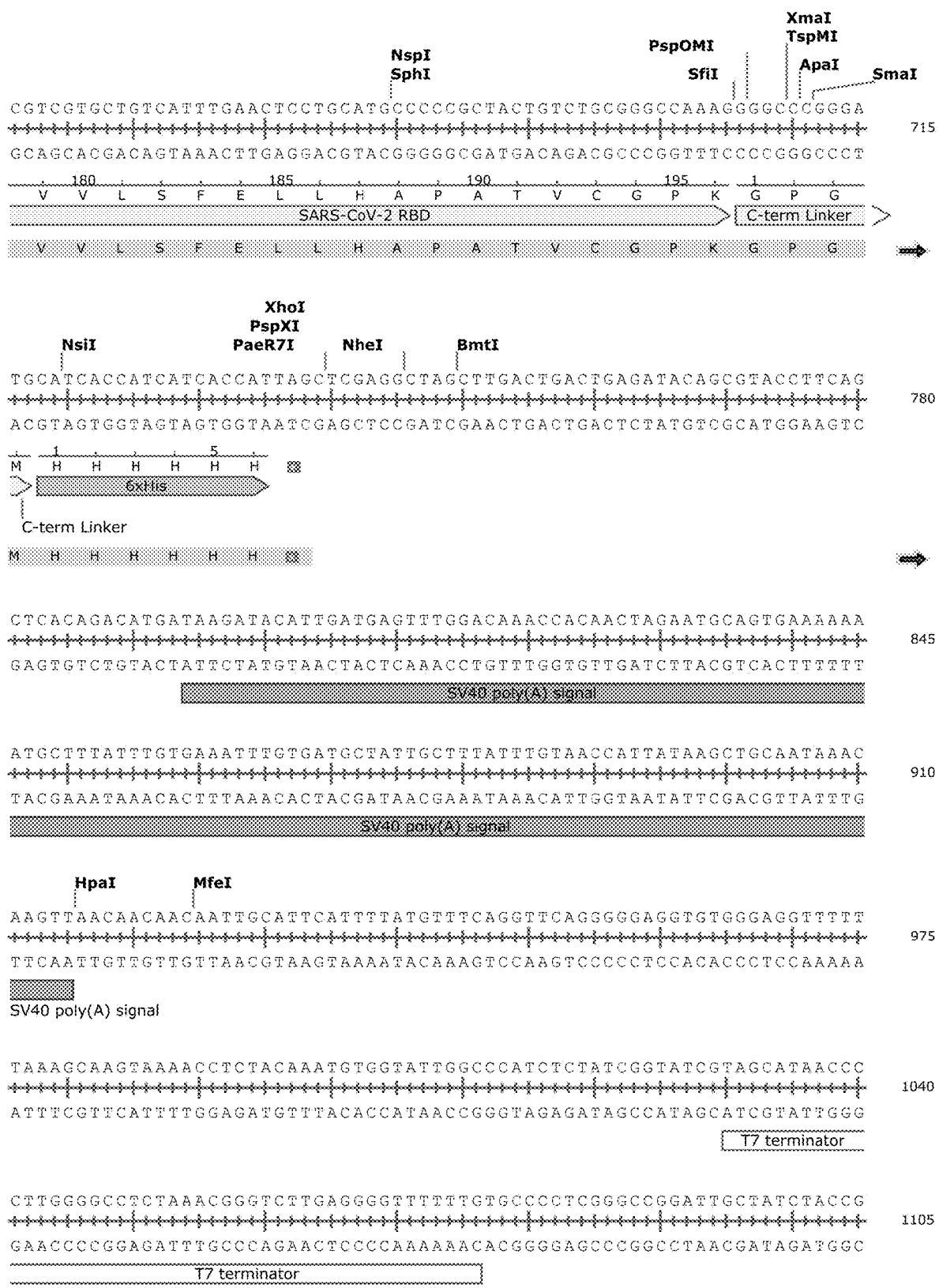
Figure 11L:
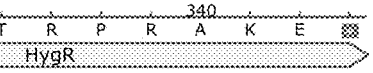

FIG. 11A-Q show the annotated sequence of pCOVID-19-RBD (SEQ ID NOs: 1 and 49-58).

DETAILED DESCRIPTION

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The singular terms "a", "an", and "the" include plural referents unless context clearly indicates otherwise. Similarly, the word "or" is intended to include "and" unless the context clearly indicate otherwise. The word "or" means any one member of a particular list and also includes any combination of members of that list.

Numeric ranges recited within the specification, including ranges of "greater than," "at least," or "less than" a numeric value, are inclusive of the numbers defining the range and include each integer within the defined range.

The term "about," as used herein, refers to variation in the numerical quantity that can occur, for example, through typical measuring techniques and equipment, with respect to any quantifiable variable, including, but not limited to, mass, volume, time, distance, wave length, frequency, voltage, current, and electromagnetic field. Further, given solid and liquid handling procedures used in the real world, there is certain inadvertent error and variation that is likely through differences in the manufacture, source, or purity of the ingredients used to make the compositions or carry out the methods and the like. The term "about" also encompasses amounts that differ due to different equilibrium conditions for a composition resulting from a particular initial mixture. The term "about" also encompasses these variations. Whether or not modified by the term "about," the claims include equivalents to the quantities.

The term "adjuvant" refers to a compound that enhances the effectiveness of the vaccine and may be added to the formulation that includes the immunizing agent. Adjuvants provide enhanced immune response even after administration of only a single dose of the vaccine. Adjuvants may include, for example, aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), non-metabolizable oil, mineral and/or plant/vegetable and/or animal oils, polymers, carbomers, surfactants, natural organic compounds, plant extracts, carbohydrates, cholesterol, lipids, water-in-oil emulsion, oil-in-water emulsion, water-in-oil-in-water emulsion, HRA-3 (acrylic acid saccharide cross-linked polymer), HRA-3 with cottonseed oil (CSO), or preferably an acrylic acid polyol cross-linked polymer. The emulsion can be based in particular on light liquid paraffin oil (European Pharmacopeia type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the PLURONIC® brand products, especially L121. See Hunter et al., The Theory and Practical Application of Adjuvants (Ed. Stewart-Tull, D. E. S.) John Wiley and Sons, NY, pp 51-94 (1995) and Todd et al., Vaccine 15:564-570 (1997). In a preferred embodiment the adjuvant is at a concentration of about 0.01 to about 50%, preferably at a concentration of about 2% to 30%, more preferably at a concentration of about 5% to about 25%, still more preferably at a concentration of about 7% to about 22%, and most preferably at a concentration of about 10% to about 20% by volume of the final product. Examples of suitable adjuvants are described in U.S. Patent Application Publication No. US2004/0213817 A1. "Adjuvanted" refers to a composition that incorporates or is combined with an adjuvant.

"Antibodies" refers to polyclonal and monoclonal antibodies, chimeric, and single chain antibodies, as well as Fab fragments, including the products of a Fab or other immunoglobulin expression library. With respect to antibodies, the term, "immunologically specific" refers to antibodies that bind to one or more epitopes of a protein of interest, but which do not substantially recognize and bind other molecules in a sample containing a mixed population of antigenic biological molecules.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylenediaminetetraacetic acid, among others.

An "epitope" is an antigenic determinant that is immunologically active in the sense that once administered to the host, it is able to evoke an immune response of the humoral (B cells) and/or cellular type (T cells). These are particular chemical groups or peptide sequences on a molecule that are antigenic. An antibody specifically binds a particular antigenic epitope on a polypeptide. In the animal, most antigens will present several or even many antigenic determinants simultaneously. Such a polypeptide may also be qualified as an immunogenic polypeptide and the epitope may be identified as described further.

An "immunogenic or immunological composition" refers to a composition of matter that comprises at least one antigen, which elicits an immunological response in the host of a cellular and/or antibody-mediated immune response to the composition or vaccine of interest. Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of clinical signs normally displayed by an infected host, a quicker recovery time and/or a lowered duration or bacterial titer in the tissues or body fluids or excretions of the infected host compared to a healthy control. Preferably said reduction in symptoms is statistically significant when compared to a control.

The term "immunogenic fragment" as used herein refers to a polypeptide or a fragment of a polypeptide, or a nucleotide sequence encoding the same which comprises an allele-specific motif, an epitope or other sequence such that the polypeptide or the fragment will bind an MHC molecule and induce a cytotoxic T lymphocyte ("CTL") response, and/or a B cell response (for example, antibody production), and/or T-helper lymphocyte response, and/or a delayed type hypersensitivity (DTH) response against the antigen from which the immunogenic polypeptide or the immunogenic fragment is derived. A DTH response is an immune reaction in which T cell-dependent macrophage activation and inflammation cause tissue injury. A DTH reaction to the subcutaneous injection of antigen is often used as an assay for cell-mediated immunity.

An "infectious DNA molecule", for purposes of the present invention, is a DNA molecule that encodes the necessary elements for viral replication, transcription, and translation into a functional virion in a suitable host cell.

The term "isolated" is used to indicate that a cell, peptide, or nucleic acid is separated from its native environment. Isolated peptides and nucleic acids may be substantially pure, i.e. essentially free of other substances with which they may be bound in nature.

For purposes of the present invention, the nucleotide sequence of a second polynucleotide molecule (either RNA or DNA) is "homologous" to the nucleotide sequence of a first polynucleotide molecule, or has "identity" to said first polynucleotide molecule, where the nucleotide sequence of the second polynucleotide molecule encodes the same polyaminoacid as the nucleotide sequence of the first polynucleotide molecule as based on the degeneracy of the genetic code, or when it encodes a polyaminoacid that is sufficiently similar to the polyaminoacid encoded by the nucleotide sequence of the first polynucleotide molecule so as to be useful in practicing the present invention. Homologous polynucleotide sequence also refers to sense and antisense strands, and in all cases to the complement of any such strands. For purposes of the present invention, a polynucleotide molecule is useful in practicing the present invention, and is therefore homologous or has identity, where it can be used as a diagnostic probe to detect the presence of SARS-CoV-2 viral polynucleotide in a fluid or tissue sample of an infected person, e.g. by standard hybridization or amplification techniques. Generally, the nucleotide sequence of a second polynucleotide molecule is homologous to the nucleotide sequence of a first polynucleotide molecule if it has at least about 70% nucleotide sequence identity to the nucleotide sequence of the first polynucleotide molecule as based on the BLASTN algorithm (National Center for Biotechnology Information, otherwise known as NCBI, (Bethesda, Md., USA) of the United States National Institute of Health). In a specific example for calculations according to the practice of the present invention, reference is made to BLASTP 2.2.6 [Tatusova T A and T L Madden, "BLAST 2 sequences—a new tool for comparing protein and nucleotide sequences." (1999) FEMS Microbiol Lett. 174:247-250.]. Briefly, two amino acid sequences are aligned to optimize the alignment scores using a gap opening penalty of 10, a gap extension penalty of 0.1, and the "blosum62" scoring matrix of Henikoff and Henikoff (Proc. Nat. Acad. Sci. USA 325 89:10915-10919. 1992). The percent identity is then calculated as: Total number of identical matches×100/divided by the length of the longer sequence+number of gaps introduced into the longer sequence to align the two sequences.

Preferably, a homologous nucleotide sequence has at least about 75% nucleotide sequence identity, even more preferably at least about 80%, 85%, 90%, 95%, 96%, 97%, 98%, 99%, and 99.5% nucleotide sequence identity. Since the genetic code is degenerate, a homologous nucleotide sequence can include any number of "silent" base changes, i.e. nucleotide substitutions that nonetheless encode the same amino acid.

A homologous nucleotide sequence can further contain non-silent mutations, i.e. base substitutions, deletions, or additions resulting in amino acid differences in the encoded polyaminoacid, so long as the sequence remains at least about 70% identical to the polyaminoacid encoded by the first nucleotide sequence or otherwise is useful for practicing the present invention. In this regard, certain conservative amino acid substitutions may be made which are generally recognized not to inactivate overall protein function: such as in regard of positively charged amino acids (and vice versa), lysine, arginine and histidine; in regard of negatively charged amino acids (and vice versa), aspartic acid and glutamic acid; and in regard of certain groups of neutrally charged amino acids (and in all cases, also vice versa), (1) alanine and serine, (2) asparagine, glutamine, and histidine, (3) cysteine and serine, (4) glycine and proline, (5) isoleucine, leucine and valine, (6) methionine, leucine and isoleucine, (7) phenylalanine, methionine, leucine, and tyrosine, (8) serine and threonine, (9) tryptophan and tyrosine, (10) and for example tyrosine, tryptophan and phenylalanine. Amino acids can be classified according to physical properties and contribution to secondary and tertiary protein structure. A conservative substitution is thus recognized in the art as a substitution of one amino acid for another amino acid that has similar properties, and exemplary conservative substitutions may be found in WO 97/09433, page 10, published Mar. 13, 1997 (PCT/GB96/02197, filed Sep. 6, 1996). Alternatively, conservative amino acids can be grouped as described in Lehninger, (Biochemistry, Second Edition; Worth Publishers, Inc. NY: NY (1975), pp. 71-77). Protein sequences can be aligned using both Vector NTI Advance 11.5 and CLUSTAL 2.1 multiple sequence alignment. As used herein the recitation of a particular amino acid or nucleotide sequence shall include all silent mutations with respect to nucleic acid sequence and any and all conservatively modified variants with respect to amino acid sequences.

Homologous nucleotide sequences can be determined by comparison of nucleotide sequences, for example by using BLASTN, above. Alternatively, homologous nucleotide sequences can be determined by hybridization under selected conditions. For example, the nucleotide sequence of a second polynucleotide molecule is homologous to SEQ ID NO:1 (or any other particular polynucleotide sequence) if it hybridizes to the complement of SEQ ID NO:1 under moderately stringent conditions, e.g., hybridization to filter-bound DNA in 0.5 M $NaHPO_4$, 7% sodium dodecyl sulfate (SDS), 1 mM EDTA at 65° C., and washing in 0.2×SSC/ 0.1% SDS at 42° C. (see Ausubel et al editors, Protocols in Molecular Biology, Wiley and Sons, 1994, pp. 6.0.3 to 6.4.10), or conditions which will otherwise result in hybridization of sequences that encode a SARS-CoV-2 virus. Modifications in hybridization conditions can be empirically determined or precisely calculated based on the length and percentage of guanosine/cytosine (GC) base pairing of the probe. The hybridization conditions can be calculated as described in Sambrook, et al., (Eds.), Molecular Cloning: A Laboratory Manual, Cold Spring Harbor Laboratory Press: Cold Spring Harbor, N.Y. (1989), pp. 9.47 to 9.51.

It is furthermore to be understood that the isolated polynucleotide molecules and the isolated RNA molecules of the present invention include both synthetic molecules and molecules obtained through recombinant techniques, such as by in vitro cloning and transcription.

As used herein, "a pharmaceutically acceptable carrier" or "pharmaceutical carrier" includes any and all excipients, solvents, growth media, dispersion media, coatings, adjuvants, stabilizing agents, diluents, preservatives, inactivating agents, antimicrobial, antibacterial and antifungal agents, isotonic agents, adsorption delaying agents, and the like. Such ingredients include those that are safe and appropriate for use in veterinary applications. Pharmaceutically acceptable carriers are typically non-toxic, inert, solid or liquid carriers.

A "susceptible" host as used herein refers to a cell or an animal that can be infected by SARS-CoV-2. When introduced to a susceptible animal, an attenuated SARS-CoV-2 may also induce an immunological response against the SARS-CoV-2 or its antigen, and thereby render the animal immunity against SARS-CoV-2 infection.

The term "vaccine" refers to an antigenic preparation used to produce immunity to a disease, in order to prevent or ameliorate the effects of infection. Vaccines are typically prepared using a combination of an immunologically effective amount of an immunogen together with an adjuvant effective for enhancing the immune response of the vaccinated subject against the immunogen.

Vaccine formulations will contain a "therapeutically effective amount" of the active ingredient, that is, an amount capable of eliciting an induction of an immunoprotective response in a subject to which the composition is administered. In the treatment and prevention of SARS-CoV-2, for example, a "therapeutically effective amount" would preferably be an amount that enhances resistance of the vaccinated subject to new infection and/or reduces the clinical severity of the disease. Such protection will be demonstrated by either a reduction or lack of symptoms normally displayed by a subject infected with SARS-CoV-2, a quicker recovery time and/or a lowered count of virus particles. Vaccines can be administered prior to infection, as a preventative measure against SARS-CoV-2. Alternatively, vaccines can be administered after the subject already has contracted a disease. Vaccines given after exposure to SARS-CoV-2 may be able to attenuate the disease, triggering a superior immune response than the natural infection itself.

The present invention provides for reduction of the incidence of and/or severity of clinical symptoms associated with SARS-CoV-2 infection. Preferably, the severity and/or incidence of clinical symptoms in animals receiving the immunogenic composition of the present invention are reduced at least 10% in comparison to animals not receiving such an administration when both groups (animals receiving and animals not receiving the composition) are challenged with or exposed to infection by SARS-CoV-2. More preferably, the incidence or severity is reduced at least 20%, even more preferably, at least 30%, still more preferably, at least 40%, even more preferably, at least 50%, still more preferably, at least 60%, even more preferably, at least 70%, still more preferably, at least 80%, even more preferably, at least 90%, still more preferably, at least 95%, and most preferably, at least 100%, wherein the animals receiving the composition of the present invention exhibit no clinical symptoms, or alternatively exhibit clinical symptoms of reduced severity. Any animal that is susceptible to SARS-CoV-2 may be a subject for the immunogenic composition of the invention. For example, in addition to humans, the CDC has reported that SARS-CoV-2 can infect cats, dogs, mink, and large cats including lions and tigers. The invention has applications in treatment of these animals as well.

For the purpose of the practice of all aspects of the invention, it is well known to those skilled in the art that there is no absolute immunological boundary in immunological assays in regard of animals that are seronegative for exposure to a particular antigen or pathogen, and those that are seropositive (having been exposed to a vaccine or pathogen). Nonetheless, those skilled in the art would recognize that in serum neutralization assays, seropositive animals would generally be detected at least up to a 1:1000 serum dilution, whereas a seronegative animal would be expected not to neutralize at a higher dilution than about 1:20 or 1:10.

Vaccine & Immunogenic Compositions

Disclosed herein is an immunogenic composition, suitable to be used as a vaccine, which comprises a SARS-CoV-2 strain according to the invention. The immunogenic compositions according to the invention elicit a specific humoral immune response toward the SARS-CoV-2 comprising neutralizing antibodies.

The immunogenic and vaccine compositions of this invention are not, however, restricted to any particular type or method of preparation. These include, but are not limited to, infectious DNA vaccines (i.e., using plasmids, vectors or other conventional carriers to directly inject DNA into person), live vaccines, modified live vaccines, inactivated vaccines, subunit vaccines, attenuated vaccines, genetically engineered vaccines, etc. These vaccines are prepared by standard methods known in the art.

Proteinaceous Vaccines and Immunogenic Compositions

In embodiments of the disclosure, a composition induces an immune response to the antigen in a cell, tissue or animal (e.g., a human). As used herein, an "antigenic composition" (which alternatively may be referred to as an "immunogenic composition") may comprise an antigen (e.g., a protein, peptide, or polypeptide) or a modified version of an antigen. In particular embodiments the antigenic composition comprises or encodes all or part of the receptor-binding domain of the SARS-CoV-2 spike protein or a mutated version thereof, including a deglycosylated, or amino acid modified version thereof. In certain embodiments, the immunogenic composition or vaccine comprises at least one adjuvant. In other embodiments, the antigenic composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

In certain embodiments, an antigenic composition or immunologically functional equivalent may be used as an effective vaccine in inducing an anti-SARS-CoV-2 humoral and/or cell-mediated immune response in an animal, including human. The present invention contemplates one or more antigenic compositions or vaccines for use in both active and passive immunization embodiments.

A vaccine or immunogenic composition of the present invention may vary in its composition of proteinaceous components. It will be understood that various compositions described herein may further comprise additional components. For example, one or more vaccine or immunogenic composition components may be comprised in a lipid or liposome. In another non-limiting example, a vaccine or immunogenic composition may comprise one or more adjuvants. A vaccine or immunogenic composition of the present disclosure, and its various components, may be prepared and/or administered by any method disclosed herein or as would be known to one of ordinary skill in the art, in light of the present disclosure.

It is understood that an immunogenic composition may be made by a method that is well known in the art, including but not limited to chemical synthesis by solid phase synthesis and purification away from the other products of the chemical reactions by HPLC, or production by the expression of a nucleic acid sequence (e.g., a DNA sequence) encoding a peptide or polypeptide comprising an antigen of the present invention in an in vitro translation system or in a living cell including, for example, in a yeast cell, bacterial, mammalian cells or baculovirus/insect cells. The antigenic composition may be isolated and extensively purified to remove one or more undesired small molecular weight molecules and/or lyophilized for more ready formulation into a desired vehicle. It is further understood that amino acid additions, deletions, mutations, chemical modification and such like that are made in an antigenic composition component, such as a vaccine, will preferably not substantially interfere with the antibody recognition of the epitopic sequence.

A peptide or polypeptide corresponding to one or more antigenic determinants of the receptor binding domain of the SARS-CoV-2 spike protein may generally be 10-20 amino acid residues in length, and may contain more than one peptide determinants or up to about 30-50 residues or so. A peptide sequence may be synthesized by methods known to those of ordinary skill in the art, such as, for example, peptide synthesis using automated peptide synthesis machines, such as those available from Applied Biosystems (Foster City, Calif.).

Longer peptides or polypeptides also may be prepared, e.g., by recombinant means. In certain embodiments, a nucleic acid encoding an antigenic composition and/or a component described herein may be used, for example, to produce an antigenic composition in vitro or in vivo for the various compositions and methods of the present invention. For example, in certain embodiments, a nucleic acid encoding an antigen is comprised in, for example, a vector in a recombinant cell. The nucleic acid may be expressed to produce a peptide or polypeptide comprising an antigenic sequence. The peptide or polypeptide may be secreted from the cell, or comprised as part of or within the cell.

A. Immunologically Functional Equivalents

As modifications and changes may be made in the structure of an antigenic composition of the present disclosure, and still obtain molecules having like or otherwise desirable characteristics, such immunologically functional equivalents are also encompassed within the present invention.

For example, certain amino acids may be substituted for other amino acids in a peptide, polypeptide or protein structure without appreciable loss of interactive binding capacity with structures such as, for example, antigen-binding regions of antibodies, binding sites on substrate molecules or receptors, DNA binding sites, or such like. Since it is the interactive capacity and nature of a peptide, polypeptide or protein that defines its biological (e.g., immunological) functional activity, certain amino acid sequence substitutions can be made in an amino acid sequence (or, of course, its underlying DNA coding sequence) and nevertheless obtain a peptide or polypeptide with like (agonistic) properties. It is thus contemplated by the inventors that various changes may be made in the sequence of an antigenic composition such as, for example a SARS Co-V RBD peptide or polypeptide without appreciable loss of biological utility or activity. In particular cases, one or more of the glycosylation sites of RBD is mutated or deleted and in particular embodiments there is also one or more other amino acids that are modified compared to the corresponding wild-type sequence.

As used herein, an "amino molecule" refers to any amino acid, amino acid derivative or amino acid mimic as would be known to one of ordinary skill in the art. In certain embodiments, the residues of the antigenic composition comprises amino molecules that are sequential, without any non-amino molecule interrupting the sequence of amino molecule residues. In other embodiments, the sequence may comprise one or more non-amino molecule moieties. In particular embodiments, the sequence of residues of the antigenic composition may be interrupted by one or more non-amino molecule moieties.

Accordingly, antigenic compositions, particularly an immunologically functional equivalent of the sequences disclosed herein, may encompass an amino molecule sequence comprising at least one of the 20 common amino acids in naturally synthesized proteins, or at least one modified or unusual amino acid.

In term of immunologically functional equivalent, it is well understood by the skilled artisan that, inherent in the definition is the concept that there is a limit to the number of changes that may be made within a defined portion of the molecule and still result in a molecule with an acceptable level of equivalent immunological activity. An immunologically functional equivalent peptide or polypeptide are thus defined herein as those peptide(s) or polypeptide(s) in which certain, not most or all, of the amino acid(s) may be substituted.

In particular, where a shorter length peptide is concerned, it is contemplated that fewer amino acid substitutions should be made within the given peptide. A longer polypeptide may have an intermediate number of changes. The full length protein will have the most tolerance for a larger number of changes. Of course, a plurality of distinct polypeptides/peptides with different substitutions may easily be made and used in accordance with the invention.

It also is well understood that where certain residues are shown to be particularly important to the immunological or structural properties of a protein or peptide, e.g., residues in binding regions or active sites, such residues may not generally be exchanged. This is an important consideration in the present invention, where changes in the antigenic site should be carefully considered and subsequently tested to ensure maintenance of immunological function (e.g., antigenicity), where maintenance of immunological function is desired. In this manner, functional equivalents are defined herein as those peptides or polypeptides which maintain a substantial amount of their native immunological activity.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as immunologically functional equivalents.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein, polypeptide or peptide is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within .+−.2 is preferred, those which are within .+−.1 are particularly preferred, and those within .+−.0.5 are even more particularly preferred.

It also is understood in the art that the substitution of like amino acids can be made effectively on the basis of hydrophilicity, particularly where the immunological functional equivalent polypeptide or peptide thereby created is intended for use in immunological embodiments, as in certain embodiments of the present invention. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a immunological property of the protein.

As detailed in U.S. Pat. No. 4,554,101, the following hydrophilicity values have been assigned to amino acid residues: arginine (+3.0); lysine (+3.0); aspartate (+3.0.+−.1); glutamate (+3.0.+−.1); serine (+0.3); asparagine (+0.2); glutamine (+0.2); glycine (0); threonine (−0.4); proline (−0.5.+−.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within .+−.2 is preferred, those which are within .+−.1 are particularly preferred, and those within .+−.0.5 are even more particularly preferred.

Numerous scientific publications have also been devoted to the prediction of secondary structure, and to the identification of an epitope, from analyses of an amino acid sequence (Chou & Fasman, 1974a,b; 1978a,b, 1979). Any of these may be used, if desired, to supplement the teachings of U.S. Pat. No. 4,554,101.

Moreover, computer programs are currently available to assist with predicting an antigenic portion and an epitopic core region of one or more proteins, polypeptides or peptides. Examples include those programs based upon the Jameson-Wolf analysis (Jameson & Wolf, 1988; Wolf et al., 1988), the program PepPlot™ (Brutlag et al., 1990; Weinberger et al., 1985), and other new programs for protein tertiary structure prediction (Fetrow & Bryant, 1993). Another commercially available software program capable of carrying out such analyses is MacVector (IBI, New Haven, Conn.).

In further embodiments, major antigenic determinants of a peptide or polypeptide may be identified by an empirical approach in which portions of a nucleic acid encoding a peptide or polypeptide are expressed in a recombinant host, and the resulting peptide(s) or polypeptide(s) tested for their ability to elicit an immune response. For example, PCR can be used to prepare a range of peptides or polypeptides lacking successively longer fragments of the C-terminus of the amino acid sequence. The immunoactivity of each of these peptides or polypeptides is determined to identify those fragments or domains that are immunodominant. Further studies in which only a small number of amino acids are removed at each iteration then allows the location of the antigenic determinant(s) of the peptide or polypeptide to be more precisely determined.

Another method for determining a major antigenic determinant of a peptide or polypeptide is the SPOTs™ system (Genosys Biotechnologies, Inc., The Woodlands, Tex.). In this method, overlapping peptides are synthesized on a cellulose membrane, which following synthesis and deprotection, is screened using a polyclonal or monoclonal antibody. An antigenic determinant of the peptides or polypeptides which are initially identified can be further localized by performing subsequent syntheses of smaller peptides with larger overlaps, and by eventually replacing individual amino acids at each position along the immunoreactive sequence.

Once one or more such analyses are completed, an antigenic composition, such as for example a peptide or a polypeptide is prepared that contain at least the essential features of one or more antigenic determinants. An antigenic composition is then employed in the generation of antisera against the composition, and preferably the antigenic determinant(s).

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. Nucleic acids encoding these antigenic compositions also can be constructed and inserted into one or more expression vectors by standard methods (Sambrook et al., 1987), for example, using PCR cloning methodology.

In addition to the peptidyl compounds described herein, the inventors also contemplate that other sterically similar compounds may be formulated to mimic the key portions of the peptide or polypeptide structure or to interact specifically with, for example, an antibody. Such compounds, which may be termed peptidomimetics, may be used in the same manner as a peptide or polypeptide of the invention and hence are also immunologically functional equivalents.

Certain mimetics that mimic elements of protein secondary structure are described in Johnson et al. (1993). The underlying rationale behind the use of peptide mimetics is that the peptide backbone of proteins exists chiefly to orientate amino acid side chains in such a way as to facilitate molecular interactions, such as those of antibody and antigen. A peptide mimetic is thus designed to permit molecular interactions similar to the natural molecule.

B. Antigen Mutagenesis

In particular embodiments, an antigenic composition is mutated for purposes such as, for example, enhancing its immunogenicity or producing or identifying a immunologically functional equivalent sequence. Methods of mutagenesis are well known to those of skill in the art (Sambrook et al., 1987).

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In a preferred embodiment, site directed mutagenesis is used. Site-specific mutagenesis is a technique useful in the preparation of an antigenic composition, through specific mutagenesis of the underlying DNA. In general, the technique of site-specific mutagenesis is well known in the art. The technique further provides a ready ability to prepare and test sequence variants, incorporating one or more of the foregoing considerations, by introducing one or more nucleotide sequence changes into the DNA. Site-specific mutagenesis allows the production of a mutant through the use of specific oligonucleotide sequence(s) which encode the DNA sequence of the desired mutation, as well as a sufficient number of adjacent nucleotides, to provide a primer sequence of sufficient size and sequence complexity to form a stable duplex on both sides of the position being mutated. Typically, a primer of about 17 to about 75 nucleotides in length is preferred, with about 10 to about 25 or more residues on both sides of the position being altered, while primers of about 17 to about 25 nucleotides in length being more preferred, with about 5 to 10 residues on both sides of the position being altered.

In general, site-directed mutagenesis is performed by first obtaining a single-stranded vector, or melting of two strands of a double stranded vector which includes within its sequence a DNA sequence encoding the desired protein. As will be appreciated by one of ordinary skill in the art, the technique typically employs a bacteriophage vector that exists in both a single stranded and double stranded form.

Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

This mutagenic primer is then annealed with the single-stranded DNA preparation, and subjected to DNA polymerizing enzymes such as, for example, *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

Alternatively, a pair of primers may be annealed to two separate strands of a double stranded vector to simultaneously synthesize both corresponding complementary strands with the desired mutation(s) in a PCR reaction. A genetic selection scheme to enrich for clones incorporating the mutagenic oligonucleotide has been devised (Kunkel et al., 1987). Alternatively, the use of PCR with commercially available thermostable enzymes such as Taq polymerase may be used to incorporate a mutagenic oligonucleotide primer into an amplified DNA fragment that can then be cloned into an appropriate cloning or expression vector (Tomic et al., 1990; Upender et al., 1995). A PCR employing a thermostable ligase in addition to a thermostable polymerase also may be used to incorporate a phosphorylated mutagenic oligonucleotide into an amplified DNA fragment that may then be cloned into an appropriate cloning or expression vector (Michael 1994).

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

Additionally, one particularly useful mutagenesis technique is alanine scanning mutagenesis in which a number of residues are substituted individually with the amino acid alanine so that the effects of losing side-chain interactions can be determined, while minimizing the risk of large-scale perturbations in protein conformation (Cunningham et al., 1989).

C. Liposome Mediated Transfection

In a further embodiment of the invention, one or more vaccine or immunogenic composition components may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991).

D. Vaccine or Immunogenic Composition Component Purification

In any case, a vaccine component (e.g., an antigenic peptide or polypeptide) may be isolated and/or purified from the chemical synthesis reagents, cell or cellular components.

In a method of producing the vaccine or immunogenic composition component, purification is accomplished by any appropriate technique that is described herein or well-known to those of skill in the art (e.g., Sambrook et al., 1987). There is no general requirement that an antigenic composition of the present invention or other vaccine component always be provided in their most purified state. Indeed, it is contemplated that less substantially purified vaccine or immunogenic composition component, which is nonetheless enriched in the desired compound, relative to the natural state, will have utility in certain embodiments, such as, for example, total recovery of protein product, or in maintaining the activity of an expressed protein. However, it is contemplated that inactive products also have utility in certain embodiments, such as, e.g., in determining antigenicity via antibody generation.

The present invention also provides purified, and in certain embodiments, substantially purified vaccines or immunogenic composition components. The term "purified vaccine component" or "purified immunogenic composition component" as used herein, is intended to refer to at least one respective vaccine or immunogenic composition component (e.g., a proteinaceous composition, isolatable from cells), wherein the component is purified to any degree relative to its naturally-obtainable state, e.g., relative to its purity within a cellular extract or reagents of chemical synthesis. In certain aspects wherein the vaccine component is a proteinaceous composition, a purified vaccine component also refers to a wild-type or mutant protein, polypeptide, or peptide free from the environment in which it naturally occurs.

Where the term "substantially purified" is used, this will refer to a composition in which the specific compound (e.g., a protein, polypeptide, or peptide) forms the major component of the composition, such as constituting about 50% of the compounds in the composition or more. In preferred embodiments, a substantially purified vaccine component will constitute more than about 60%, about 70%, about 80%, about 90%, about 95%, about 99% or even more of the compounds in the composition.

In certain embodiments, a vaccine or immunogenic composition component may be purified to homogeneity. As applied to the present invention, "purified to homogeneity," means that the vaccine component has a level of purity where the compound is substantially free from other chemicals, biomolecules or cells. For example, a purified peptide, polypeptide or protein will often be sufficiently free of other protein components so that degradative sequencing may be performed successfully. Various methods for quantifying the degree of purification of a vaccine component will be known to those of skill in the art in light of the present disclosure. These include, for example, determining the specific protein activity of a fraction (e.g., antigenicity), or assessing the number of polypeptides within a fraction by gel electrophoresis.

Various techniques suitable for use in chemical, biomolecule or biological purification, well known to those of skill in the art, may be applicable to preparation of a vaccine component of the present invention. These include, for example, precipitation with ammonium sulfate, PEG, antibodies and the like or by heat denaturation, followed by centrifugation; fractionation, chromatographic procedures, including but not limited to, partition chromatograph (e.g., paper chromatograph, thin-layer chromatograph (TLC), gas-liquid chromatography and gel chromatography) gas chromatography, high performance liquid chromatography, affinity chromatography, supercritical flow chromatography ion exchange, gel filtration, reverse phase, hydroxylapatite, lectin affinity; isoelectric focusing and gel electrophoresis (see for example, Sambrook et al. 1989; and Freifelder, Physical Biochemistry, Second Edition, pages 238-246, incorporated herein by reference).

Given many DNA and proteins are known (see for example, the National Center for Biotechnology Information's GenBank™ and GenPept™ databases, or may be identified and amplified using the methods described herein, any purification method for recombinantly expressed nucleic acid or proteinaceous sequences known to those of skill in the art can now be employed. In certain aspects, a nucleic acid may be purified on polyacrylamide gels, and/or cesium chloride centrifugation gradients, or by any other means known to one of ordinary skill in the art (see for example, Sambrook et al. 1989, incorporated herein by reference). In further aspects, a purification of a proteinaceous sequence may be conducted by recombinantly expressing the sequence as a fusion protein. Such purification methods are routine in the art. This is exemplified by the generation of an specific protein-glutathione S-transferase fusion protein, expression in *E. coli*, and isolation to homogeneity using affinity chromatography on glutathione-agarose or the generation of a polyhistidine tag on the N- or C-terminus of the protein, and subsequent purification using Ni-affinity chromatography. In particular aspects, cells or other components of the vaccine may be purified by flow cytometry. Flow cytometry involves the separation of cells or other particles in a liquid sample, and is well known in the art (see, for example, U.S. Pat. Nos. 3,826,364, 4,284,412, 4,989,977, 4,498,766, 5,478,722, 4,857,451, 4,774,189, 4,767,206, 4,714,682, 5,160,974 and 4,661,913). Any of these techniques described herein, and combinations of these and any other techniques known to skilled artisans, may be used to purify and/or assay the purity of the various chemicals, proteinaceous compounds, nucleic acids, cellular materials and/or cells that may comprise a vaccine of the present invention. As is generally known in the art, it is believed that the order of conducting the various purification steps may be changed, or that certain steps may be omitted, and still result in a suitable method for the preparation of a substantially purified antigen or other vaccine component.

E. Additional Vaccine Components

It is contemplated that an antigenic composition of the invention may be combined with one or more additional components to form a more effective composition or vaccine. Non-limiting examples of additional components include, for example, one or more additional antigens, immunomodulators or adjuvants to stimulate an immune response to an antigenic composition of the present invention and/or the additional component(s).

1. Immunomodulators

For example, it is contemplated that immunomodulators can be included in the vaccine to augment a cell's or a patient's (e.g., an animal's) response. Immunomodulators can be included as purified proteins, nucleic acids encoding immunomodulators, and/or cells that express immunomodulators in the vaccine composition, for example. The following sections list non-limiting examples of immunomodulators that are of interest, and it is contemplated that various combinations of immunomodulators may be used in certain embodiments (e.g., a cytokine and a chemokine).

Interleukins, cytokines, nucleic acids encoding interleukins or cytokines, and/or cells expressing such compounds are contemplated as possible vaccine components. Interleukins and cytokines, include but are not limited to interleukin 1 (IL-1), IL-2, IL-3, IL-4, IL-5, IL-6, IL-7, IL-8, IL-9, IL-10, IL-11, IL-12, IL-13, IL-14, IL-15, IL-18, .beta.-interferon, .alpha-interferon, .gamma-interferon, angiostatin, thrombospondin, endostatin, GM-CSF, G-CSF, M-CSF, METH-1, METH-2, tumor necrosis factor, TGF.beta., LT and combinations thereof.

Chemokines, nucleic acids that encode for chemokines, and/or cells that express such also may be used as vaccine components. Chemokines generally act as chemoattractants to recruit immune effector cells to the site of chemokine expression. It may be advantageous to express a particular chemokine coding sequence in combination with, for example, a cytokine coding sequence, to enhance the recruitment of other immune system components to the site of treatment. Such chemokines include, for example, RANTES, MCAF, MIP1-alpha, MIP1-Beta, IP-10 and combinations thereof. The skilled artisan will recognize that certain cytokines are also known to have chemoattractant effects and could also be classified under the term chemokines.

In certain embodiments, an antigenic composition may be chemically coupled to a carrier or recombinantly expressed with a immunogenic carrier peptide or polypeptide (e.g., a antigen-carrier fusion peptide or polypeptide) to enhance an immune reaction. Exemplary and preferred immunogenic carrier amino acid sequences include hepatitis B surface antigen, keyhole limpet hemocyanin (KLH) and bovine serum albumin (BSA). Other albumins such as ovalbumin, mouse serum albumin or rabbit serum albumin also can be used as immunogenic carrier proteins. Means for conjugating a polypeptide or peptide to a immunogenic carrier protein are well known in the art and include, for example, glutaraldehyde, m-maleimidobenzoyl-N-hydroxysuccinimide ester, carbodiimide and bis-biazotized benzidine.

It may be desirable to coadminister biologic response modifiers (BRM), which have been shown to upregulate T cell immunity or downregulate suppressor cell activity. Such BRMs include, but are not limited to, cimetidine (CIM; 1200 mg/d) (Smith/Kline, PA); low-dose cyclophosphamide (CYP; 300 mg/m.sup.2) (Johnson/Mead, NJ), or a gene encoding a protein involved in one or more immune helper functions, such as B-7.

2. Adjuvants

Immunization protocols have used adjuvants to stimulate responses for many years, and as such adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation. In one aspect, an adjuvant effect is achieved by use of an agent, such as alum, used in about 0.05 to about 0.1% solution in phosphate buffered saline. Alternatively, the antigen is made as an admixture with synthetic polymers of sugars (Carbopol™) used as an about 0.25% solution. Adjuvant effect may also be made my aggregation of the antigen in the vaccine by heat treatment with temperatures ranging between about 70° to about 101° C. for a 30-second to 2-minute period, respectively. Aggregation by reactivating with pepsin treated (Fab) antibodies to albumin, mixture with bacterial cell(s) such as C. parvum, an endotoxin or a lipopolysaccharide component of Gram-negative bacteria, emulsion in physiologically acceptable oil vehicles, such as mannide monooleate (Aracel A), or emulsion with a 20% solution of a perfluorocarbon (Fluosol-DA™) used as a block substitute, also may be employed.

Some adjuvants, for example, certain organic molecules obtained from bacteria, act on the host rather than on the antigen. An example is muramyl dipeptide (N-acetylmuramyl-L-alanyl-D-isoglutamine [MDP]), a bacterial peptidoglycan. The effects of MDP, as with most adjuvants, are not fully understood. MDP stimulates macrophages but also appears to stimulate B cells directly. The effects of adjuvants, therefore, are not antigen-specific. If they are administered together with a purified antigen, however, they can be used to selectively promote the response to the antigen.

Adjuvants have been used experimentally to promote a generalized increase in immunity against unknown antigens (e.g., U.S. Pat. No. 4,877,611). In certain embodiments, hemocyanins and hemoerythrins may also be used in the invention. The use of hemocyanin from keyhole limpet (KLH) is preferred in certain embodiments, although other molluscan and arthropod hemocyanins and hemoerythrins may be employed.

Various polysaccharide adjuvants may also be used. For example, the use of various pneumococcal polysaccharide adjuvants on the antibody responses of mice has been described (Yin et al., 1989). The doses that produce optimal responses, or that otherwise do not produce suppression, should be employed as indicated (Yin et al., 1989). Polyamine varieties of polysaccharides are particularly preferred, such as chitin and chitosan, including deacetylated chitin.

Another group of adjuvants are the muramyl dipeptide (MDP, N-acetylmuramyl-L-alanyl-D-isoglutamine) group of bacterial peptidoglycans. Derivatives of muramyl dipeptide, such as the amino acid derivative threonyl-MDP, and the fatty acid derivative MTPPE, are also contemplated.

U.S. Pat. No. 4,950,645 describes a lipophilic disaccharide-tripeptide derivative of muramyl dipeptide which is described for use in artificial liposomes formed from phosphatidyl choline and phosphatidyl glycerol. It is the to be effective in activating human monocytes and destroying tumor cells, but is non-toxic in generally high doses. The compounds of U.S. Pat. No. 4,950,645 and PCT Patent Application WO 91/16347, are contemplated for use with cellular carriers and other embodiments of the present invention.

Another adjuvant contemplated for use in the present invention is BCG. BCG (bacillus Calmette-Guerin, an attenuated strain of Mycobacterium) and BCG-cell wall skeleton (CWS) may also be used as adjuvants in the invention, with or without trehalose dimycolate. Trehalose dimycolate may be used itself. Trehalose dimycolate administration has been shown to correlate with augmented resistance to influenza virus infection in mice (Azuma et al., 1988). Trehalose dimycolate may be prepared as described in U.S. Pat. No. 4,579,945.

BCG is an important clinical tool because of its immunostimulatory properties. BCG acts to stimulate the reticuloendothelial system, activates natural killer cells and increases proliferation of hematopoietic stem cells. Cell wall extracts of BCG have proven to have excellent immune adjuvant activity. Molecular genetic tools and methods for mycobacteria have provided the means to introduce foreign genes into BCG (Jacobs et al., 1987; Snapper et al., 1988; Husson et al., 1990; Martin et al., 1990).

Live BCG is an effective and safe vaccine used worldwide to prevent tuberculosis. BCG and other mycobacteria are highly effective adjuvants, and the immune response to mycobacteria has been studied extensively. With nearly 2 billion immunizations, BCG has a long record of safe use in man (Luelmo, 1982; Late et al., 1984). It is one of the few vaccines that can be given at birth, it engenders long-lived immune responses with only a single dose, and there is a worldwide distribution network with experience in BCG vaccination. An exemplary BCG vaccine is sold as TICE™ BCG (Organon Inc., West Orange, N.J.).

Amphipathic and surface active agents, e.g., saponin and derivatives such as QS21 (Cambridge Biotech), form yet another group of adjuvants for use with the immunogens of the present invention. Nonionic block copolymer surfactants (Rabinovich et al., 1994; Hunter et al., 1991) may also be employed. Oligonucleotides are another useful group of adjuvants (Yamamoto et al., 1988). Quil A and lentinen are other adjuvants that may be used in certain embodiments of the present invention.

One group of adjuvants preferred for use in the invention are the detoxified endotoxins, such as the refined detoxified endotoxin of U.S. Pat. No. 4,866,034. These refined detoxified endotoxins are effective in producing adjuvant responses in mammals. Of course, the detoxified endotoxins may be combined with other adjuvants to prepare multi-adjuvant-incorporated cells. For example, combination of detoxified endotoxins with trehalose dimycolate is particularly contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. Nos. 4,436,727, 4,436, 728 and 4,505,900. Combinations of just CWS and trehalose dimycolate, without detoxified endotoxins, is also envisioned to be useful, as described in U.S. Pat. No. 4,520,019.

In other embodiments, the present invention contemplates that a variety of adjuvants may be employed in the membranes of cells, resulting in an improved immunogenic composition. The only requirement is, generally, that the adjuvant be capable of incorporation into, physical association with, or conjugation to, the cell membrane of the cell in question. Those of skill in the art will know the different kinds of adjuvants that can be conjugated to cellular vaccines in accordance with this invention and these include alkyl lysophospholipids (ALP); BCG; and biotin (including biotinylated derivatives) among others. Certain adjuvants particularly contemplated for use are the teichoic acids from Gram-cells. These include the lipoteichoic acids (LTA), ribitol teichoic acids (RTA) and glycerol teichoic acid (GTA). Active forms of their synthetic counterparts may also be employed in connection with the invention (Takada et al., 1995a).

Various adjuvants, even those that are not commonly used in humans, may still be employed in animals, where, for example, one desires to raise antibodies or to subsequently obtain activated T cells. The toxicity or other adverse effects that may result from either the adjuvant or the cells, e.g., as may occur using non-irradiated tumor cells, is irrelevant in such circumstances.

One group of adjuvants preferred for use in some embodiments of the present invention are those that can be encoded by a nucleic acid (e.g., DNA or RNA). It is contemplated that such adjuvants may be encoded in a nucleic acid (e.g., an expression vector) encoding the antigen, or in a separate vector or other construct. These nucleic acids encoding the adjuvants can be delivered directly, such as for example with lipids or liposomes.

3. Excipients, Salts and Auxiliary Substances

An antigenic composition of the present invention may be mixed with one or more additional components (e.g., excipients, salts, etc.) which are pharmaceutically acceptable and compatible with at least one active ingredient (e.g., antigen). Suitable excipients are, for example, water, saline, dextrose, glycerol, ethanol and combinations thereof.

An antigenic composition of the present invention may be formulated into the vaccine as a neutral or salt form. A pharmaceutically-acceptable salt, includes the acid addition salts (formed with the free amino groups of the peptide) and those which are formed with inorganic acids such as, for example, hydrochloric or phosphoric acid, or such organic acids as acetic, oxalic, tartaric, mandelic, and the like. A salt formed with a free carboxyl group also may be derived from an inorganic base such as, for example, sodium, potassium, ammonium, calcium, or ferric hydroxide, and such organic bases as isopropylamine, trimethylamine, 2-ethylamino ethanol, histidine, procaine, and combinations thereof.

In addition, if desired, an antigenic composition may comprise minor amounts of one or more auxiliary substances such as for example wetting or emulsifying agents, pH buffering agents, etc. which enhance the effectiveness of the antigenic composition or vaccine.

F. Vaccine and Immunogenic Composition Preparations

Once produced, synthesized and/or purified, an antigen or other vaccine component may be prepared as a vaccine or immunogenic composition for administration to an individual. The preparation of a vaccine is generally well understood in the art, as exemplified by U.S. Pat. Nos. 4,608,251, 4,601,903, 4,599,231, 4,599,230, and 4,596,792, all incorporated herein by reference. Such methods may be used to prepare a vaccine comprising an antigenic composition comprising a particular RBD of SARS-CoV-2 as active ingredient(s), in light of the present disclosure. In particular embodiments, the compositions of the present invention are prepared to be pharmacologically acceptable vaccines.

Pharmaceutical vaccine or immunogenic compositions of the present invention comprise an effective amount of one or more certain RBDs of SARS-CoV-2 dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one RBD of SARS-CoV-2 will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

Examples of pharmaceutically acceptable carriers include any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). The modified RBD of SARS-CoV-2 may comprise different types of carriers depending on whether it is to be administered in solid, liquid or aerosol form, and whether it need to be sterile for such routes of administration as injection. Except insofar as any conventional carrier is incompatible with the active ingredient, its use in the therapeutic or pharmaceutical compositions is contemplated.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The modified RBD of SARS-CoV-2 may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present disclosure. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the RBD of SARS-CoV-2 is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof, a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof, a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein.

In particular embodiments, prolonged absorption of an injectable composition can be brought about by the use in the compositions of agents delaying absorption, such as, for example, aluminum monostearate, gelatin or combinations thereof.

G. Vaccine or Immunogenic Composition Administration

The manner of administration of a vaccine or immunogenic composition may be varied widely. Any of the conventional methods for administration of a vaccine or immunogenic composition are applicable. For example, a vaccine may be conventionally administered intravenously, intradermally, intraarterially, intraperitoneally, intralesionally, intracranially, intraarticularly, intraprostaticaly, intrapleurally, intratracheally, intranasally, intravitreally, intravaginally, intratumorally, intramuscularly, intraperitoneally, subcutaneously, intravesicularlly, mucosally, intrapericardially, orally, rectally, nasally, topically, in eye drops, locally, using aerosol, injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

A vaccination or immunogenic composition delivery schedule and dosages may be varied on a patient by patient basis, taking into account, for example, factors such as the weight and age of the patient, the type of disease being treated, the severity of the disease condition, previous or concurrent therapeutic interventions, the manner of administration and the like, which can be readily determined by one of ordinary skill in the art.

A vaccine or immunogenic composition may be administered in a manner compatible with the dosage formulation, and in such amount as will be therapeutically effective and immunogenic. For example, the intramuscular route may be preferred in the case of toxins with short half lives in vivo. The quantity to be administered depends on the subject to be treated, including, e.g., the capacity of the individual's immune system to synthesize antibodies, and the degree of protection desired. The dosage of the vaccine will depend on the route of administration and will vary according to the size of the host. Precise amounts of an active ingredient required to be administered depend on the judgment of the practitioner. In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein However, a suitable dosage range may be, for example, of the order of several hundred micrograms active ingredient per vaccination. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per vaccination, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. A suitable regime for initial administration and booster administrations (e.g., inoculations) are also variable, but are typified by an initial administration followed by subsequent inoculation(s) or other administration (s).

In many instances, it will be desirable to have multiple administrations of the vaccine or immunogenic composition, usually not exceeding six vaccinations, for example, more usually not exceeding four vaccinations and in some cases one or more, usually at least about three vaccinations. The vaccinations may be at from two to twelve week intervals, more usually from three to five week intervals, although longer intervals are encompassed herein. Periodic boosters at intervals of 1-5 years, usually three years, may be desirable to maintain protective levels of the antibodies.

The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays. Other immune assays can be performed and assays of protection from challenge with the RBD of SARS-CoV-2 can be performed, following immunization.

H. Kits of the Disclosure

Any of the compositions described herein may be comprised in a kit. In a non-limiting example, a modified RBD SARS-CoV-2 spike composition may be comprised in a kit. In a non-limiting example, an immunogenic composition comprising a modified RBD SARS-CoV-2 spike composition may be comprised in a kit. In a non-limiting example, a vaccine comprising a modified RBD SARS-CoV-2 spike composition may be comprised in a kit, including deglycosylated.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the composition and any other reagent containers in close confinement for commercial sale. Such containers may include injection or blow-molded plastic containers into which the desired vials are retained.

The component(s) of the kit may be provided as dried powder(s). When reagents and/or components are provided as a dry powder, the powder can be reconstituted by the addition of a suitable solvent. It is envisioned that the solvent may also be provided in another container means. The kits may comprise a container means for containing a sterile, pharmaceutically acceptable buffer and/or other diluent.

Irrespective of the number and/or type of containers, the kits of the invention may also comprise, and/or be packaged with, an instrument for assisting with the injection/administration and/or placement of the ultimate composition within the body of an animal. Such an instrument may be a syringe, pipette, forceps, and/or any such medically approved delivery vehicle. In some cases, there are one or more means to identify the presence of SARS in a sample from an individual.

The following numbered embodiments also form part of the present disclosure:

1. An immunogenic composition comprising the receptor-binding domain (RBD) of the Severe acute respiratory syndrome coronavirus (SARS-CoV-2) spike protein, and a carrier.
2. The composition of embodiment 1, wherein the domain is comprised within the full-length SARS-CoV-2 spike protein.
3. The composition of embodiment 1 or 2, wherein the domain is a fragment of the SARS-CoV-2 spike protein.
4. The composition of any one of embodiments 1-3, wherein the fragment comprises amino acid residues 333-528 of the SARS-CoV-2 spike protein.
5. The composition of any one of embodiments 1-4, wherein said amino acid sequence comprises SEQ ID NO: 3.
6. The composition of any one of embodiments 1-5, wherein said amino acid sequence comprises SEQ ID NO: 45.
7. The composition of any one of embodiments 1-6, wherein said amino acid sequence comprises SEQ ID NO: 4.
8. The composition of any one of embodiments 1-7, wherein said amino acid sequence is SEQ ID NO: 1.
9. The composition of any one of embodiments 1-8, wherein said amino acid sequence includes one or more of SEQ ID NOs: 5-42.
10. The composition of any one of embodiments 1-9, wherein said amino acid sequence includes one or more of SEQ ID NOs: 9, 13, 14, 16, 18, 20, 25, 27, 32, 35, 36, 37, 39, 40, and/or 42.
11. The composition of any one of embodiments 1-10, wherein said fragment comprises one or more amino acid substitutions so that said fragment is not naturally occurring.
12. The composition of any one of embodiments 1-11, wherein said substitution affects an N-glycosylation site.
13. The composition of any one of embodiments 1-12, wherein the site comprises an amino acid deletion.
14. The composition of any one of embodiments 1-13, wherein the site comprises an amino acid substitution.
15. A method of preventing or delaying the onset of SARS or of reducing at least one symptom of SARS in an animal, comprising the step of providing an effective amount of the composition of any one of embodiments 1-14 to the animal.
16. The method of embodiment 15, wherein the composition is provided to the individual once.
17. The method of embodiment 15, wherein the composition is provided to the individual more than once.
18. The method of embodiment 15, wherein the composition is provided subsequently to the individual within weeks, months, or years of the first providing step.
19. The method of any one of embodiments 15-18, wherein the individual displays one or more symptoms of SARS.
20. The method of any one of embodiments 15-18, wherein the individual lacks any symptoms of SARS.
21. The method of any one of embodiments 15-20, wherein the individual has been exposed to SARS.
22. The method of any one of embodiments 15-21, wherein the individual has come into contact with an individual that has SARS.
23. The method of any one of embodiments 15-22, wherein the individual is a child, an elderly person, exposed to a bioweapon or at risk thereof, is a member of the military, or is a health care worker.
24. A nucleic acid sequence encoding the RBD of bases 333-528 of SARS-CoV-2 spike protein operably linked to heterologous targeting, signaling, termination or promoter sequences.
25. The nucleic acid sequence of embodiment 24, wherein the domain is comprised within the full-length SARS-CoV-2 spike protein.
26. The nucleic acid sequence of embodiment 24 or 25, wherein the domain is a fragment of the SARS-CoV-2 spike protein.
27. The nucleic acid sequence of any one of embodiments 24-26, wherein said sequence encodes an amino acid sequence comprising SEQ ID NO: 3.
28. The nucleic acid sequence of any one of embodiments 24-27, wherein said sequence encodes an amino acid sequence comprising SEQ ID NO: 45.
29. The nucleic acid sequence of any one of embodiments 24-28, wherein said sequence encodes an amino acid sequence comprising SEQ ID NO: 4.
30. The nucleic acid sequence of any one of embodiments 24-29, wherein said sequence encodes the amino acid sequence of SEQ ID NO:1.
31. The nucleic acid sequence of any one of embodiments 24-30, wherein said sequence encodes an amino acid sequence comprising one or more of SEQ ID NOs: 9, 13, 14, 16, 18, 20, 25, 27, 32, 35, 36, 37, 39, 40, and/or 42.
32. The nucleic acid sequence of any one of embodiments 24-31, wherein said fragment comprises one or more amino acid substitutions so that said fragment is not naturally occurring.
33. The nucleic acid sequence of any one of embodiments 24-32, wherein said substitution affects an N-glycosylation site.
34. The nucleic acid sequence of any one of embodiments 24-33, wherein the site comprises an amino acid deletion.
35. The nucleic acid sequence of any one of embodiments 24-34, wherein the site comprises an amino acid substitution.
36. The nucleic acid sequence of any one of embodiments 24-35, wherein said sequence comprises SEQ ID NOs: 60, 61, or 62.
37. The nucleic acid sequence of any one of embodiments 24-36, wherein said sequence is SEQ ID NO: 59.

All publications, patents and patent applications identified herein are incorporated by reference, as though set forth herein in full. The invention being thus described, it will be apparent to those skilled in the art that the same may be varied in many ways without departing from the spirit and scope of the invention. Such variations are included within the scope of the following claims.

The invention is further illustrated by the following specific examples which are not intended in any way to limit the scope of the invention.

Example 1

Current Understanding of SARS-COV-2 and Comparison to SARS-CoV.

SARS-CoV-2 belongs to genus betacoronavirus of Coronaviridae family. Complete genome (~29,882 bases) of several isolates have now been sequenced. The virus is most closely related to a bat coronavirus RaTG13 strain that was isolated in Yunnan Province (sequence similarity of 96.3%)[4]. SARS-CoV-2 is also closely related to SARS-CoV (~80% identity), the virus that was responsible for the severe acute respiratory syndrome (SARS) outbreak in 2002-2003. Like SARS-CoV, SARS-CoV-2 has been reported to utilize ACE2 (angiotensin converting enzyme 2) as a receptor[4]. Spike (S) glycoprotein that binds ACE2 is 76% identical between the two viruses. As such, many biochemical, structural, functional and immunological properties of the S protein are expected to be similar. SARS-CoV S protein is highly glycosylated with 18 N-linked glycosylation sites. Glycans account for ~98 kDa[5], and they play important roles in protein stability or folding during biogenesis and in immune evasion via epitope masking.

Figure 1B:
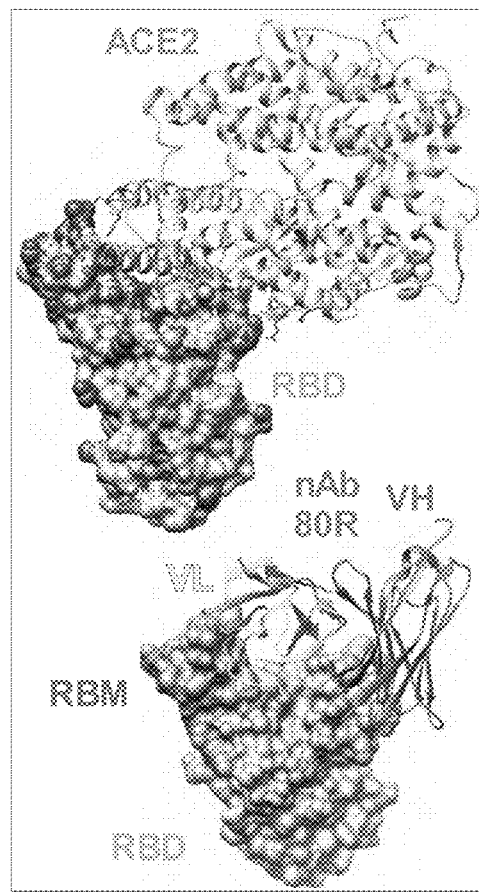

Cryo-EM structures of trimeric SARS-CoV S glycoprotein have been determined (FIG. 1A)[6]. Also, X-ray crystal structures of the receptor binding domain (RBD) of the S protein together with ACE2[7] as well as a number of neutralizing antibodies (nAbs) have also been determined[5,8-10] (FIG. 1B). Although nAbs against SARS-CoV are known to bind different regions of the S protein[11], nAb 80R binds directly at the receptor binding motif (RBM) and it is shown to be highly potent with nanomolar affinity[9].

Progress Towards Vaccine Development Against SARS-CoV

Considering many similarities between SARS-CoV and SARS-CoV-2, some of what the field has learned from efforts to develop a vaccine against SARS-CoV could be adopted for developing a SARS-CoV-2 vaccine. Since the emergence of the SARS-CoV in 2002, various strategies have been explored to develop a vaccine against the virus. They include inactivated virus[12-17], live-attenuated virus[18], DNA[19-22], and viral vector vaccines[23]. Overall, results from these studies showed limited success. In general, vaccines based on the RBD of S protein induced higher nAb titers and resulted in more consistent protection against virus challenges. Different RBD-based immunogens (either alone[24] or fused to IgG Fc[13]) have been produced in various recombinant protein expression systems, including E. coli, mammalian cell lines (293T, CHO), insect cells (Sf9) and yeast[24-26]. Their immunogenic properties have been evaluated in different animal models (mice, rabbits and macaques) using different adjuvants (Freund's adjuvant, Alum, MF59, Sigma Adjuvant System, etc.) and immunization routes (intramuscular, intradermal, intranasal, subcutaneous). To summarize a large body of work, it has been demonstrated that (1) RBD can sufficiently induce nAbs; (2) RBD expressed in 293T cells elicited significantly higher nAbs than RBD expressed in Sf9 or E. coli[24]; and (3) RBD-based vaccine can induce long-term neutralizing activity and protective immunity[27]. Importantly, it has been shown that potent and persistent antibody responses against the RBD exist in recovered patients[25]. Thus, nAbs against RBD have been clearly established as immune correlates of protection. Advantages of RBD-based vaccines, over the use of the entire S protein, have been discussed in a latest review article[28].

Based on facts that there are many safety concerns and regulatory hurdles for using inactivated or live-attenuated virus vaccines as well as for viral vector vaccines, and that RBD-based subunit vaccines have demonstrated their potential, we believe the best pathway to develop a vaccine against SARS-CoV/-2 is to optimize RBD-based antigens. Unfortunately, SARS-CoV vaccine development efforts have not progressed significantly beyond the pre-clinical stage. We are aware of only two published reports of Phase I clinical vaccine trials: One with inactivated virus vaccine conducted in China[29], and one DNA vaccine conducted in the U.S.[30]. No follow up Phase II trials were conducted. It is not clear whether this is due to safety concerns, poor efficacy, lack of political will and/or insufficient financial incentive. Had there been continued efforts, the current epidemic with SARS-CoV-2 could have been avoided or minimized (assuming some cross-reactivity of nAbs). Regardless, much work is needed to advance vaccine development against SARS-CoV/-2.

Progress Towards Vaccine Development Against SARS-CoV-2

Figure 2:
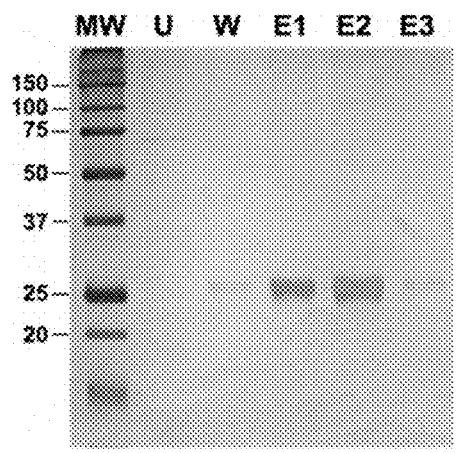

Based on our assessment of the progress made towards developing a SARS-CoV vaccine, we believe developing a subunit protein vaccine based on the RBD would be the best choice for SARS-CoV-2 from both safety and efficacy points of views. Towards this goal, we have successfully designed, constructed, expressed and purified SARS-CoV-2 RBD from 293F cells (FIG. 2). A plasmid with the DNA encoding the vaccine candidate was prepared, amplified and purified from E. coli and 293F cells were transfected. Protein was expressed for 5 days and purified from cell culture supernatant. We started mouse immunization study. Antisera will be collected later and evaluated for neutralizing activity.

The amino acids are shown below with features coded as indicated.

Signal Peptide (Italics) (This can be any signal peptide)
Linker (BOLD)
SARS-CoV-2 RBD (underlined) Bases 333-528 Severe acute respiratory syndrome coronavirus 2 spike protein Gen Bank QHU79173.1
Linker (BOLD)
6×his Tag (italics, bold)

SEQ ID NO: 1

*MGILPSPGMPALLSLVSLLSVLLMGCVAE*KLTGGT<u>TNLCPFGEVFNATRFASVYAW</u>

<u>NRKRISNCVADYSVLYNSASFSTFKCYGVSPTKLNDLCFTNVYADSFVIRGDEVRQ</u>

<u>IAPGQTGKIADYNYKLPDDFTGCVIAWNSNNLDSKVGGNYNYLYRLFRKSNLKPF</u>

<u>ERDISTEIYQAGSTPCNGVEGFNCYFPLQSYGFQPTNGVGYQPYRVVVLSFELLHA</u>

<u>PATVCGPK</u>GPGM*HHHHHH*

SEQ ID NO: 2
Surface glycoprotein [Severe acute respiratory syndrome coronavirus 2]
GenBank: QHU79173.1

```
  1 mfvflvllpl vssqcvnltt rxxxxxxxxx xxxxxxxxxx xxxxxxxxxs tqdlflpffs 61 nvtwfhaihv sgtngtkrfd npvlpfndgv yfasteksni irgwifgttl dsktqslliv 121 nnatnvvikv cefqfcndpf lgvyyhknnk swmesefrvy ssannctfey vsqpflmdle 181 gkqgnfknlr efvfknidgy fkiyskhtpi nlvrdlpqgf saleplvdlp iginitrfqt
```

```
241 llalhrsylt pgdsssgwta gaaayyvgyl qprtfllkyn engtitdavd caldplsetk 301 ctlksftvek giyqtsnfrv qptesivrfp ni<u>tnlcpfge vfnatrfasv yawnrkrisn</u>

361 <u>cvadysvlyn sasfstfkcy gvsptklndl cftnvyadsf virgdevrqi apgqtgkiad</u>

421 <u>vnvklpddft gcviawnsnn ldskvggnyn ylyrlfrksn lkpferdist eiyqagstpc</u>

481 <u>ngvegfncyf plqsygfqpt ngvgyqpyrv vvlsf

14. Takasuka, N., Fujii, H., Takahashi, Y., Kasai, M., Morikawa, S., Itamura, S., Ishii, K., Sakaguchi, M., Ohnishi, K., Ohshima, M., Hashimoto, S., Odagiri, T., Tashiro, M., Yoshikura, H., Takemori, T. & Tsunetsugu-Yokota, Y. A subcutaneously injected UV-inactivated SARS coronavirus vaccine elicits systemic humoral immunity in mice. *Int Immunol* 16, 1423-1430, doi:10.1093/intimm/dxh143 (2004).

15. Tang, L., Zhu, Q., Qin, E., Yu, M., Ding, Z., Shi, H., Cheng, X., Wang, C., Chang, G., Zhu, Q., Fang, F., Chang, H., Li, S., Zhang, X., Chen, X., Yu, J., Wang, J. & Chen, Z. Inactivated SARS-CoV-2 vaccine prepared from whole virus induces a high level of neutralizing antibodies in BALB/c mice. *DNA Cell Biol* 23, 391-394, doi:10.1089/104454904323145272 (2004).

16. Qu, D., Zheng, B., Yao, X., Guan, Y., Yuan, Z. H., Zhong, N. S., Lu, L. W., Xie, J. P. & Wen, Y. M. Intranasal immunization with inactivated SARS-CoV-2 (SARS-associated coronavirus) induced local and serum antibodies in mice. *Vaccine* 23, 924-931, doi:10.1016/j.vaccine.2004.07.031 (2005).

17. Zhang, C. H., Lu, J. H., Wang, Y. F., Zheng, H. Y., Xiong, S., Zhang, M. Y., Liu, X. J., Li, J. X., Wan, Z. Y., Yan, X. G., Qi, S. Y., Cui, Z. & Zhang, B. Immune responses in Balb/c mice induced by a candidate SARS-CoV-2 inactivated vaccine prepared from F69 strain. *Vaccine* 23, 3196-3201, doi:10.1016/j.vaccine.2004.11.073 (2005).

18. Lamirande, E. W., DeDiego, M. L., Roberts, A., Jackson, J. P., Alvarez, E., Sheahan, T., Shieh, W. J., Zaki, S. R., Baric, R., Enjuanes, L. & Subbarao, K. A live attenuated severe acute respiratory syndrome coronavirus is immunogenic and efficacious in golden Syrian hamsters. *J Virol* 82, 7721-7724, doi:10.1128/JVI.00304-08 (2008).

19. Yang, Z. Y., Kong, W. P., Huang, Y., Roberts, A., Murphy, B. R., Subbarao, K. & Nabel, G. J. A DNA vaccine induces SARS coronavirus neutralization and protective immunity in mice. *Nature* 428, 561-564, doi:10.1038/nature02463 (2004).

20. Zeng, F., Chow, K. Y., Hon, C. C., Law, K. M., Yip, C. W., Chan, K. H., Peiris, J. S. & Leung, F. C. Characterization of humoral responses in mice immunized with plasmid DNAs encoding SARS-CoV-2 spike gene fragments. *Biochem Biophys Res Commun* 315, 1134-1139, doi:10.1016/j.bbrc.2004.01.166 (2004).

21. Zakhartchouk, A. N., Viswanathan, S., Moshynskyy, I., Petric, M. & Babiuk, L. A. Optimization of a DNA vaccine against SARS. *DNA Cell Biol* 26, 721-726, doi:10.1089/dna.2007.0616 (2007).

22. Callendret, B., Lorin, V., Charneau, P., Marianneau, P., Contamin, H., Betton, J. M., van der Werf, S. & Escriou, N. Heterologous viral RNA export elements improve expression of severe acute respiratory syndrome (SARS) coronavirus spike protein and protective efficacy of DNA vaccines against SARS. *Virology* 363, 288-302, doi:10.1016/j.virol.2007.01.012 (2007).

23. Bisht, H., Roberts, A., Vogel, L., Bukreyev, A., Collins, P. L., Murphy, B. R., Subbarao, K. & Moss, B. Severe acute respiratory syndrome coronavirus spike protein expressed by attenuated vaccinia virus protectively immunizes mice. *Proc Natl Acad Sci USA* 101, 6641-6646, doi:10.1073/pnas.0401939101 (2004).

24. Du, L., Zhao, G., Li, L., He, Y., Zhou, Y., Zheng, B. J. & Jiang, S. Antigenicity and immunogenicity of SARS-CoV-2 S protein receptor-binding domain stably expressed in CHO cells. *Biochem Biophys Res Commun* 384, 486-490, doi:10.1016/j.bbrc.2009.05.003 (2009).

25. Cao, Z., Liu, L., Du, L., Zhang, C., Jiang, S., Li, T. & He, Y. Potent and persistent antibody responses against the receptor-binding domain of SARS-CoV-2 spike protein in recovered patients. *Virol J* 7, 299, doi:10.1186/1743-422X-7-299 (2010).

26. Chen, W. H., Du, L., Chag, S. M., Ma, C., Tricoche, N., Tao, X., Seid, C. A., Hudspeth, E. M., Lustigman, S., Tseng, C. T., Bottazzi, M. E., Hotez, P. J., Zhan, B. & Jiang, S. Yeast-expressed recombinant protein of the receptor-binding domain in SARS-CoV-2 spike protein with deglycosylated forms as a SARS vaccine candidate. *Hum Vaccin Immunother* 10, 648-658, doi:10.4161/hv.27464 (2014).

27. Du, L., Zhao, G., He, Y., Guo, Y., Zheng, B. J., Jiang, S. & Zhou, Y. Receptor-binding domain of SARS-CoV-2 spike protein induces long-term protective immunity in an animal model. *Vaccine* 25, 2832-2838, doi:10.1016/j.vaccine.2006.10.031 (2007).

28. Zhu, X., Liu, Q., Du, L., Lu, L. & Jiang, S. Receptor-binding domain as a target for developing SARS vaccines. *J Thorac Dis* 5 Suppl 2, S142-148, doi:10.3978/j.issn.2072-1439.2013.06.06 (2013).

29. Lin, J. T., Zhang, J. S., Su, N., Xu, J. G., Wang, N., Chen, J. T., Chen, X., Liu, Y. X., Gao, H., Jia, Y. P. et al. Safety and immunogenicity from a phase I trial of inactivated severe acute respiratory syndrome coronavirus vaccine. *Antivir Ther* 12, 1107-1113 (2007).

30. Martin, J. E., Louder, M. K., Holman, L. A., Gordon, I. J., Enama, M. E., Larkin, B. D., Andrews, C. A., Vogel, L., Koup, R. A., Roederer, M., Bailer, R. T., Gomez, P. L., Nason, M., Mascola, J. R., Nabel, G. J., Graham, B. S. & Team, V. R. C. S. A SARS DNA vaccine induces neutralizing antibody and cellular immune responses in healthy adults in a Phase I clinical trial. *Vaccine* 26, 6338-6343, doi:10.1016/j.vaccine.2008.09.026 (2008).

Example 2

The receptor binding domain (RBD) of SARS-CoV-2 spike glycoprotein is able to induce potent, durable neutralizing antibody responses against the virus.

Abstract

A novel betacoronavirus (SARS-CoV-2) that causes severe pneumonia emerged through zoonosis in late 2019. The disease, referred to as COVID-19, has an alarming mortality rate and it is having a devastating effect on the global economy and public health systems. A safe, effective vaccine is urgently needed to halt this pandemic. In this study, immunogenicity of the receptor binding domain (RBD) of spike (S) glycoprotein was examined in mice. Animals were immunized with recombinant RBD antigen intraperitoneally using three different adjuvants (Zn-chitosan, Alhydrogel and Adju-Phos), and antibody responses were followed for over five months. Results showed that potent neutralizing antibodies (nAbs) can be induced with 70% neutralization titer ($NT_{70}$) of ~14,580 against live, infectious viruses. Although antigen-binding antibody titers decreased gradually over time, sufficiently protective levels of nAbs persisted ($NT_{50}$~7,290) over the five-month observation period. Results also showed that adjuvants have profound effects on kinetics of nAb induction, total antibody titers, antibody avidity, antibody longevity and B-cell epitopes targeted by the immune system. In conclusion, a recombinant subunit protein immunogen based on the RBD is a highly promising vaccine candidate. Continued evaluation of RBD immunogenicity using different adjuvants and vaccine regimens could further improve vaccine efficacy.

Introduction

In late 2019, an outbreak of severe pneumonia (referred to as COVID-19) began in China. The causative pathogen was identified as a novel coronavirus (CoV) designated as SARS-CoV-2 (a.k.a. 2019-nCoV). The virus infection resulted in high incidents of fatal pneumonia with clinical symptoms resembling those of SARS-CoV infections during the 2002-03 epidemic. They include persistent fever, chills/rigor, myalgia, malaise, dry cough, headache and dyspnoea (1). SARS-CoV-2 is believed to have emerged through zoonosis, but the virus is transmitted efficiently from human to human, even prior to onset of symptoms (2), via droplets/aerosol from coughing or sneezing, or direct contact. Consequently, the virus has been able to spread rapidly. In March of 2020, the World Health Organization (WHO) officially declared COVID-19 as a pandemic. As of mid-November, over 55.6 million confirmed cases with nearly 1.34 million deaths have been reported in 190 countries (3). The pandemic is having a devastating impact on the global economy and public health systems worldwide. Therefore, a safe and highly protective vaccine is urgently needed.

SARS-CoV-2 belongs to genus *betacoronavirus* of Coronaviridae family. Its single strand RNA genome ranges from 29,825 to 29,902 bases long. The virus is most closely related to a bat coronavirus RaTG13 strain (nucleotide sequence identity of ~96%)(4). SARS-CoV-2 is more distantly related to SARS-CoV (82% identity). However, both viruses utilize angiotensin converting enzyme 2 (ACE2) as a receptor (4). Binding of ACE2 and cellular entry is mediated by spike (S) glycoprotein, which is 1273 amino acids long. S proteins of the two viruses are 76% identical.

Cryo-EM structures of SARS-CoV-2 S protein as well as cocrystal structures of the receptor binding domain (RBD) of the protein bound to ACE2 have been solved (5-8). S protein functions as a homotrimer (FIG. 3A) and it is highly glycosylated. Glycosylation of all 22 potential N-linked glycosylation sites have been confirmed for SARS-CoV-2 (9). The RBD folds independently into a globular structure away from the rest of the S protein (FIG. 3B). It exists in two different conformations on the trimer: "open" and "closed" states (FIG. 3A). While it is in the "open" state, it can bind ACE2. Cocrystal structures of the RBD and ACE2 clearly identify amino acid residues on both proteins critical for binding (FIGS. 3C, 3D and 3E). Within the RBD, binding of ACE2 is mediated mostly by amino acid residues within a short linear segment called the receptor binding motif (RBM) (FIGS. 3D and 3E).

Many studies have shown that subunit protein antigens based on the RBD can elicit neutralizing antibodies (nAbs) against SARS-CoV (10-13). In this study, we examined immunogenicity of a SARS-CoV-2 recombinant RBD subunit protein vaccine candidate produced in 293F human cells in mice using three different adjuvants. We focused on the humoral immune responses since nAbs are considered to be the major immune correlates of protection. In particular, we monitored on the potency, induction kinetics and durability of nAb responses. The results indicate that potent, long-lasting nAbs can be induced using the RBD, that adjuvants can profoundly affect antibody responses, and that RBD-based subunit protein is a highly promising vaccine candidate against COVID-19.

Results

Immunogen Design, Production and Characterization

Figure 3F:
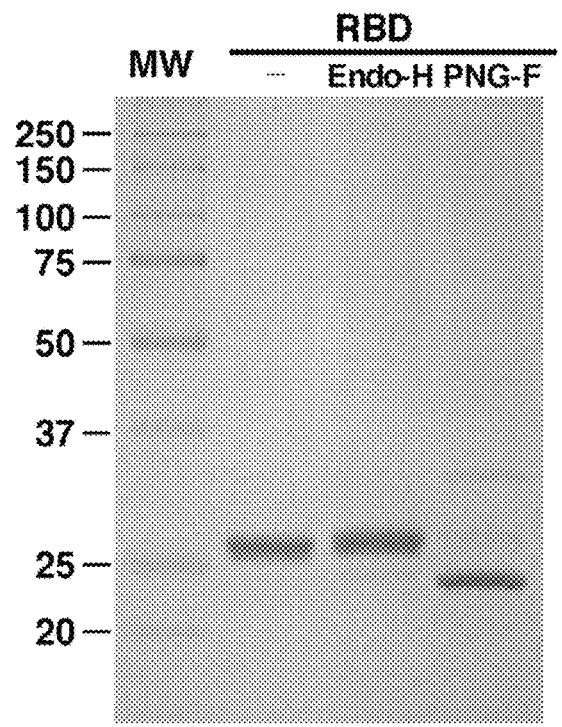
Figure 3G:
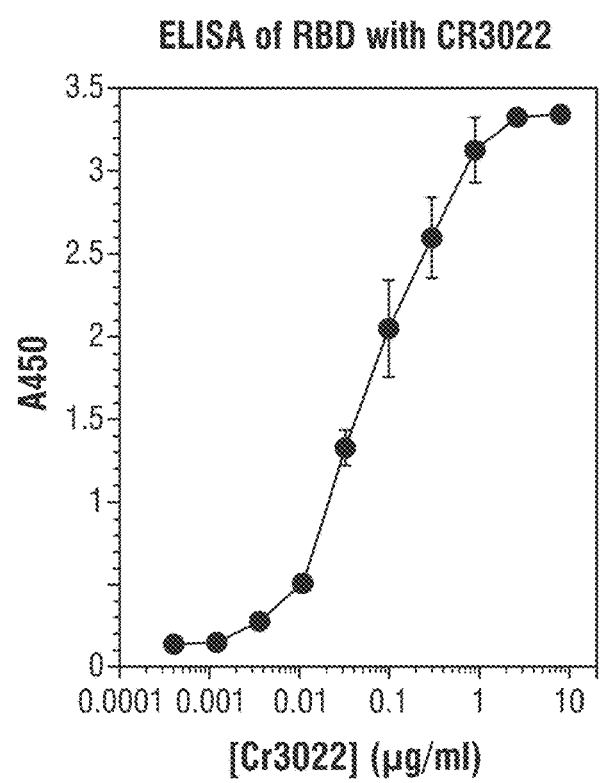

The RBD contains a single N-linked glycosylation site at $N^{343}$. To generate an RBD immunogen that is as native as possible, we constructed a plasmid encoding the RBD to be expressed in mammalian cells. The immunogen encompasses amino acids from $T^{333}$ to $K^{528}$, which are located three residues upstream or downstream of two cysteine residues, $C^{336}$ and $C^{525}$, respectively, that form a disulfide bridge and structurally define the RBD. The RBD gene is preceded by a signal peptide for secretion and followed by a hexahistidine tag (6×H) for purification. The recombinant RBD protein was transiently expressed efficiently in HEK 293F cells and purified easily from cell culture supernatant through a single-step Ni-NTA affinity chromatography (FIG. 3F). The protein migrated slower than the expected molecular weight of ~24 kD, indicating possible glycosylation. Indeed, treating the protein with PNGase F increased mobility. The protein was largely resistant to endoglycosidase H, suggesting that protein is likely glycosylated with mostly complex sugars, rather than high mannose. Correct folding of the RBD was confirmed by demonstrating its reactivity to a mAb CR3022 (14, 15) (FIG. 3G). A cocrystal structure of CR3022 bound to SARS-CoV-2 RBD (16) and its neutralizing activity against the virus (17) have been reported.

Antibody Responses Against the RBD in Mice

Figure 4A:
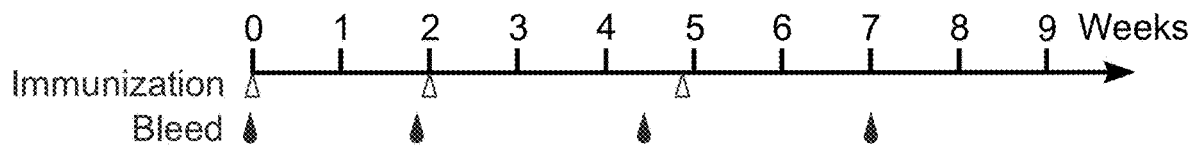

To evaluate immunogenicity of the RBD, 5-6 weeks old mice were immunized intraperitoneally three times on weeks 0, 2 and ~5. Animals were bled before and about 2 weeks after each immunization (FIG. 4A). Five groups of mice (4 or 5 mice per group) were immunized: (1) PBS (mock immunization control), (2) RBD only without an adjuvant, (3) RBD formulated with Alhydrogel (aluminum hydroxide; ALH), (4) RBD with Adju-Phos (aluminum phosphate; ADP), and (5) RBD with Zn-chitosan (CHT). Chitosan is a biodegradable, cationic polysaccharide derived from chitin by partial acetylation. Although it is not FDA-approved for human use, we included it for comparison because we have used it extensively as an experimental adjuvant (18-20).

Figure 4B:
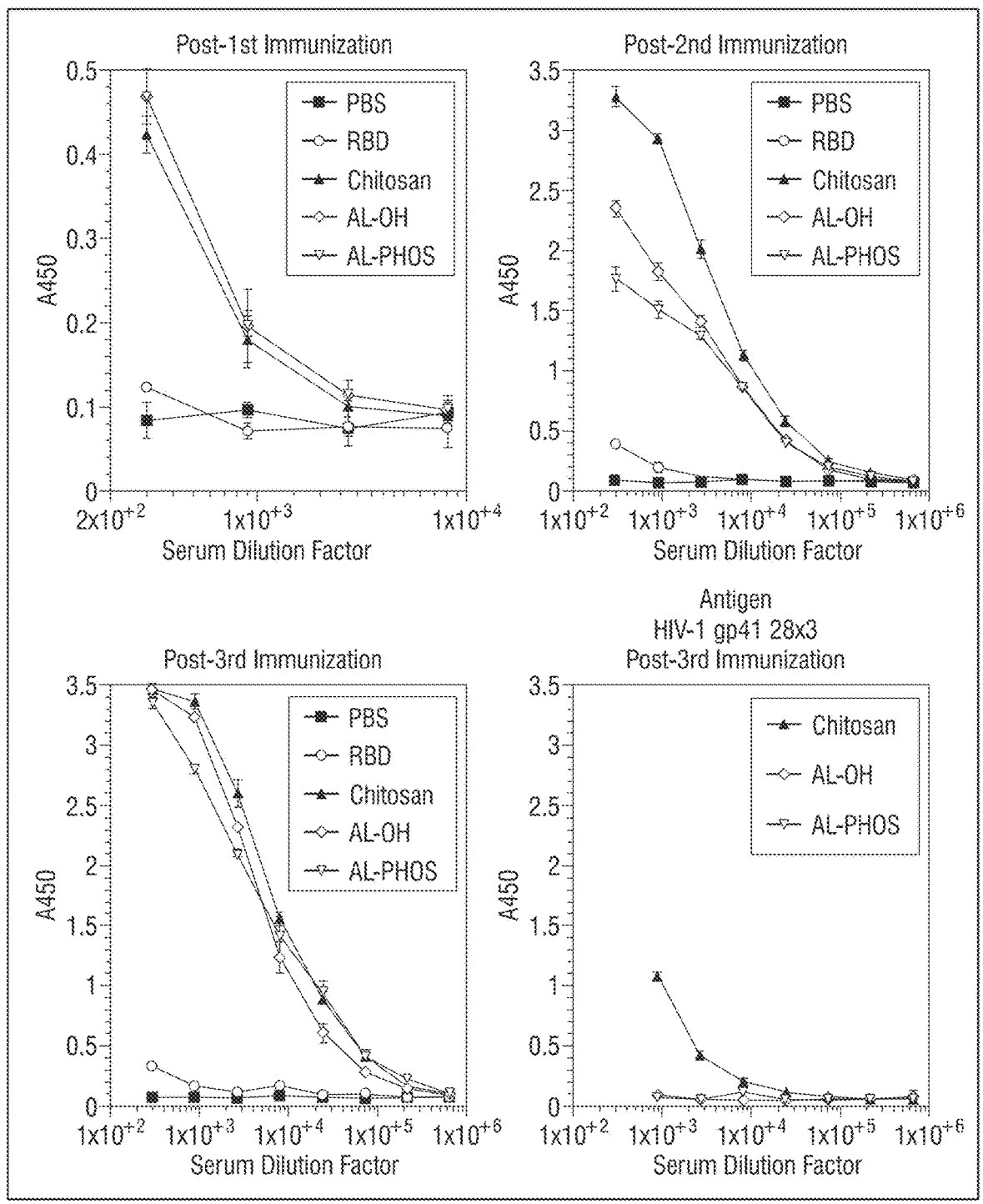
Figure 4C:
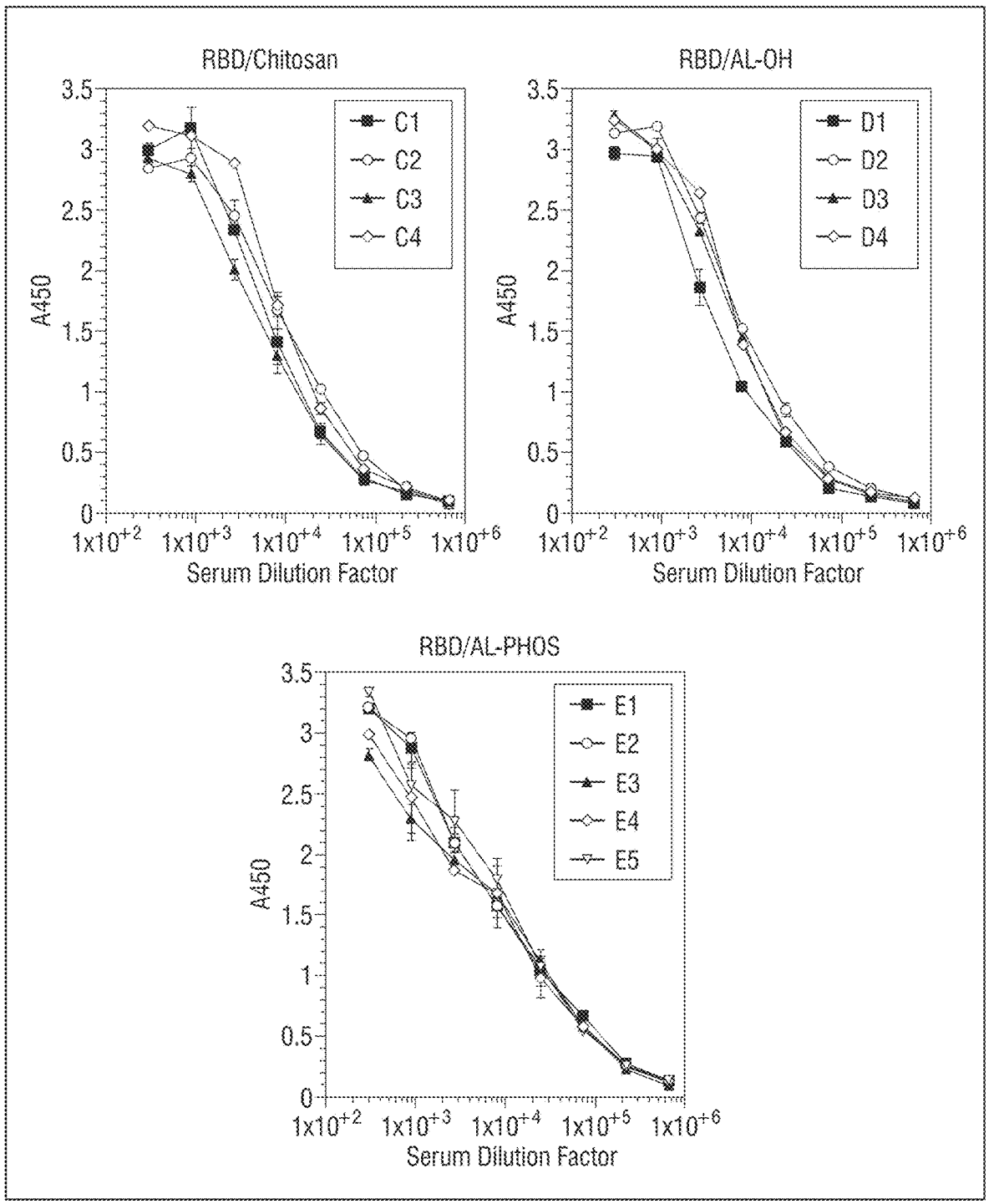

To examine anti-RBD antibody responses, ELISA was done using pooled sera from each group after each immunization (FIG. 4B). After the first immunization with 30 μg, all three groups of mice immunized with adjuvants mounted similar antibody responses with end-point titers of ~3,000. No antigen-specific antibodies were detected in mice immunized without an adjuvant. As expected, robust anamnestic responses were observed after the second immunization with 20 μg (end-point titers of ~2×10$^5$). The antibody response was particularly stronger in mice immunized with RBD adjuvanted with Zn-chitosan. Antibody response was barely detected in mice immunized without any adjuvant. After the third immunization (20 μg), all vaccine groups immunized with adjuvant elicited similar antibody titer of ~6×10$^5$. Even after three immunizations, antibody responses were barely detectable in the RBD group without an adjuvant. To assess possible animal-to-animal variations in antibody responses, ELISA was also done using serum samples from individual animals collected about two weeks after the third immunization (FIG. 4C). Results showed that there were no major differences in antibody levels between animals within each group.

Assessment of Virus Neutralizing Activity

Figure 5A:
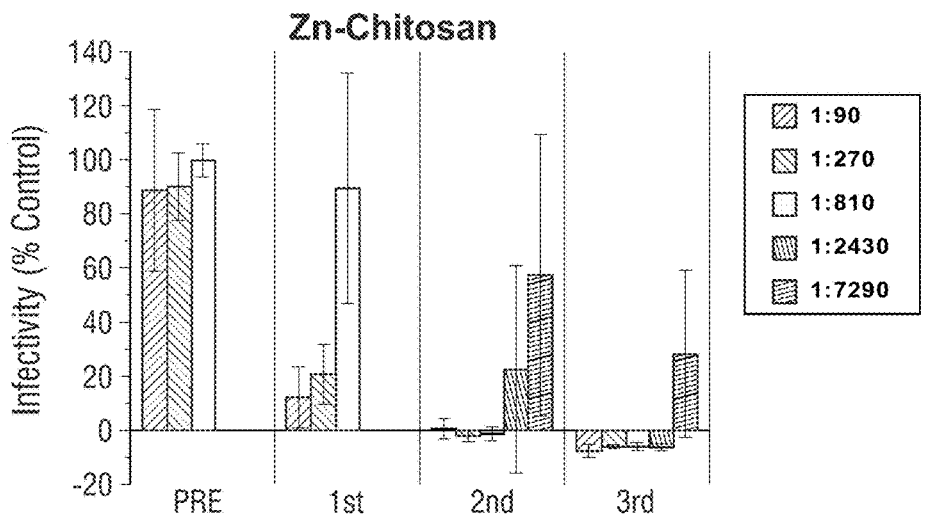
Figure 5B:
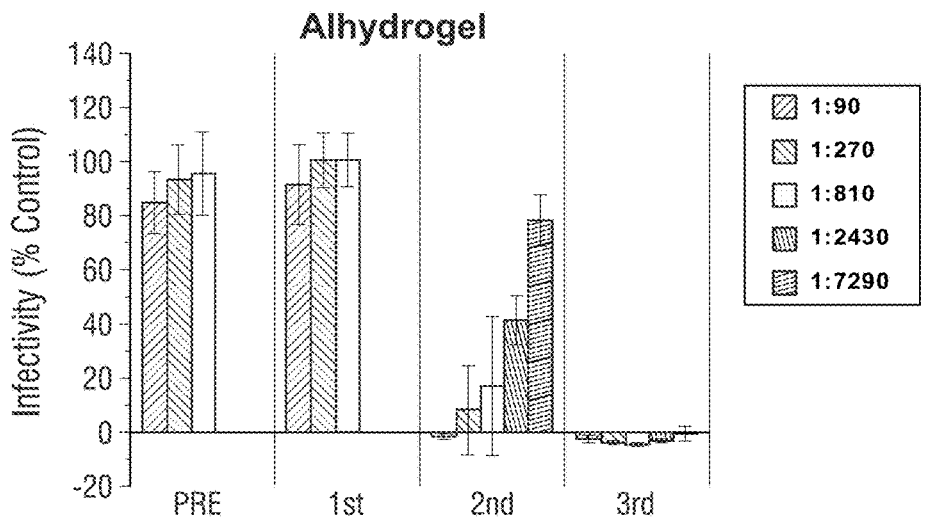
Figure 5C:
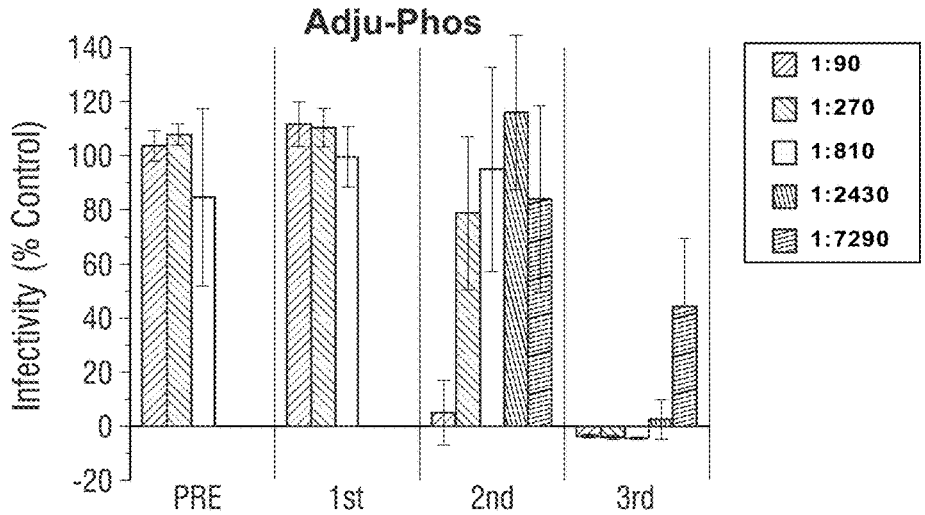

Neutralizing antibodies are the major immune correlates of protection against viral diseases. Virus neutralizing activity of antibodies was measured against 50 plaque forming units (50 PFU) of live, infectious SARS-CoV-2 in Vero E6 cells. This was done by monitoring cellular cytotoxicity microscopically and by quantifying release of lactate dehydrogenase (LDH) into cell culture medium. Comparison of neutralizing activity of three vaccine groups with different adjuvants is shown in FIG. 5A. Overall, Zn-chitosan group exhibited the best neutralizing activity, followed by Alhydrogel group and then Adju-Phos group. After the first immunization, 80% neutralization titer ($NT_{80}$) was ~270 for the Zn-chitosan group (FIG. 5A), which is higher than average neutralization titers observed in convalescent sera (~160) (21, 22). No neutralizing activity was observed in either Alhydrogel or Adju-Phos group (FIGS. 5B and 5C, respectively). After the second immunization, neutralizing activity increased nearly ten-fold to $NT_{80}$ of ~2,430 for the Zn-chitosan group. $NT_{80}$ in Alhydrogel group was ~810 while $NT_{80}$ was between 90 and 270 for Adju-Phos group. The neutralizing activity correlated well with RBD-binding antibody titers (FIG. 4B). After the third immunization, all three groups mounted strong nAb responses with $NT_{100}$ of at least 7,290 in Alhydrogel the group. It should be noted, however, that both RBD-binding antibodies (FIG. 4B) and nAbs (FIG. 5A) did not increase significantly after the third immunization for the Zn-chitosan group, compared to the second. We suspect this is most likely due to the presence of high level of preexisting antibodies at the time of third immunization in this group, which may have diminished the amount of antigens available for stimulating memory B cells, similar to maternal antibody inhibition of vaccine efficacy.

Figure 5D:
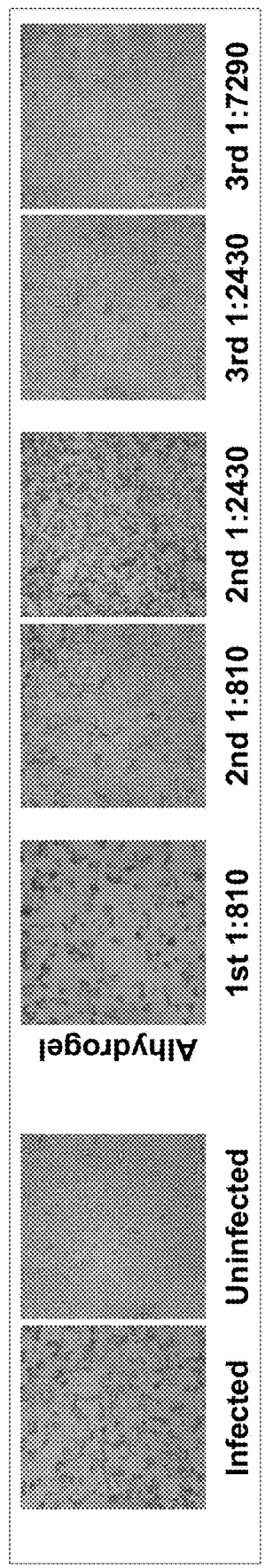

Microscopic observations paralleled the neutralizing activity assessed by the LDH assay. As examples, photomicrographic images of cell cultures uninfected or infected cells in the absence or presence of various dilutions of sera after one, two or three immunizations from the Alhydrogel group are shown in FIG. 5D.

Figure 6A:
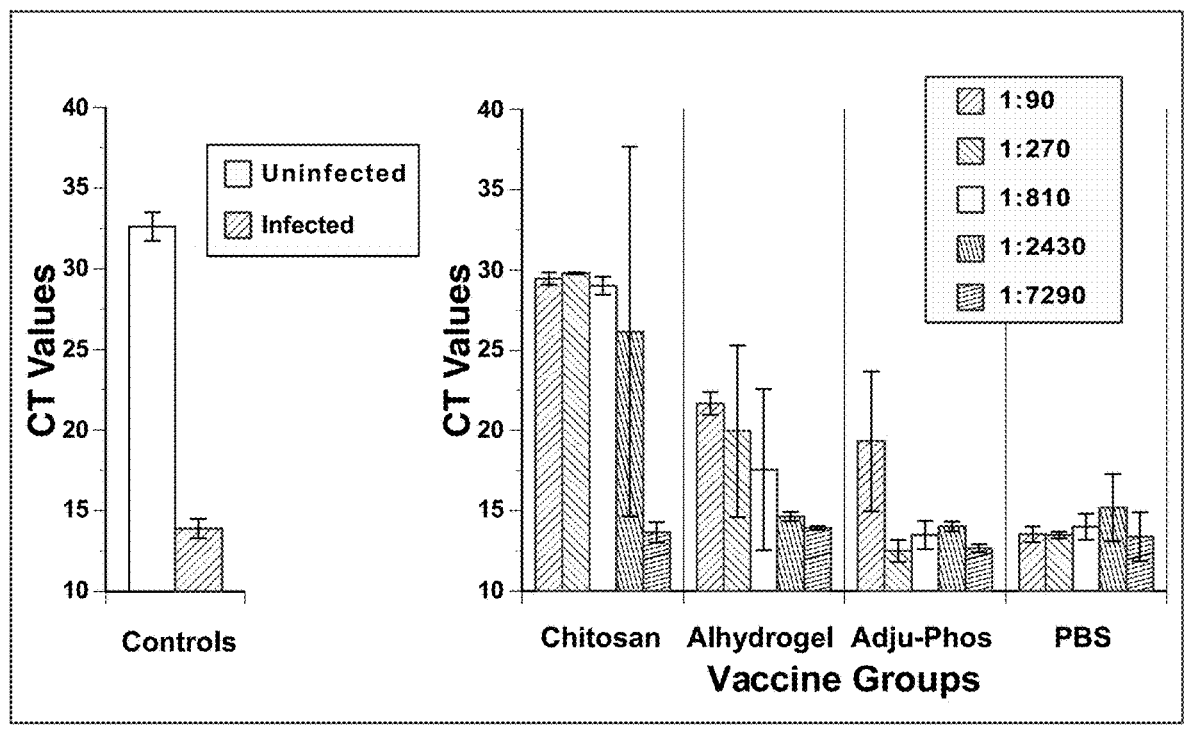

To validate neutralization assay results using the LDH cytotoxic assay, cell culture media from the assay were analyzed in parallel by quantitative RT-PCR. Results of the analyses using samples after the $2^{nd}$ immunization are shown in FIG. 6A. Cycle threshold (CT) values for samples from infected and uninfected cells were 13.9 and 32.6, respectively. CT values for samples from mock-immunized PBS group ranged between 13.4 and 15.2, indicating no inhibition of virus replication. As expected, results from the RT-PCR assay correlated very well with those of LDH cytotoxic assay. The rank order of neutralizing activity was Zn-chitosan>Alhydrogel>Adju-Phos. Complete neutralization of viruses at 1:90, 1:270 and 1:810 dilutions for Zn-chitosan group was confirmed by RT-PCR analysis. Slightly lower CT values for these samples (29.5, 29.8 and 29.0, respectively) compared to uninfected sample (32.6) likely represent presence of non-infectious viruses from the inoculum.

Figure 6B:
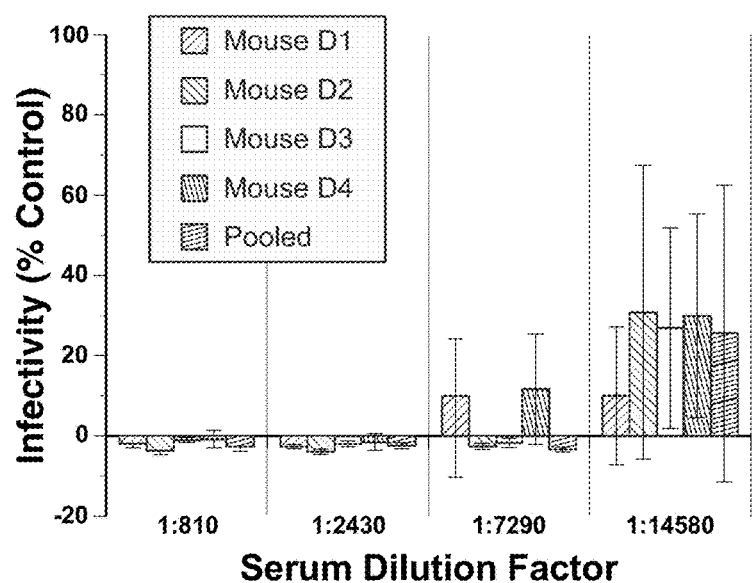

As shown in FIG. 5B, mice in the Alhydrogel group induced $NT_{100}$ of at least 7,290. Although this was achieved after three immunizations, this is highly significant because the adjuvant is already FDA-approved for human use. To quantify nAb levels more precisely, neutralization assays were repeated for this group with more diluted antisera from individual mouse. As shown in FIG. 6B, all mice mounted NT70 of ~14,580. One mouse showed $NT_{50}$ of ~29,160.

Durability of Antibody Responses

Figure 7A:
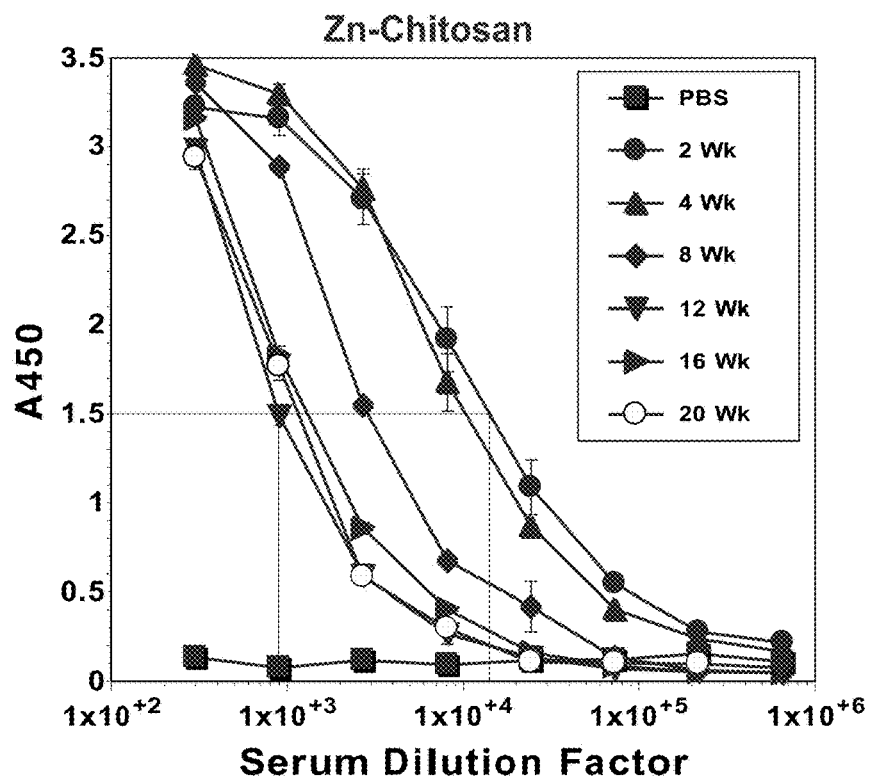
Figure 7B:
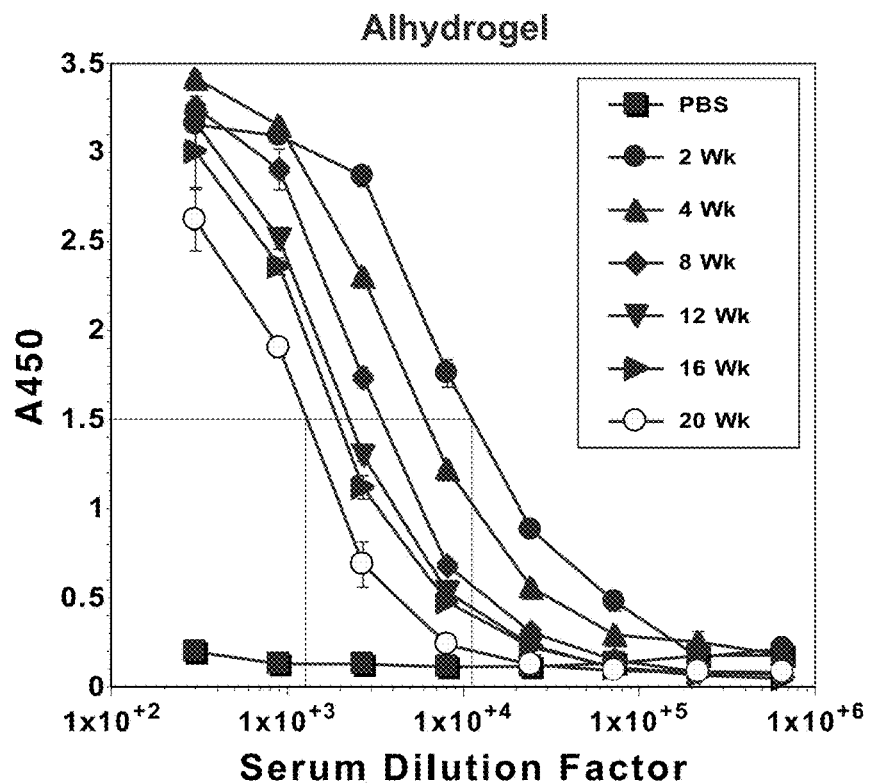
Figure 7C:
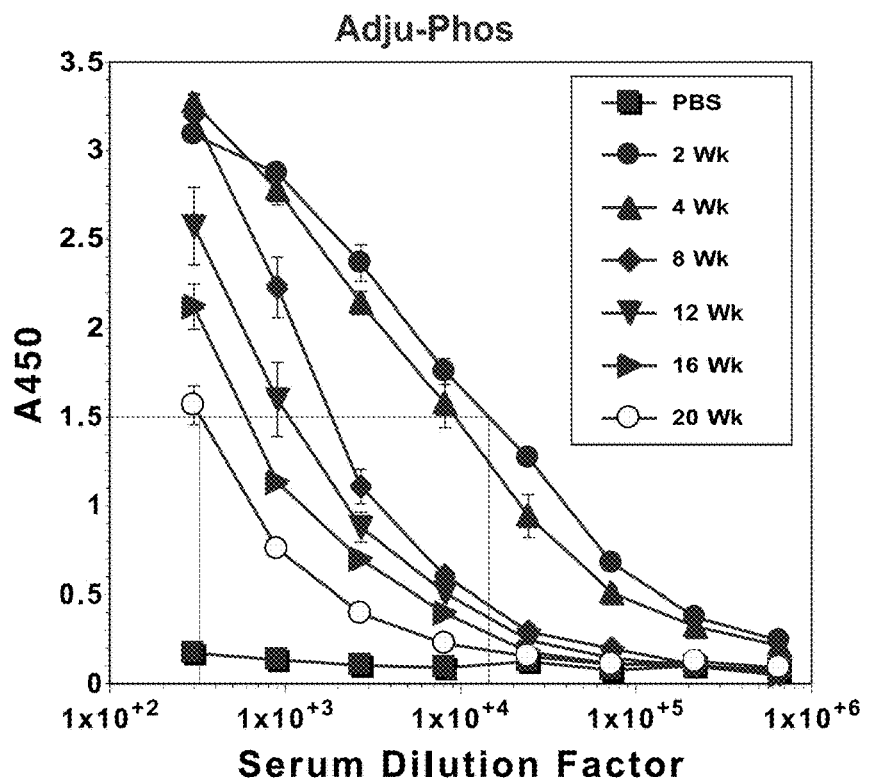
Figure 8A:
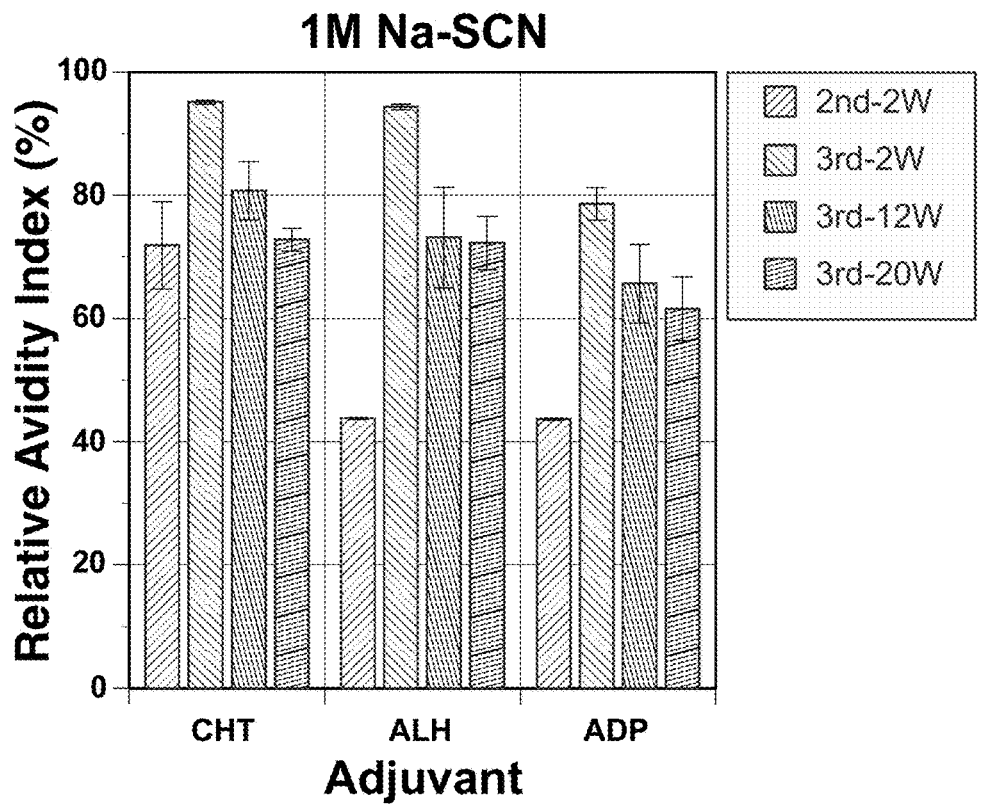

One of the important factors for determining vaccine efficacy is the longevity of protection after vaccination. As such, we examined durability of antibody levels against the RBD. Serum samples were collected from mice every two or four weeks after the third immunization for five months and evaluated by ELISA and virus neutralization assays. For the Zn-chitosan group, antibody levels decreased during the first 3 months (~14-fold from 2 weeks to 12 weeks) but stabilized afterwards (FIG. 8A). For the Alhydrogel group, the antibody level decreased more gradually during the five-month period (~10 fold from 2 weeks to 20 weeks) (FIG. 7B). For the Adju-Phos group, the decline was more drastic (~43 fold; FIG. 7C).

Figure 7D:
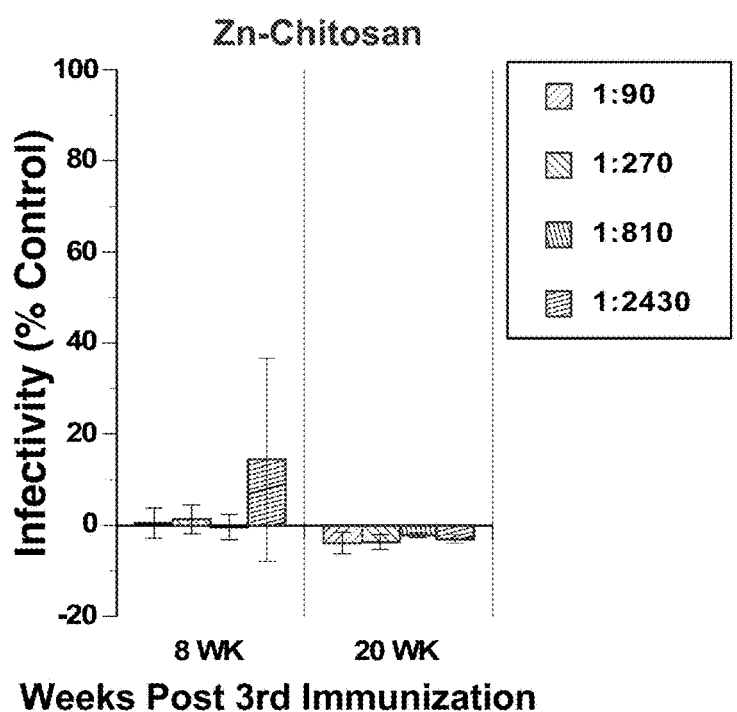
Figure 7E:
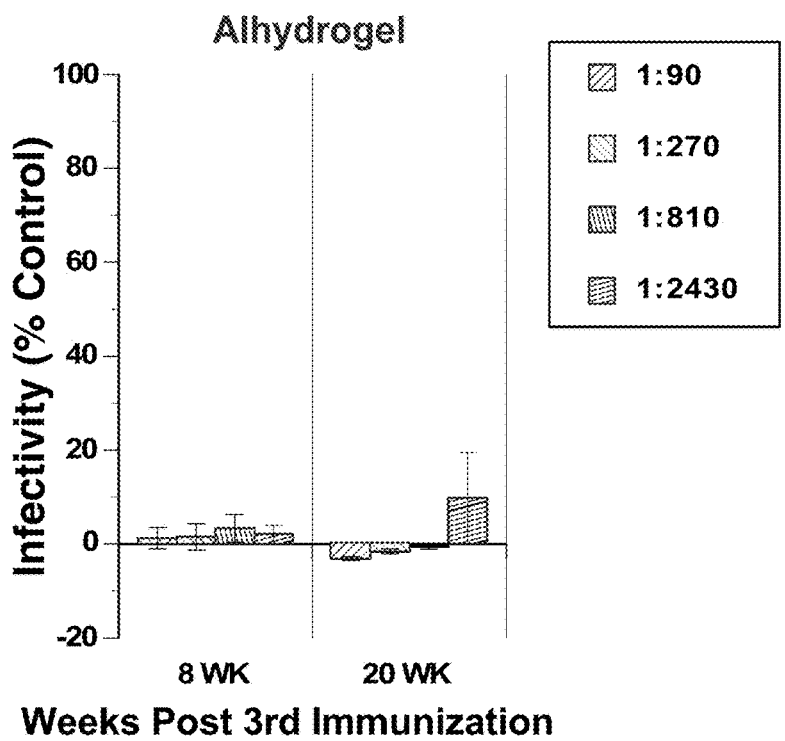
Figure 7F:
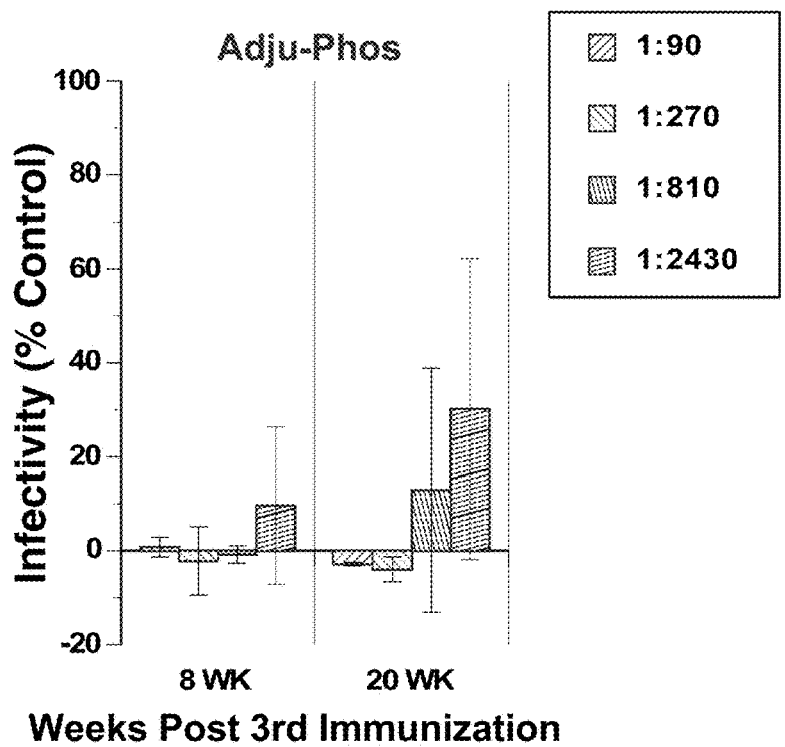

Although antigen binding antibody titers are important, what is more critical for protection are nAbs. As such, we also assessed nAb levels during the five months after the third immunization. For the Zn-chitosan group, $NT_{80}$ fluctuated between 810 and 7,290 (FIG. 7D). Interestingly, the nAb titer decreased gradually through 12 weeks. However, it increased back up on weeks 16 and 20. It is not clear why. We suspect this could be due to B-cell homeostasis through non-specific immune stimulation. For the Alhydrogel group, the neutralizing activity decreased about three-fold from the peak level at 2 weeks after the third immunization but remained fairly stable during the first 12 weeks with $NT_{80}$>2,430 (FIG. 7E). The neutralizing activity decreased on week 16 to 810, but similar to what we saw in the Zn-chitosan group, the activity increased back up to 2,430 on week 20. Even for the Adju-Phos group, $NT_{70}$ remained between 810 and 2,430 (FIG. 7F) during the five-month period.

Evaluation of Antibody Avidity

Figure 8B:
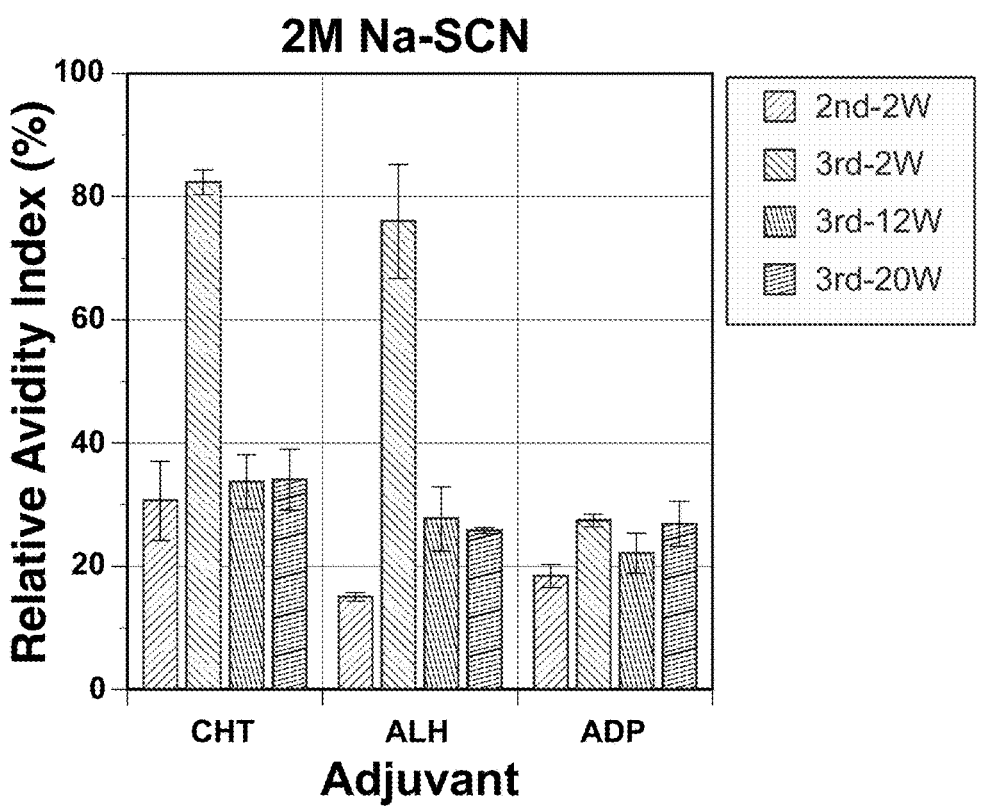
Figure 8C:
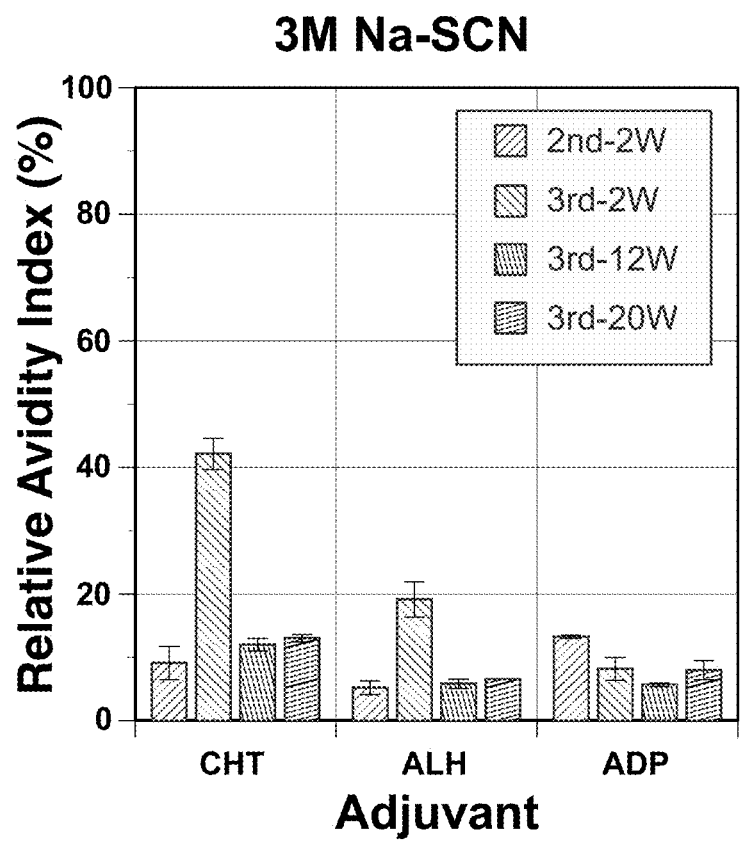

Although the antibody titers were virtually identical among the three groups vaccinated with different adjuvants after the first immunization (FIG. 4B), the only group that exhibited neutralizing activity at dilutions tested was the Zn-chitosan group (FIG. 5A). The differences in the neutralizing activity were more pronounced after the second immunization, especially when compared to the Adju-Phos group (FIG. 5). This difference could be due in part to differences in the epitopes being targeted as well as affinity/avidity of antibodies. As such, we assessed avidity of the antibodies at various times after immunization by doing ELISA in the absence or the presence of different concentrations of sodium thiocyanate. Overall, antibodies induced in Zn-chitosan group exhibited higher avidity, followed by Alhydrogel and Adju-Phos (FIG. 8). The observed avidity correlated with neutralizing activity. The avidity increased substantially after the third immunization compared with that after the second immunization, especially for the Zn-chitosan and Allydrogel groups. The high avidity was striking especially for the Zn-chitosan group with 40% of the antibodies able to bind the RBD even in 3 molar sodium thiocyanate. The avidity decreased with time to the level after the second immunization or slightly higher.

Examination of Immunogenic Linear Epitopes

Although vaccines must elicit high antibody titers, what is really important for their protective efficacy is whether elicited antibodies can target critical neutralizing epitopes and inhibit infection either by blocking binding to cellular receptors or by preventing conformational changes that are required for the virus entry process (e.g. membrane fusion). To begin to determine immunogenic epitopes on the RBD, we conducted ELISA with a panel of 17-mer overlapping peptides (10 a.a. overlap) that cover the entire length of the RBD immunogen (FIG. 9A). From this analysis, several linear epitopes were identified for the Zn-chitosan group (FIG. 9B). The three most immunogenic epitopes were $^{372}$ASFSTFKCYGVSPTKLN$^{388}$ (#54; SEQ ID NO: 13), $^{379}$CYGVSPTKLND-LCFTNV$^{395}$ (#55; SEQ ID NO: 14) and $^{456}$FRKSNLKPFERDISTEI$^{472}$ (#66; SEQ ID NO: 25). Two other epitopes with lower reactivity were $^{344}$ATR-FASVYAWNRKRISN$^{360}$ (#50; SEQ ID NO: 9) and $^{512}$VLSFELLHAPATVCGPK$^{528}$ (#74; SEQ ID NO: 32). The locations of these five peptides on the RBD are shown in FIG. 9C. Of these peptides, only peptides #66 was located within the RBM. There were a few other weakly reactive peptides, including $^{393}$TNVYADSFVIRGDEVRQ$^{409}$ (#57; SEQ ID NO: 16), $^{407}$VRQIAPGQTGKIADYNY$^{423}$ (#59; SEQ ID NO: 18), $^{421}$YNYKLPDDFTGCVIAWN$^{437}$ (#61; SEQ ID NO: 20) and $^{470}$TEIYQAGSTPCNGVEGF$^{486}$ (#68; SEQ ID NO: 27) (FIG. 9A).

One major unexpected result was that we were unable to detect any immunoreactive peptides when we used sera from animals immunized with Alhydrogel or Adju-Phos. Although this is likely due to genuine differences between in immune responses elicited using different adjuvants, it could also be due to inefficiencies of the ELISA using 17-mer overlapping peptides. First, the peptides could be too short to fold into structures that would resemble native structures on the RBD. Second, peptides could be adhered to ELISA plates in a manner that might not allow binding of antibodies elicited against them on the RBD. Even for detecting immunoreactive peptides for the Zn-chitosan group, we had to use 200 ng of peptides in each well and 1:300 dilution of sera.

To improve efficiency of detecting immunoreactive peptides we synthesized nine peptides shown in FIG. 10A. These peptides are different from the overlapping peptides shown in FIG. 9A in following ways. First, the peptides were designed based on their structure and surface exposure on the RBD. As such, they are of different lengths and do not cover the entire sequence of the RBD. Second, these peptides are preceded by three glycine residues and they are biotinylated at the N-terminal amine group. This allows the peptides to be bound to the ELISA plate via streptavidin coated onto the wells. The three glycine residues serve as a spacer between streptavidin and the RBD portion of peptide. Thus, the RBD peptide should be better able to fold into their native state and fully accessible to antibodies. Taken together, we hypothesized these peptides would be better suited for identifying immunogenic epitopes.

ELISA was done using the new peptides with serum samples collected two weeks after each immunization (FIG. 10B). As hypothesized, we were able to detect immunoreactive peptides more readily. Overall, results were in good agreement with what was observed with overlapping 17-mer peptides. First, serum samples collected from the Zn-chitosan group reacted to more peptides than sera from the other two groups. While sera from Zn-chitosan group reacted against peptides P2, P3, P4, P5, P7 and P9 after three immunizations, sera from Alhydrogel and Adju-Phos groups reacted only against P6 and P9 peptides. This may suggest that Zn-chitosan and aluminum-based adjuvants work fundamentally in different ways to induce antibodies. Second, both assays identified similar immunogenic peptides: P2 (#50), P3 (#54 and #55), P4 (#59), P5 (#59), P6 (#66), P7 (#68) and P9 (#74).

For the Zn-chitosan group, the two most immunogenic linear epitopes were within P6 and P7 ($^{457}$RKSNLKPFERDISTEIYQAGSTP$^{479}$ (SEQ ID NO: 39) and $^{469}$STEIYQAGSTPCNGVEGFNCYFPL$^{492}$ (SEQ ID NO: 40)). They are situated in the middle of the RBM and contain residues that are critical for binding ACE2 (FIG. 10A). However, these peptides mostly face away from the ACE2 binding site (FIG. 10C). Depending on which face of the peptide structure antibodies bind, they may or may not exhibit neutralizing activity. More detailed epitope mapping analyses and characterization of antibodies at the monoclonal level would be needed.

Most of the immunogenic peptides were distant from the actual ACE2 binding site (FIG. 10C). However, these peptides, with the exception of peptide P9, form parts of the RBD surface that overlap footprints of known nAbs against SARS-CoV-2 (FIG. 10D). For example, peptide P3 is well away from the ACE2 binding site. However, several neutralizing monoclonal antibodies (mAbs) bind this region, including S2A4 (23), H014 (24), CR3022 (17), EY6A (25) and H11-H4 (26). Another example is mAb 5309 (27), footprint of which lies on peptide P2. Thus, antibodies that bind to these peptides could exhibit neutralizing activity.

Peptide P8, which is situated at the C-terminal end of the RBM and contains the greatest number of residues that make direct contact with ACE2, was not reactive to any of the antisera. This does not necessarily mean that nAbs that bind the ACE2 binding site were not elicited. It is highly likely that the P8 peptide is unable to fold into a conformation that resembles the native structure found on the intact RBD. Peptide P5, which is situated at the N-terminal end of the RBM and contains three residues that contact ACE, was weakly reactive.

Discussion

During the past eleven months, significant global efforts have been made towards developing COVID-19 vaccines using different vaccine platforms. They include vaccines based on inactivated viruses, nucleic acids (DNA and RNA), viral vectors, and recombinant subunit proteins. Several vaccine candidates are already in Phase 3 clinical trials, including those by Moderna/NIH (mRNA), BioNTech/Pfizer (mRNA), CanSino Biologics (Adenovirus 5), University of Oxford/AstraZeneca (ChAdOx1), Janssen/Johnson & Johnson (Adenovirus 26), Wuhan Institute of Biological Products/Sinopharm (inactivated virus), Beijing Institute of Biological Products/Sinopharm (inactivated virus), and Sinovac (inactivated virus). There are many other vaccine candidates currently being tested in Phase I/II clinical trials.

When developing a vaccine, two major factors have to be considered first; an immunogen and a vaccine delivery platform. They are decided largely based on what immune correlates of protection are, how best the protective immunity can be induced, and how easily or cost-effectively vaccine candidates can be produced. For most, if not all, viruses, neutralizing antibodies are undoubtedly the most critical correlates of protection. No doubt, this is the reason why all COVID-19 subunit vaccine candidates being evaluated are based on the spike (S) glycoprotein, the only known target for neutralizing antibodies for coronaviruses. It is also the reason why induction of potent, durable neutralizing antibody responses will be critical for the protective efficacy of COVID-19 vaccines.

Our efforts to develop a subunit protein vaccine based on the RBD stems largely from prior vaccine development efforts made against SARS-CoV. Since the emergence of SARS-CoV in 2002, various strategies have been explored to develop a vaccine against the virus. They include inactivated viruses (28-33), a live-attenuated virus (34), DNA (35-38), and a viral vector vaccine (39). Overall, results from these studies showed limited success. By comparison, subunit protein vaccines based on the RBD induced higher nAb titers and resulted in more consistent protection against virus challenges. Different RBD-based immunogens, either alone (12) or fused to IgG Fc (13), have been produced in various recombinant protein expression systems, including mammalian cell lines (293T, CHO), insect cells (Sf9), yeast and *E. coli* (10, 12, 40). Their immunogenic properties have been evaluated in different animal models using different adjuvants and immunization routes. To summarize a large body of work, it has been demonstrated that (i) RBD can sufficiently induce nAbs; (ii) RBD expressed in 293T cells elicited significantly higher nAbs than RBD expressed in Sf9 or *E. coli* (12); and (iii) RBD-based vaccines can induce long-term neutralizing activity and protective immunity (11). Importantly, it has been shown that potent and persistent antibody responses against the RBD exist in recovered patients (40). Advantages of RBD-based vaccines, over the use of the entire S protein, have been discussed (41).

In this study, we evaluated immunogenicity of a glycosylated, monomeric RBD-based subunit protein immunogen ($T^{333}$ to $K^{528}$) produced in 293F human cells. Three different adjuvants were compared. Using Alhydrogel, an FDA-approved adjuvant for clinical use, we did not detect nAbs after the first immunization, at least at 1:90 dilution. However, two immunizations induced $NT_{80}$ of ~810 ($NT_{50}$ of >2,430) against live infectious SARS-CoV-2, which is significantly greater than titers observed in convalescent sera in recovered patients (21, 22). One additional immunization induced remarkably high $NT_{70}$ of ~14,580. The neutralizing antibody response was highly durable. Despite gradual decline, $NT_{80}$ remained >2,430. The antibody responses were substantially weaker using Adju-Phos with respect to all major parameters monitored (i.e. kinetics of nAb induction, titer of nAbs, durability, and avidity).

In contrast to alum-based adjuvants, Zn-chitosan was able to induce potent nAbs even after a single immunization with $NT_{80}$ of ~270 despite similar antigen-binding antibody levels. The $NT_{80}$ increased almost 10-fold to 2,430 after the second immunization, about 3-fold higher than the Alhydrogel group. However, after the third immunization, the neutralizing activity increased only about 3-fold, compared to >81-fold for the Alhydrogel group. We suspect this is most likely due to interference by high levels of pre-existing antibodies after the second immunization, similar to maternal antibody interference of vaccine efficacy. In this regard, a longer vaccination interval to allow antibody waning could have improved boosting efficiency and resulted in greater neutralizing activity. In this study, we used Zn-chitosan as a yardstick to gauge immunogenic potential of our RBD immunogen. The results indicate that RBD is inherently immunogenic and that it may be possible to elicit stronger antibody responses than what we observed using Alhydrogel if we were to use more potent adjuvants that are already approved by the FDA.

To date, results from many preclinical and clinical vaccine studies have been reported. Protective efficacy of two β-propionolactone-inactivated virus vaccines (BBIBP-CorV (42) and PiCoVacc (43)) have been evaluated in non-human primates. Macaques were immunized two or three times with BBIBP-CorV or PiCoVacc, respectively. Although both vaccines were able to protect animals, nAb titers were relatively weak ($NT_{50}$ of 256 and 50, respectively). One important consideration is that animals were challenged less than 10 days after the final immunization. Thus, the long-term protective efficacy of these vaccine candidates is currently unknown.

A preliminary report from the Phase 1 clinical trial by Moderna indicated that the RNA vaccine that encodes a stabilized prefusion trimeric spike protein can elicit both cellular and humoral immune responses(21). The vaccine required two doses to elicit binding and neutralizing antibody titers that were comparable to those observed in human convalescent sera. $NT_{80}$ of 340 and 654 were elicited using 25 μg and 100 μg doses, respectively. Although the vaccine did not exhibit serious toxicity, significant reactogenicity and systemic adverse events were observed especially after the second immunization and for higher doses. The same vaccine in 100 μg dose was able to induce high levels of nAbs ($NT_{50}$ of 3,481) and significantly reduce viral load in rhesus macaques against virus challenge four weeks post last immunization (44). Similarly, DNA vaccines encoding various segments of S protein also reduced viral load by over 3 logs in bronchioalveolar lavage and nasal mucosa (45). However, neutralizing antibody titers against infectious SARS-CoV-2 were relatively low (median titer of 74). Macaques immunized with chimpanzee adenovirus vector encoding S protein (ChAdOx1mCoV-19) also exhibited similar protection with neutralizing antibody titers ranging 10-160 (46). Similarly, Janssen/Johnson & Johnson's adenovirus 26-based vector that expresses stabilized trimeric S protein induced only $NT_{50}$ of 113 in macaques but was protective against $1\times10^5$ $TCID_{50}$ SARS-CoV-2 challenge (47). Preliminary data from their Phase 1/2a study are currently being peer reviewed.

Protective efficacy of a recombinant RBD produced in Sf9 insect cells using a recombinant baculovirus has also been evaluate in macaques (48). Animals were immunized twice intramuscularly seven days apart with 20 μg or 40 μg of recombinant RBD. Although relatively low levels of nAbs were induced ($NT_{50}$ of ~100), the animals were protected from SARS-CoV-2 challenge three weeks after the last immunization.

There have been a number of efforts to enhance immunogenicity of the RBD. One strategy was to fuse the protein to the Fc domain of human IgG1 (RBD-Fc) (49). Mice were immunized subcutaneously twice, fourteen days apart, with 10 μg of antigens using MF59 as an adjuvant. Mice immunized with RBD-Fc mounted much higher nAbs against live SARS-CoV-2 with $NT_{100}$ of 25 compared to only 5 for RBD. Another strategy that has been evaluated to increase immunogenicity of the RBD is to generate a single chain dimeric RBD by cloning two RBD in tandem (50). Mice were immunized with 10 μg of monomeric or dimeric RBD twice using AddaVax as an adjuvant. Compared to monomeric RBD which only induced $NT_{50}$ of only 128 or 256 in two of eight animals, dimeric RBD induced average $NT_{50}$ of 3,008.

Another strategy that has been evaluated is to deliver RBD as a particulate form using liposomes (51). Here, a recombinant RBD with a histidine tag was incorporated onto liposomes containing cobalt-porphyrin-phospholipid (Co-PoP). Mice were immunized twice intramuscularly with 100 ng of RBD using monophosphoryl lipid A (MPLA) or MPLA/QS21 as adjuvants. $NT_{50}$ of 1,280 were induced in both groups, compared to $NT_{50}$<160 for the same immunogen adjuvanted with Alum. They were able to induce similar level of nAbs in rabbits using 20 μg of the RBD, but only when QS21 was used, compared to $NT_{50}$ of ~320 using Alum.

Not surprisingly, RBD immunogen can be delivered by mRNA platform as well (52). Mice immunized twice, four weeks apart, with 30 μg of RNA elicited $NT_{50}$ of 540 against infectious SARS-CoV-2. Importantly, immunization with RBD induced significantly higher nAb titer than a comparable RNA vaccine encoding S1 domain of the spike protein. Most recently, results of Phase 1/2 evaluation of BioNTech/Pfizer's RNA vaccine (BNT162b1) that encodes trimeric RBD was published (53). The vaccine was administered intramuscularly twice, separated by 21 days. $NT_{50}$ of about 437 was induced against infectious SARS-CoV-2 using 30 μg dose.

Compared with most other COVID-19 vaccine studies, especially those that evaluated immunogenicity of the RBD, we were able to induce higher titers of nAbs. While this could be due to inherent differences between immunogens (e.g. RBD vs trimeric S protein) and/or vaccine delivery platforms (e.g. subunit protein vs. RNA or viral vector), there could be other possible reasons (e.g. antigenic dosage, immunization routes, adjuvants, vaccination schedule and animal model used). Since no two vaccine regimens are exactly identical, it is not simple to determine which immunogen or vaccine delivery platform is better. In addition, it should be noted that there are subtle differences between virus neutralization assays (e.g. assay methodology and amounts of infectious units used). Standardizing the methodology or having a common positive control could facilitate comparing different vaccine candidates.

Most vaccine studies that have been conducted thus far used two-immunization regimens. While two immunizations might be sufficient to elicit nAb titers that are greater than the levels observed in convalescent sera, the results from our study clearly demonstrate that a third immunization can substantially increase antibody avidity (FIG. 8) as well as nAb titers (FIG. 5). Although we did not evaluate two-immunization regimens for side-by-side comparison, we highly suspect that nAbs elicited after three immunizations would be more durable than those induced after only two immunizations. In this regard, while our RBD immunogen can be used as a standalone vaccine candidate, it could also be used as a boosting antigen for other vaccine candidates, especially the viral vector vaccines that usually cannot be used more than twice due to immune responses elicited against viral vectors.

One thing we are really puzzled is the differences in the linear immunogenic epitopes between the Zn-chitosan and Aluminum-based adjuvant groups (FIGS. 7 and 8). While antibodies induced in the Zn-chitosan group were able to bind to many peptides, those induced in Alhydrogel or Adju-Phos groups only recognized two. This could be due to differences in how antigens are processed by antigen presenting cells and/or how they are presented to B cells. We are not sure at this time whether this is beneficial for eliciting nAbs or not. Although nAbs were induced in the Zn-chitosan group faster, it is possible that induction of nAbs may have nothing to do with eliciting antibodies that could bind peptides. In any event, additional immunological and structural studies at the monoclonal level are needed to better characterize this phenomenon.

In conclusion, results of our study clearly demonstrate that the RBD of S protein is sufficient to elicit potent nAbs against SARS-CoV-2 and that it is a highly promising vaccine candidate. As shown in other studies, the RBD can be delivered via other vaccine delivery platforms besides subunit protein (e.g. RNA, liposome-based nanoparticles as well as viral vectors).

Materials and Methods
Cloning, Expression and Purification of RBD Immunogen

To generate our RBD-based vaccine candidate, we used the sequence of Wuhan-Hu-1 strain of SARS-CoV-2 (GenBank: MN908947.3). A DNA fragment encoding the following elements were synthesized by Twist Biosciences and cloned into pTwist-CMV-Hygro mammalian expression vector to generate pCOVID-19-RBD: (1) A μ-phosphatase secretory signal peptide (MGILPSPGMPALLSLVSLLSVLLMGCVAE (SEQ ID NO: 43)), (2) N-terminal flanking six amino acids (KLTGGT (SEQ ID NO: 44)), (3) RBD (from $T^{333}$ to $K^{528}$ of the S protein (SEQ ID NO: 45)), (4) C-terminal flanking four residues (GPGM (SEQ ID NO: 46)) followed by a six-Histidine tag. The additional amino acid residues flanking the N- and C-terminal ends of the RBD were added for restriction sites (Hind III/Age I/Kpn I and Xma I/Nsi I, respectively) to facilitate transfer of the gene into different expression vectors. Following cleavage of the signal peptide, the C-terminal E residue is expected to remain on the final antigen. Additional non-coding sequences were used at the ends of the gene to ensure optimal Kozak sequence and compatibility with the plasmid vector. The final construct was sequenced to confirm intactness of the RBD gene.

The plasmid was transfected into Freestyle 293F cells (Invitrogen) using 293Fectin (Gibco) according to the manufacturer's instructions. Briefly, 2 μl of 293Fectin was mixed with 1 μg of DNA and added to 293F cells at a final density of $1\times10^6$/ml. 293F cells were cultured in FreeStyle™ 293 expression medium (Gibco) in suspension at 37° C. under 8% $CO_2$ with shaking at 150 rpm. Cell culture medium was harvested five days after transfection and the protein was purified by affinity chromatography using Ni-NTA resin (Qiagen). Briefly, cell culture medium, clarified by centrifugation at 2,500×g for 30 min, was loaded into the Ni-NTA column and washed with washing buffer (50 mM $Na_2HPO_4$, 300 nM NaCl, 20 mM imidazole, pH 8.0), and eluted with elution buffer washing buffer containing 250 nM imidazole). The eluted fractions were concentrated using Amicon Ultra concentrator (Millipore) with a 10 kDa cut-off filter. Protein concentration was determined by measuring absorbance at 280 nm using multi-mode microplate reader (BioTek Synergy 2). Protein purity and integrity were analyzed by sodium dodecyl sulfate polyacrylamide gel electrophoresis (SDS-PAGE) followed by visualization of the protein using PAGE Blue stain (Invitrogen).

CR3022 Expression and Purification

A plasmid construct that encode heavy and light chain genes of a monoclonal antibody (mAb) CR3022 in backbone of pDR12, a two-promoter plasmid, was kindly provided by Dr. Tianlei Ying (Fudan University, Shanghai, China). CR3022 was expressed by transfecting the plasmid into FreeStyle 293F cells with 293Fectin transfection reagent, Cell culture medium was harvested five days after transfection and clarified by centrifugation. Clarified medium was diluted 1:1 with protein A IgG Binding Buffer (Thermo Scientific) and filtered through 0.22 μm filter to remove any precipitate before incubation with Protein A Plus Agarose (Thermo Scientific). After binding, antibody was eluted from the column using low pH IgG Elution Buffer (Thermo Scientific) and neutralized immediately in collection tubes. The purified antibody was buffer-exchanged with PBS and concentrated using Amicon Ultra concentrator with a 30 kDa cut-off filter.

Characterization of RBD Glycosylation and Binding to CR3022

Purified RBD was deglycosylated using endoglycosidase H (Endo H) or peptide-N-glycosidase F (PNGase F) according to the manufacturer's protocol (New England Biolabs). Briefly, 5 μg of proteins for each reaction was denatured for 10 min at 100° C., and 10 U of Endo H or PNGase F was added. The reaction mixture was incubated at 37° C. for 2 hr and then analyzed by SDS-PAGE.

Binding of RBD to CR3022 was tested by standard ELISA. Each well of MaxiSorp plates (Nunc) was coated with 100 ng of RBD in 100 μl coating buffer (0.1 M $Na_2CO_3$/$NaHCO_3$, pH 9.6) overnight at 4° C., followed by blocking with 5% calf serum (CS) and 2.5% skim milk in PBS. Then, 3-fold serially diluted CR3022 was added, starting at 20 μg/ml and incubated for 2 hours at 37° C. After washing (PBS, 0.05% Tween 20), goat anti-human IgG antibody conjugated with HRP (SouthernBiotech) was added and incubated for 1 hour at 37° C. After another wash, TMB substrate (3,3',5,5'-Tetramethylbenzidine, BioRad) was added and the reaction was stopped by adding 2N $H_2SO_4$. Absorbance at 450 nm (A450) was measured using Spectra Max microplate reader (Molecular Devices Inc.).

Mice Immunization 5-6-week old female BALB/c mice were purchased from the Jackson Laboratory (Bar Harbor, Me.). Mice were group housed in a temperature-controlled environment at 22-24° C. with 12 hr day-night cycles and received food and water ad libitum. All animal experiments were performed in Laboratory Animal Resource (LAR) facility of College of Veterinary Medicine, Iowa State University, in accordance with approved protocol (IACUC-20-018) and guidelines of Institutional Animal Care and Use Committee (IACUC).

Mice (4 or 5 per group) were primed intraperitoneally with 30 µg of RBD with or without adjuvants in 200 µl volume. Mice were subsequently boosted twice with 20 µg of RBD two and about five weeks after the first immunization. Alhydrogel or Adju-Phos (Invivogen) were mixed 1:1 (v/v) with RBD as per manufacturer's recommendation. Zn-chitosan was prepared (18, 54) and mixed with RBD (1000:1, w/w) for 3 hrs prior to immunization. Sham controls were immunized with PBS only, Mice were bled from saphenous vein for serum collection prior to first immunization (pre-immune) or after immunization at indicated times. For this initial study, the primary objective was to compare each vaccine group with the mock vaccinated group (PBS), not between the vaccine groups, with respect to their ability to induce antigen-binding or neutralizing antibodies. For this type of analyses in inbred mice, a sample size of 4 in each group is sufficient and will have >95% power to detect an effect size of ≥3.1 with statistically significance of 0,05.

ELISA for Characterizing Antibody Responses.

RBD-specific antibody titers in serum samples collected at different times after immunization were determined by standard ELISA as described above. Wells were coated with 100 ng of RBD. After blocking, either pooled or individual serum samples were used at indicated dilutions. Goat anti-mouse IgG conjugated with HRP (SouthernBiotech) was used as a secondary antibody. Assays were done in duplicates.

To determine immunogenic linear epitopes, ELISA was done with either a panel of overlapping 17-mer peptides obtained from BEI Resources (NR-52402: NIAID, NIH) or biotinylated peptides (P1-P9, provided by NeoVaxSyn, Inc, was synthesized by Synpeptide, Shanghi, China). Peptides were solubilized in PBS (50% DMSO). 17-mer peptides were coated onto ELISA plates overnight at 4° C. using a standard coating buffer (200 ng/well). To bind biotinylated peptides, streptavidin (Thermo Scientific) was first coated onto ELISA plates overnight (300 ng/well). After blocking with 1% BSA, 100 ng of biotinylated peptides were allowed to bind streptavidin for 1 hr. For both sets of peptides, 1:300 diluted serum samples were used. Goat anti-mouse IgG conjugated with HRP (SouthernBiotech) was used as a secondary antibody. Assays were done in duplicates.

To compare antibody avidity, ELISA was done using indicated serum samples in the absence or the presence of sodium thiocyanate (NaSCN, BeanTown Chemical, Hudson, N.H.). Briefly, after binding primary antibodies (1:1800 diluted sera), plates were washed and the wells were incubated with 100 µl of 0, 1, 2 or 3M NaSCN in PBS for 15 min. Subsequently, solutions were removed, and the rest of the assay was done as descried above. Relative avidity index was calculated as a percentage of absorbance in NaSCN-treated wells compared to untreated wells.

SARS-CoV-2 Virus Stock Preparation

SARS CoV-2 (ATCC CRL-1586) isolated from a COVID-19 patient in Washington, USA. was acquired from ATCC. Confluent monolayers of VeroE6 cells (CRL-1586; ATCC) were infected and cultured in Dulbecco's Modified Eagle Medium (DMEM, Corning) containing 5% FBS at 37° C. under 5% $CO_2$, Virus was passaged three times to generate a stock. Virus titer was determined to be $2.5\times10^6$ PFU/ml by plaque-forming assay. The stock was aliquoted in small volumes and stored at −80° C. until use.

Microneutralization (MN) Assays

Vero E6 cells were plated in flat bottom 96-well plates at a density of $2\times10^4$ cells/well and incubated overnight at 37° C. at 5% $CO_2$. Pooled or individual serum samples were diluted with DMEM (1:15) and heat inactivated at 56° C. for 30 min. For the MN assay. 50 µl of 3-fold serial dilutions of the sera were prepared in triplicate, starting at 1:15 or 1:45, and incubated with equal volume of 50 ITU SARS-CoV-2 virus (for final dilutions of 1:30 or 1:90, respectively) for 1 hr at 37° C. Serum/virus mixtures were transferred into the wells of 96-well plates with confluent monolayers of VeroE6 cells. After incubation for 1 hr at 37° C., supernatant was removed, and 200 µl of fresh DMEM containing 5% FBS was added. Plates were incubated for 3 days at 37° C., 5% $CO_2$. Subsequently, cell culture medium from each well was collected for downstream assays.

To assess neutralization activity, we measured lactate dehydrogenase (LDH) activity in cell culture medium using CyQuant LDH Cytotoxicity assay kit (Invitrogen) as per the manufacturer's recommended protocol. LDH is an enzyme found in the cytoplasm, which is released into culture medium when cells lyse. Thus. LDH activity is directly proportional to number of cells lysed upon virus infection. Briefly, 50 µl of cell culture medium was transferred to a 96-well flat bottom plate and mixed with 50 µl reaction buffer. The plate was incubated at room temperature for 30 min. Absorbance was measured at 490 nm and 680 nm and corrected absorbance was obtained by subtracting 680 nm absorbance from 490 nm absorbance. LDH activity in uninfected and infected cells were used as negative and positive controls, respectively. Infectivity was calculated as: $(OD_{virus/serum}-OD_{uninfected})/(OD_{virus}-OD_{uninfected})$. Neutralization titers (e.g. $NT_{50}$ or $NT_{80}$) represent reciprocal of the highest serum dilutions that result in 50% or 80% protection, respectively.

To validate LDH-based assay, we also conducted RT-qPCR assay using the culture media of cells from the MN assay. Briefly, 100 µl of cell culture media were collected and mixed with 400 µl of trizol. 80 µl of chloroform was added and centrifuged at 12,000×g at 4° C. for 15 min, 200 µL of isopropanol was added to the upper aqueous layer and centrifuged for 10 min at 12,000×g and 4° C. RNA pellet was washed with ethanol and resuspended in 50 µl of water. RT-qPCR of the extracted RNA was performed by using Luna Universal Probe One-Step RT-qPCR kit and primer-probe from IDT 2019-nCoV kit on the Applied Biosystems QuantStudio 3 real-time PCR system.

Structural Analyses

Visualization and analyses of RBD structures (PDB: 6M0J) were done using UCSF Chimera. To generate footprints of nAbs, a tool in Chimera (Clashes/Contacts) was used to identify residues on RBD that contact nAbs. Default contact criteria of VDW overlap ≥−0.4 Å was used.

REFERENCES

1. C. Huang, Y. Wang, X. Li, L. Ren, J. Zhao, Y. Hu, L. Zhang, G. Fan, J. Xu, X. Gu, Z. Cheng, T. Yu, J. Xia, Y. Wei, W. Wu, X. Xie, W. Yin, H. Li, M. Liu, Y. Xiao, H. Gao, L. Guo, J. Xie, G. Wang, R. Jiang, Z. Gao, Q. Jin, J. Wang, B. Cao, Clinical features of patients infected with 2019 novel coronavirus in Wuhan, China. *Lancet* 395, 497-506 (2020).
2. Q. Li, X. Guan, P. Wu, X. Wang, L. Zhou, Y. Tong, R. Ren, K. S. M. Leung, E. H. Y. Lau, J. Y. Wong, X. Xing, N. Xiang, Y. Wu, C. Li, Q. Chen, D. Li, T. Liu, J. Zhao, M. Liu, W. Tu, C. Chen, L. Jin, R. Yang, Q. Wang, S. Zhou, R. Wang, H. Liu, Y. Luo, Y. Liu, G. Shao, H. Li, Z. Tao, Y. Yang, Z. Deng, B. Liu, Z. Ma, Y. Zhang, G. Shi, T. T. Y. Lam, J. T. Wu, G. F. Gao, B. J. Cowling, B. Yang, G. M. Leung, Z. Feng, Early Transmission Dynamics in Wuhan, China, of Novel Coronavirus-Infected Pneumonia. *N Engl J Med* 382, 1199-1207 (2020).
3. L. Gardner, in *Coronavirus COVID-19 Global Cases*. (Johns Hopkins University Center for Systems Science and Engineering, 2020).
4. P. Zhou, X. L. Yang, X. G. Wang, B. Hu, L. Zhang, W. Zhang, H. R. Si, Y. Zhu, B. Li, C. L. Huang, H. D. Chen, J. Chen, Y. Luo, H. Guo, R. D. Jiang, M. Q. Liu, Y. Chen, X. R. Shen, X. Wang, X. S. Zheng, K. Zhao, Q. J. Chen, F. Deng, L. L. Liu, B. Yan, F. X. Zhan, Y. Y. Wang, G. F. Xiao, Z. L. Shi, A pneumonia outbreak associated with a new coronavirus of probable bat origin. *Nature* 579, 270-273 (2020).
5. J. Lan, J. Ge, J. Yu, S. Shan, H. Zhou, S. Fan, Q. Zhang, X. Shi, Q. Wang, L. Zhang, X. Wang, Structure of the SARS-CoV-2 spike receptor-binding domain bound to the ACE2 receptor. *Nature* 581, 215-220 (2020).
6. J. Shang, G. Ye, K. Shi, Y. Wan, C. Luo, H. Aihara, Q. Geng, A. Auerbach, F. Li, Structural basis of receptor recognition by SARS-CoV-2. *Nature* 581, 221-224 (2020).
7. A. C. Walls, Y. J. Park, M. A. Tortorici, A. Wall, A. T. McGuire, D. Veesler, Structure, Function, and Antigenicity of the SARS-CoV-2 Spike Glycoprotein. *Cell* 181, 281-292 e286 (2020).
8. D. Wrapp, N. Wang, K. S. Corbett, J. A. Goldsmith, C. L. Hsieh, O. Abiona, B. S. Graham, J. S. McLellan, Cryo-EM structure of the 2019-nCoV spike in the prefusion conformation. *Science* 367, 1260-1263 (2020).
9. P. Zhao, J. L. Praissman, O. C. Grant, Y. Cai, T. Xiao, K. E. Rosenbalm, K. Aoki, B. P. Kellman, R. Bridger, D. H. Barouch, M. A. Brindley, N. E. Lewis, M. Tiemeyer, B. Chen, R. J. Woods, L. Wells, Virus-Receptor Interactions of Glycosylated SARS-CoV-2 Spike and Human ACE2 Receptor. *Cell Host Microbe* 28, 586-601 e586 (2020).
10. W. H. Chen, L. Du, S. M. Chag, C. Ma, N. Tricoche, X. Tao, C. A. Seid, E. M. Hudspeth, S. Lustigman, C. T. Tseng, M. E. Bottazzi, P. J. Hotez, B. Zhan, S. Jiang, Yeast-expressed recombinant protein of the receptor-binding domain in SARS-CoV spike protein with deglycosylated forms as a SARS vaccine candidate. *Hum Vaccin Immunother* 10, 648-658 (2014).
11. L. Du, G. Zhao, Y. He, Y. Guo, B. J. Zheng, S. Jiang, Y. Zhou, Receptor-binding domain of SARS-CoV spike protein induces long-term protective immunity in an animal model. *Vaccine* 25, 2832-2838 (2007).
12. L. Du, G. Zhao, L. Li, Y. He, Y. Zhou, B. J. Zheng, S. Jiang, Antigenicity and immunogenicity of SARS-CoV S protein receptor-binding domain stably expressed in CHO cells. *Biochem Biophys Res Commun* 384, 486-490 (2009).
13. Y. He, Y. Zhou, S. Liu, Z. Kou, W. Li, M. Farzan, S. Jiang, Receptor-binding domain of SARS-CoV spike protein induces highly potent neutralizing antibodies: implication for developing subunit vaccine. *Biochem Biophys Res Commun* 324, 773-781 (2004).
14. J. ter Meulen, E. N. van den Brink, L. L. Poon, W. E. Marissen, C. S. Leung, F. Cox, C. Y. Cheung, A. Q. Bakker, J. A. Bogaards, E. van Deventer, W. Preiser, H. W. Doerr, V. T. Chow, J. de Kruif, J. S. Peiris, J. Goudsmit, Human monoclonal antibody combination against SARS coronavirus: synergy and coverage of escape mutants. *PLoS Med* 3, e237 (2006).
15. X. Tian, C. Li, A. Huang, S. Xia, S. Lu, Z. Shi, L. Lu, S. Jiang, Z. Yang, Y. Wu, T. Ying, Potent binding of 2019 novel coronavirus spike protein by a SARS coronavirus-specific human monoclonal antibody. *Emerg Microbes Infect* 9, 382-385 (2020).
16. M. Yuan, N. C. Wu, X. Zhu, C. D. Lee, R. T. Y. So, H. Lv, C. K. P. Mok, I. A. Wilson, A highly conserved cryptic epitope in the receptor-binding domains of SARS-CoV-2 and SARS-CoV. *Science*, (2020).
17. J. Huo, Y. Zhao, J. Ren, D. Zhou, H. M. E. Duyvesteyn, H. M. Ginn, L. Carrique, T. Malinauskas, R. R. Ruza, P. N. M. Shah, T. K. Tan, P. Rijal, N. Coombes, K. R. Bewley, J. A. Tree, J. Radecke, N. G. Paterson, P. Supasa, J. Mongkolsapaya, G. R. Screaton, M. Carroll, A. Townsend, E. E. Fry, R. J. Owens, D. I. Stuart, Neutralization of SARS-CoV-2 by Destruction of the Prefusion Spike. *Cell Host Microbe* 28, 445-454 e446 (2020).
18. Y. Qin, M. B. Banasik, S. Kim, A. Penn-Nicholson, H. H. Habte, C. Labranche, D. C. Montefiori, C. Wang, M. W. Cho, Eliciting Neutralizing Antibodies with gp120 Outer Domain Constructs Based on M-Group Consensus Sequence *Virology* 462-463, 363-376 (2014).
19. Y. Qin, S. Banerjee, A. Agrawal, H. Shi, M. Banasik, F. Lin, K. Rohl, C. LaBranche, D. C. Montefiori, M. W. Cho, Characterization of a Large Panel of Rabbit Monoclonal Antibodies against HIV-1 gp120 and Isolation of Novel Neutralizing Antibodies against the V3 Loop. *PloS one* 10, e0128823 (2015).
20. Y. Qin, H. Shi, S. Banerjee, A. Agrawal, M. Banasik, M. W. Cho, Detailed characterization of antibody responses against HIV-1 group M consensus gp120 in rabbits. *Retrovirology* 11, 125 (2014).
21. L. A. Jackson, E. J. Anderson, N. G. Rouphael, P. C. Roberts, M. Makhene, R. N. Coler, M. P. McCullough, J. D. Chappell, M. R. Denison, L. J. Stevens, A. J. Pruijssers, A. McDermott, B. Flach, N. A. Doria-Rose, K. S. Corbett, K. M. Morabito, S. O'Dell, S. D. Schmidt, P. A. Swanson, 2nd, M. Padilla, J. R. Mascola, K. M. Neuzil, H. Bennett, W. Sun, E. Peters, M. Makowski, J. Albert, K. Cross, W. Buchanan, R. Pikaart-Tautges, J. E. Ledgerwood, B. S. Graham, J. H. Beigel, R. N. A. S. G. m, An mRNA Vaccine against SARS-CoV-2—Preliminary Report. *N Engl J Med*, (2020).
22. P. Wang, L. Liu, M. S. Nair, M. T. Yin, Y. Luo, Q. Wang, T. Yuan, K. Mori, A. G. Solis, M. Yamashita, A. Garg, L. J. Purpura, J. C. Laracy, J. Yu, L. Joshua-Tor, J. Sodroski, Y. Huang, D. D. Ho, SARS-CoV-2 neutralizing antibody responses are more robust in patients with severe disease. *Emerg Microbes Infect* 9, 2091-2093 (2020).
23. L. Piccoli, Y. J. Park, M. A. Tortorici, N. Czudnochowski, A. C. Walls, M. Beltramello, C. Silacci-Fregni, D. Pinto, L. E. Rosen, J. E. Bowen, O. J. Acton, S. Jaconi, B. Guarino, A. Minola, F. Zatta, N. Sprugasci, J. Bassi, A. Peter, A. De Marco, J. C. Nix, F. Mele, S. Jovic, B. F. Rodriguez, S. V. Gupta, F. Jin, G. Piumatti, G. Lo Presti, A. F. Pellanda, M. Biggiogero, M. Tarkowski, M. S. Pizzuto, E. Cameroni, C. Havenar-Daughton, M. Smithey, D. Hong, V. Lepori, E. Albanese, A. Ceschi, E. Bemasconi, L. Elzi, P. Ferrari, C. Garzoni, A. Riva, G. Snell, F. Sallusto, K. Fink, H. W. Virgin, A. Lanzavecchia, D.

Corti, D. Veesler, Mapping Neutralizing and Immunodominant Sites on the SARS-CoV-2 Spike Receptor-Binding Domain by Structure-Guided High-Resolution Serology. *Cell* 183, 1024-1042 e1021 (2020).
24. Z. Lv, Y. Q. Deng, Q. Ye, L. Cao, C. Y. Sun, C. Fan, W. Huang, S. Sun, Y. Sun, L. Zhu, Q. Chen, N. Wang, J. Nie, Z. Cui, D. Zhu, N. Shaw, X. F. Li, Q. Li, L. Xie, Y. Wang, Z. Rao, C. F. Qin, X. Wang, Structural basis for neutralization of SARS-CoV-2 and SARS-CoV by a potent therapeutic antibody. *Science* 369, 1505-1509 (2020).
25. D. Zhou, H. M. E. Duyvesteyn, C. P. Chen, C. G. Huang, T. H. Chen, S. R. Shih, Y. C. Lin, C. Y. Cheng, S. H. Cheng, Y. C. Huang, T. Y. Lin, C. Ma, J. Huo, L. Carrique, T. Malinauskas, R. R. Ruza, P. N. M. Shah, T. K. Tan, P. Rijal, R. F. Donat, K. Godwin, K. R. Buttigieg, J. A. Tree, J. Radecke, N. G. Paterson, P. Supasa, J. Mongkolsapaya, G. R. Screaton, M. W. Carroll, J. Gilbert-Jaramillo, M. L. Knight, W. James, R. J. Owens, J. H. Naismith, A. R. Townsend, E. E. Fly, Y. Zhao, J. Ren, D. I. Stuart, K. A. Huang, Structural basis for the neutralization of SARS-CoV-2 by an antibody from a convalescent patient. *Nat Struct Mol Biol* 27, 950-958 (2020).
26. J. Huo, A. Le Bas, R. R. Ruza, H. M. E. Duyvesteyn, H. Mikolajek, T. Malinauskas, T. K. Tan, P. Rijal, M. Dumoux, P. N. Ward, J. Ren, D. Zhou, P. J. Harrison, M. Weckener, D. K. Clare, V. K. Vogirala, J. Radecke, L. Moynie, Y. Zhao, J. Gilbert-Jaramillo, M. L. Knight, J. A. Tree, K. R. Buttigieg, N. Coombes, M. J. Elmore, M. W. Carroll, L. Carrique, P. N. M. Shah, W. James, A. R. Townsend, D. I. Stuart, R. J. Owens, J. H. Naismith, Neutralizing nanobodies bind SARS-CoV-2 spike RBD and block interaction with ACE2. *Nat Struct Mol Biol* 27, 846-854 (2020).
27. D. Pinto, Y. J. Park, M. Beltramello, A. C. Walls, M. A. Tortorici, S. Bianchi, S. Jaconi, K. Culap, F. Zatta, A. De Marco, A. Peter, B. Guarino, R. Spreafico, E. Cameroni, J. B. Case, R. E. Chen, C. Havenar-Daughton, G. Snell, A. Telenti, H. W. Virgin, A. Lanzavecchia, M. S. Diamond, K. Fink, D. Veesler, D. Corti, Cross-neutralization of SARS-CoV-2 by a human monoclonal SARS-CoV antibody. *Nature* 583, 290-295 (2020).
28. S. Xiong, Y. F. Wang, M. Y. Zhang, X. J. Liu, C. H. Zhang, S. S. Liu, C. W. Qian, J. X. Li, J. H. Lu, Z. Y. Wan, H. Y. Zheng, X. G. Yan, M. J. Meng, J. L. Fan, Immunogenicity of SARS inactivated vaccine in BALB/c mice. *Immunol Lett* 95, 139-143 (2004).
29. Y. He, Y. Zhou, P. Siddiqui, S. Jiang, Inactivated SARS-CoV vaccine elicits high titers of spike protein-specific antibodies that block receptor binding and virus entry. *Biochem Biophys Res Commun* 325, 445-452 (2004).
30. N. Takasuka, H. Fujii, Y. Takahashi, M. Kasai, S. Morikawa, S. Itamura, K. Ishii, M. Sakaguchi, K. Ohnishi, M. Ohshima, S. Hashimoto, M. Odagiri, M. Tashiro, H. Yoshikura, T. Takemori, Y. Tsunetsugu-Yokota, A subcutaneously injected UV-inactivated SARS coronavirus vaccine elicits systemic humoral immunity in mice. *Int Immunol* 16, 1423-1430 (2004).
31. L. Tang, Q. Zhu, E. Qin, M. Yu, Z. Ding, H. Shi, X. Cheng, C. Wang, G. Chang, Q. Zhu, F. Fang, H. Chang, S. Li, X. Zhang, X. Chen, J. Yu, J. Wang, Z. Chen, Inactivated SARS-CoV vaccine prepared from whole virus induces a high level of neutralizing antibodies in BALB/c mice. *DNA Cell Biol* 23, 391-394 (2004).
32. D. Qu, B. Zheng, X. Yao, Y. Guan, Z. H. Yuan, N. S. Zhong, L. W. Lu, J. P. Xie, Y. M. Wen, Intranasal immunization with inactivated SARS-CoV (SARS-asso- ciated coronavirus) induced local and serum antibodies in mice. *Vaccine* 23, 924-931 (2005).
33. C. H. Zhang, J. H. Lu, Y. F. Wang, H. Y. Zheng, S. Xiong, M. Y. Zhang, X. J. Liu, J. X. Li, Z. Y. Wan, X. G. Yan, S. Y. Qi, Z. Cui, B. Zhang, Immune responses in Balb/c mice induced by a candidate SARS-CoV inactivated vaccine prepared from F69 strain. *Vaccine* 23, 3196-3201 (2005).
34. E. W. Lamirande, M. L. DeDiego, A. Roberts, J. P. Jackson, E. Alvarez, T. Sheahan, W. J. Shieh, S. R. Zaki, R. Baric, L. Enjuanes, K. Subbarao, A live attenuated severe acute respiratory syndrome coronavirus is immunogenic and efficacious in golden Syrian hamsters. *J Virol* 82, 7721-7724 (2008).
35. Z. Y. Yang, W. P. Kong, Y. Huang, A. Roberts, B. R. Murphy, K. Subbarao, G. J. Nabel, A DNA vaccine induces SARS coronavirus neutralization and protective immunity in mice. *Nature* 428, 561-564 (2004).
36. F. Zeng, K. Y. Chow, C. C. Hon, K. M. Law, C. W. Yip, K. H. Chan, J. S. Peiris, F. C. Leung, Characterization of humoral responses in mice immunized with plasmid DNAs encoding SARS-CoV spike gene fragments. *Biochem Biophys Res Commun* 315, 1134-1139 (2004).
37. A. N. Zakhartchouk, S. Viswanathan, I. Moshynskyy, M. Petric, L. A. Babiuk, Optimization of a DNA vaccine against SARS. *DNA Cell Biol* 26, 721-726 (2007).
38. B. Callendret, V. Lorin, P. Charneau, P. Marianneau, H. Contamin, J. M. Betton, S. van der Werf, N. Escriou, Heterologous viral RNA export elements improve expression of severe acute respiratory syndrome (SARS) coronavirus spike protein and protective efficacy of DNA vaccines against SARS. *Virology* 363, 288-302 (2007).
39. H. Bisht, A. Roberts, L. Vogel, A. Bukreyev, P. L. Collins, B. R. Murphy, K. Subbarao, B. Moss, Severe acute respiratory syndrome coronavirus spike protein expressed by attenuated vaccinia virus protectively immunizes mice. *Proc Natl Acad Sci USA* 101, 6641-6646 (2004).
40. Z. Cao, L. Liu, L. Du, C. Zhang, S. Jiang, T. Li, Y. He, Potent and persistent antibody responses against the receptor-binding domain of SARS-CoV spike protein in recovered patients. *Virol J* 7, 299 (2010).
41. X. Zhu, Q. Liu, L. Du, L. Lu, S. Jiang, Receptor-binding domain as a target for developing SARS vaccines. *J Thorac Dis* 5 Suppl 2, S142-148 (2013).
42. H. Wang, Y. Zhang, B. Huang, W. Deng, Y. Quan, W. Wang, W. Xu, Y. Zhao, N. Li, J. Zhang, H. Liang, L. Bao, Y. Xu, L. Ding, W. Zhou, H. Gao, J. Liu, P. Niu, L. Zhao, W. Zhen, H. Fu, S. Yu, Z. Zhang, G. Xu, C. Li, Z. Lou, M. Xu, C. Qin, G. Wu, G. F. Gao, W. Tan, X. Yang, Development of an Inactivated Vaccine Candidate, BBIBP-CorV, with Potent Protection against SARS-CoV-2. *Cell* 182, 713-721 e719 (2020).
43. Q. Gao, L. Bao, H. Mao, L. Wang, K. Xu, M. Yang, Y. Li, L. Zhu, N. Wang, Z. Lv, H. Gao, X. Ge, B. Kan, Y. Hu, J. Liu, F. Cai, D. Jiang, Y. Yin, C. Qin, J. Li, X. Gong, X. Lou, W. Shi, D. Wu, H. Zhang, L. Zhu, W. Deng, Y. Li, J. Lu, C. Li, X. Wang, W. Yin, Y. Zhang, C. Qin, Development of an inactivated vaccine candidate for SARS-CoV-2. *Science* 369, 77-81 (2020).
44. K. S. Corbett, B. Flynn, K. E. Foulds, J. R. Francica, S. Boyoglu-Barnum, A. P. Werner, B. Flach, S. O'Connell, K. W. Bock, M. Minai, B. M. Nagata, H. Andersen, D. R. Martinez, A. T. Noe, N. Douek, M. M. Donaldson, N. N. Nji, G. S. Alvarado, D. K. Edwards, D. R. Flebbe, E. Lamb, N. A. Doria-Rose, B. C. Lin, M. K. Louder, S. O'Dell, S. D. Schmidt, E. Phung, L. A. Chang, C. Yap, J. M. Todd, L. Pessaint, A. Van Ry, S. Browne, J. Greenhouse, T. Putman-Taylor, A. Strasbaugh, T. A. Campbell, A. Cook, A. Dodson, K. Steingrebe, W. Shi, Y. Zhang, O. M. Abiona, L. Wang, A. Pegu, E. S. Yang, K. Leung, T. Zhou, I. T. Teng, A. Widge, I. Gordon, L. Novik, R. A. Gillespie, R. J. Loomis, J. I. Moliva, G. Stewart-Jones, S. Himansu, W. P. Kong, M. C. Nason, K. M. Morabito, T. J. Ruckwardt, J. E. Ledgerwood, M. R. Gaudinski, P. D. Kwong, J. R. Mascola, A. Carfi, M. G. Lewis, R. S. Baric, A. McDermott, I. N. Moore, N. J. Sullivan, M. Roederer, R. A. Seder, B. S. Graham, Evaluation of the mRNA-1273 Vaccine against SARS-CoV-2 in Nonhuman Primates. *N Engl J Med* 383, 1544-1555 (2020).

45. J. Yu, L. H. Tostanoski, L. Peter, N. B. Mercado, K. McMahan, S. H. Mahrokhian, J. P. Nkolola, J. Liu, Z. Li, A. Chandrashekar, D. R. Martinez, C. Loos, C. Atyeo, S. Fischinger, J. S. Burke, M. D. Slein, Y. Chen, A. Zuiani, F. J. N. Lelis, M. Travers, S. Habibi, L. Pessaint, A. Van Ry, K. Blade, R. Brown, A. Cook, B. Finneyfrock, A. Dodson, E. Teow, J. Velasco, R. Zahn, F. Wegmann, E. A. Bondzie, G. Dagotto, M. S. Gebre, X. He, C. Jacob-Dolan, M. Kirilova, N. Kordana, Z. Lin, L. F. Maxfield, F. Nampanya, R. Nityanandam, J. D. Ventura, H. Wan, Y. Cai, B. Chen, A. G. Schmidt, D. R. Wesemann, R. S. Baric, G. Alter, H. Andersen, M. G. Lewis, D. H. Barouch, DNA vaccine protection against SARS-CoV-2 in rhesus macaques. *Science* 369, 806-811 (2020).

46. N. van Doremalen, T. Lambe, A. Spencer, S. Belij-Rammerstorfer, J. N. Purushotham, J. R. Port, V. A. Avanzato, T. Bushmaker, A. Flaxman, M. Ulaszewska, F. Feldmann, E. R. Allen, H. Sharpe, J. Schulz, M. Holbrook, A. Okumura, K. Meade-White, K. Perez-Perez, N. J. Edwards, D. Wright, C. Bissett, C. Gilbride, B. N. Williamson, R. Rosenke, D. Long, A. Ishwarbhai, R. Kailath, L. Rose, S. Morris, C. Powers, J. Lovaglio, P. W. Hanley, D. Scott, G. Saturday, E. de Wit, S. C. Gilbert, V. J. Munster, ChAdOx1 nCoV-19 vaccine prevents SARS-CoV-2 pneumonia in rhesus macaques. *Nature* 586, 578-582 (2020).

47. N. B. Mercado, R. Zahn, F. Wegmann, C. Loos, A. Chandrashekar, J. Yu, J. Liu, L. Peter, K. McMahan, L. H. Tostanoski, X. He, D. R. Martinez, L. Rutten, R. Bos, D. van Manen, J. Vellinga, J. Custers, J. P. Langedijk, T. Kwaks, M. J. G. Bakkers, D. Zuijdgeest, S. K. Rosendahl Huber, C. Atyeo, S. Fischinger, J. S. Burke, J. Feldman, B. M. Hauser, T. M. Caradonna, E. A. Bondzie, G. Dagotto, M. S. Gebre, E. Hoffman, C. Jacob-Dolan, M. Kirilova, Z. Li, Z. Lin, S. H. Mahrokhian, L. F. Maxfield, F. Nampanya, R. Nityanandam, J. P. Nkolola, S. Patel, J. D. Ventura, K. Verrington, H. Wan, L. Pessaint, A. Van Ry, K. Blade, A. Strasbaugh, M. Cabus, R. Brown, A. Cook, S. Zouantchangadou, E. Teow, H. Andersen, M. G. Lewis, Y. Cai, B. Chen, A. G. Schmidt, R. K. Reeves, R. S. Baric, D. A. Lauffenburger, G. Alter, P. Stoffels, M. Mammen, J. Van Hoof, H. Schuitemaker, D. H. Barouch, Single-shot Ad26 vaccine protects against SARS-CoV-2 in rhesus macaques. *Nature*, (2020).

48. J. Yang, W. Wang, Z. Chen, S. Lu, F. Yang, Z. Bi, L. Bao, F. Mo, X. Li, Y. Huang, W. Hong, Y. Yang, Y. Zhao, F. Ye, S. Lin, W. Deng, H. Chen, H. Lei, Z. Zhang, M. Luo, H. Gao, Y. Zheng, Y. Gong, X. Jiang, Y. Xu, Q. Lv, D. Li, M. Wang, F. Li, S. Wang, G. Wang, P. Yu, Y. Qu, L. Yang, H. Deng, A. Tong, J. Li, Z. Wang, J. Yang, G. Shen, Z. Zhao, Y. Li, J. Luo, H. Liu, W. Yu, M. Yang, J. Xu, J. Wang, H. Li, H. Wang, D. Kuang, P. Lin, Z. Hu, W. Guo, W. Cheng, Y. He, X. Song, C. Chen, Z. Xue, S. Yao, L. Chen, X. Ma, S. Chen, M. Gou, W. Huang, Y. Wang, C. Fan, Z. Tian, M. Shi, F. S. Wang, L. Dai, M. Wu, G. Li, G. Wang, Y. Peng, Z. Qian, C. Huang, J. Y. Lau, Z. Yang, Y. Wei, X. Cen, X. Peng, C. Qin, K. Zhang, G. Lu, X. Wei, A vaccine targeting the RBD of the S protein of SARS-CoV-2 induces protective immunity. *Nature* 586, 572-577 (2020).

49. X. Liu, A. Drelich, W. Li, C. Chen, Z. Sun, M. Shi, C. Adams, J. W. Mellors, C. T. Tseng, D. S. Dimitrov, Enhanced elicitation of potent neutralizing antibodies by the SARS-CoV-2 spike receptor binding domain Fc fusion protein in mice. *Vaccine* 38, 7205-7212 (2020).

50. L. Dai, T. Zheng, K. Xu, Y. Han, L. Xu, E. Huang, Y. An, Y. Cheng, S. Li, M. Liu, M. Yang, Y. Li, H. Cheng, Y. Yuan, W. Zhang, C. Ke, G. Wong, J. Qi, C. Qin, J. Yan, G. F. Gao, A Universal Design of Betacoronavirus Vaccines against COVID-19, MERS, and SARS. *Cell* 182, 722-733 e711 (2020).

51. W. C. Huang, S. Zhou, X. He, K. Chiem, M. T. Mabrouk, R. H. Nissly, I. M. Bird, M. Strauss, S. Sambhara, J. Ortega, E. A. Wohlfert, L. Martinez-Sobrido, S. V. Kuchipudi, B. A. Davidson, J. F. Lovell, SARS-CoV-2 RBD Neutralizing Antibody Induction is Enhanced by Particulate Vaccination. *Adv Mater,* e2005637 (2020).

52. W. Tai, X. Zhang, A. Drelich, J. Shi, J. C. Hsu, L. Luchsinger, C. D. Hillyer, C. K. Tseng, S. Jiang, L. Du, A novel receptor-binding domain (RBD)-based mRNA vaccine against SARS-CoV-2. *Cell Res,* (2020).

53. M. J. Mulligan, K. E. Lyke, N. Kitchin, J. Absalon, A. Gurtman, S. Lockhart, K. Neuzil, V. Raabe, R. Bailey, K. A. Swanson, P. Li, K. Koury, W. Kalina, D. Cooper, C. Fontes-Garfias, P. Y. Shi, O. Tureci, K. R. Tompkins, E. E. Walsh, R. Frenck, A. R. Falsey, P. R. Dormitzer, W. C. Gruber, U. Sahin, K. U. Jansen, Phase I/II study of COVID-19 RNA vaccine BNT162b1 in adults. *Nature* 586, 589-593 (2020).

54. P. G. Seferian, M. L. Martinez, Immune stimulating activity of two new chitosan containing adjuvant formulations. *Vaccine* 19, 661-668 (2000).

TABLE OF SEQUENCES

SEQ ID NO: 3 - Linker-RBD-Linker-6xHis
KLTGGTTNLCPFGEVFNATRFASVYAWNRKRISNCVADYSVLYNSASFST
FKCYGVSPTKLNDLCFTNVYADSFVIRGDEVRQIAPGQTGKIADYNYKLP
DDFTGCVIAWNSNNLDSKVGGNYNYLYRLFRKSNLKPFERDISTEIYQAG
STPCNGVEGFNCYFPLQSYGFQPTNGVGYQPYRVVVLSFELLHAPATVCG
PKGPGMHHHHHH SEQ ID NO: 45 - RBD (from $T^{333}$ to $K^{528}$ of the S protein)
TNLCPFGEVFNATRFASVYAWNRKRISNCVADYSVLYNSASFSTFKCYGV
SPTKLNDLCFTNVYADSFVIRGDEVRQIAPGQTGKIADYNYKLPDDFTGC
VIAWNSNNLDSKVGGNYNYLYRLFRKSNLKPFERDISTEIYQAGSTPCNG
VEGFNCYFPLQSYGFQPTNGVGYQPYRVVVLSFELLHAPATVCGPK SEQ ID NO: 4 - RBM
SNNLDSKVGGNYNYLYRLFRKSNLKPFERDISTEIYQAGSTPCNGVEGFN
CYFPLQSYGFQPTNGVGYQ Overlapping Epitopes left to right in FIG. 9

| | |
|---|---|
| SNFRVQPTESIVRFPNI | SEQ ID NO: 5 |
| TESIVRFPNITNLCPFGE | SEQ ID NO: 6 |
| PNITNLCPFGEVFNATR | SEQ ID NO: 7 |
| PFGEVFNATRFASVYAW | SEQ ID NO: 8 |
| ATRFASVYAWNRKRISN *50 | SEQ ID NO: 9 |
| YAWNRKRISNCVADYSV | SEQ ID NO: 10 |
| ISNCVADYSVLYNSASF | SEQ ID NO: 11 |
| SVLYNSASFSTFKCYG | SEQ ID NO: 12 |
| ASFSTFKCYGVSPTKLN *54 | SEQ ID NO: 13 |
| CYGVSPTKLNDLCFTNV *55 | SEQ ID NO: 14 |
| KLNDLCFTNVYADSFVI | SEQ ID NO: 15 |

TABLE OF SEQUENCES

| | |
|---|---|
| TNVYADSFVIRGDEVRQ *57 | SEQ ID NO: 16 |
| FVIRGDEVRQIAPGQTG | SEQ ID NO: 17 |
| VRQIAPGQTGKIADYNY *59 | SEQ ID NO: 18 |
| QTGKIADYNYKLPDDFT | SEQ ID NO: 19 |
| YNYKLPDDFTGCVIAWN *61 | SEQ ID NO: 20 |
| DFTGCVIAWNSNNLDSK | SEQ ID NO: 21 |
| AWNSNNLDSKVGGNYNY | SEQ ID NO: 22 |
| DSKVGGNYNYLYRLFRK | SEQ ID NO: 23 |
| YNYLYRLFRKSNLKPFE | SEQ ID NO: 24 |
| FRKSNLKPFERDISTEI *66 | SEQ ID NO: 25 |
| PFERDISTEIYQAGSTP | SEQ ID NO: 26 |
| TEIYQAGSTPCNGVEGF *68 | SEQ ID NO: 27 |
| STPCNGVEGFNCYFPLQ | SEQ ID NO: 28 |
| EGFNCYFPLQSYGFQPT | SEQ ID NO: 29 |
| PLQSYGFQPTNGVGYQP | SEQ ID NO: 30 |
| YQPYRVVVLSFELLHAP | SEQ ID NO: 31 |
| VLSFELLHAPATVCGPK *74 | SEQ ID NO: 32 |
| HAPATVCGPKKSTNLVK | SEQ ID NO: 33 |

Overlapping epitopes left to right in FIG. 10

| | |
|---|---|
| TNLCPFGEVFNATRFA P1 | SEQ ID NO: 34 |
| EVFNATRFASVYAWNRKRISN *P2 | SEQ ID NO: 35 |
| DYSVLYNSASFSTFKCYGVSPTKLND *P3 | SEQ ID NO: 36 |
| DEVRQIAPGQTGKIADYNYKLPDDF *P4 | SEQ ID NO: 37 |
| WNSNNLDSKVGGNYNYL P5 | SEQ ID NO: 38 |
| RKSNLKPFERDISTEIYQAGSTP *P6 | SEQ ID NO: 39 |
| STEIYQAGSTPCNGVEGFNCYFPL *P7 | SEQ ID NO: 40 |
| VEGFNCYFPLQSYGFQPTNGVGYQPY P8 | SEQ ID NO: 41 |
| ELLHAPATVCGPKGPGMHHHHHH *P9 | SEQ ID NO: 42 |

SEQ ID NO: 59 - Nucleic acid sequence encoding SEQ ID NO: 1
Signal Peptide (Italics)
Linker (BOLD)
SARS-CoV-2 RBD (underlined)
Linker (BOLD)
6xhis Tag (italics, bold)
*ATGGGAATACTTCCTTCCCCTGGTATGCCTGCGCTTCTTTCACTCGTGTC*
*CCTTCTTAGCGTACTTCTCATGGGCTGCGTCGCCGAA*AAGCTTACCGGTG
GTACCACAAATCTCTGCCCATTTGGGGAAGTTTTCAATGCGACAAGATTC
GCTAGTGTCTACGCATGGAACCGGAAACGAATCAGCAACTGCGTAGCGGA
TTACTCCGTCTTGTATAATTCCGCGTCATTCTCTACGTTCAAGTGCTATG
GTGTATCCCCCACCAAACTCAACGACTTGTGCTTTACGAATGTCTATGCC
GATTCATTCGTTATACGCGGAGACGAGGTAAGACAAATAGCTCCAGGGCA
GACCGGGAAAATTGCGGATTATAACTACAAACTGCCAGACGACTTTACTG
GGTGTGTTATCGCCTGGAACAGTAACAATTTGGACTCCAAAGTCGGGGGT
AACTATAATTACTTGTATAGACTGTTCCGCAAAAGCAATCTCAAACCCTT
CGAGCGGGATATTTCCACCGAGATTTATCAGGCGGGGAGTACTCCATGCA
ATGGGGTTGAGGGATTTAACTGCTATTTTCCATTGCAATCTTACGGTTTC
CAGCCTACGAATGGAGTCGGATATCAACCCTACAGGGTCGTCGTGCTGTC
ATTTGAACTCCTGCATGCCCCCGCTACTGTCTGCGGGCCAAAGGGGCCCG
GGATG*CATCACCATCATCACCAT*

SEQ ID NO: 60 - Nucleic acid sequence encoding SEQ ID NO: 3
AAGCTTACCGGTGGTACCACAAATCTCTGCCCATTTGGGGAAGTTTTCAA
TGCGACAAGATTCGCTAGTGTCTACGCATGGAACCGGAAACGAATCAGCA
ACTGCGTAGCGGATTACTCCGTCTTGTATAATTCCGCGTCATTCTCTACG
TTCAAGTGCTATGGTGTATCCCCCACCAAACTCAACGACTTGTGCTTTAC
GAATGTCTATGCCGATTCATTCGTTATACGCGGAGACGAGGTAAGACAAA
TAGCTCCAGGGCAGACCGGGAAAATTGCGGATTATAACTACAAACTGCCA
GACGACTTTACTGGGTGTGTTATCGCCTGGAACAGTAACAATTTGGACTC
CAAAGTCGGGGGTAACTATAATTACTTGTATAGACTGTTCCGCAAAAGCA
ATCTCAAACCCTTCGAGCGGGATATTTCCACCGAGATTTATCAGGCGGGG
AGTACTCCATGCAATGGGGTTGAGGGATTTAACTGCTATTTTCCATTGCA
ATCTTACGGTTTCCAGCCTACGAATGGAGTCGGATATCAACCCTACAGGG
TCGTCGTGCTGTCATTTGAACTCCTGCATGCCCCCGCTACTGTCTGCGGG
CCAAAGGGGCCCGGGATGCATCACCATCATCACCAT SEQ ID NO: 61 - RBD nucleic acid sequence encoding SEQ ID NO: 45
ACAAATCTCTGCCCATTTGGGGAAGTTTTCAATGCGACAAGATTCGCTAG
TGTCTACGCATGGAACCGGAAACGAATCAGCAACTGCGTAGCGGATTACT
CCGTCTTGTATAATTCCGCGTCATTCTCTACGTTCAAGTGCTATGGTGTA
TCCCCCACCAAACTCAACGACTTGTGCTTTACGAATGTCTATGCCGATTC
ATTCGTTATACGCGGAGACGAGGTAAGACAAATAGCTCCAGGGCAGACCG
GGAAAATTGCGGATTATAACTACAAACTGCCAGACGACTTTACTGGGTGT
GTTATCGCCTGGAACAGTAACAATTTGGACTCCAAAGTCGGGGGTAACTA
TAATTACTTGTATAGACTGTTCCGCAAAAGCAATCTCAAACCCTTCGAGC
GGGATATTTCCACCGAGATTTATCAGGCGGGGAGTACTCCATGCAATGGG
GTTGAGGGATTTAACTGCTATTTTCCATTGCAATCTTACGGTTTCCAGCC
TACGAATGGAGTCGGATATCAACCCTACAGGGTCGTCGTGCTGTCATTTG
AACTCCTGCATGCCCCCGCTACTGTCTGCGGGCCAAAG SEQ ID NO: 62 - RBM nucleic acid sequence encoding SEQ ID NO: 4
AGTAACAATTTGGACTCCAAAGTCGGGGGTAACTATAATTACTTGTATAG
ACTGTTCCGCAAAAGCAATCTCAAACCCTTCGAGCGGGATATTTCCACCG
AGATTTATCAGGCGGGGAGTACTCCATGCAATGGGGTTGAGGGATTTAAC
TGCTATTTTCCATTGCAATCTTACGGTTTCCAGCCTACGAATGGAGTCGG
ATATCAA

SEQUENCE LISTING

<160> NUMBER OF SEQ ID NOS: 62

<210> SEQ ID NO 1
<211> LENGTH: 241
<212> TYPE: PRT
<213> ORGANISM: Artificial Sequence
<220> FEATURE:
<223> OTHER INFORMATION: Synthetic construct

<400> SEQUENCE: 1

```
Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Lys Leu Thr
            20                  25                  30

Gly Gly Thr Thr Asn Leu Cys Pro Phe Gly Glu Val Phe Asn Ala Thr
        35                  40                  45

Arg Phe Ala Ser Val Tyr Ala Trp Asn Arg Lys Arg Ile Ser Asn Cys
    50                  55                  60

Val Ala Asp Tyr Ser Val Leu Tyr Asn Ser Ala Ser Phe Ser Thr Phe
```

```
                65                  70                  75                  80
Lys Cys Tyr Gly Val Ser Pro Thr Lys Leu Asn Asp Leu Cys Phe Thr
                    85                  90                  95

Asn Val Tyr Ala Asp Ser Phe Val Ile Arg Gly Asp Glu Val Arg Gln
                100                 105                 110

Ile Ala Pro Gly Gln Thr Gly Lys Ile Ala Asp Tyr Asn Tyr Lys Leu
                115                 120                 125

Pro Asp Asp Phe Thr Gly Cys Val Ile Ala Trp Asn Ser Asn Asn Leu
130                 135                 140

Asp Ser Lys Val Gly Gly Asn Tyr Asn Tyr Leu Tyr Arg Leu Phe Arg
145                 150                 155                 160

Lys Ser Asn Leu Lys Pro Phe Glu Arg Asp Ile Ser Thr Glu Ile Tyr
                165                 170                 175

Gln Ala Gly Ser Thr Pro Cys Asn Gly Val Glu Gly Phe Asn Cys Tyr
                180                 185                 190

Phe Pro Leu Gln Ser Tyr Gly Phe Gln Pro Thr Asn Gly Val Gly Tyr
                195                 200                 205

Gln Pro Tyr Arg Val Val Val Leu Ser Phe Glu Leu Leu His Ala Pro
                210                 215                 220

Ala Thr Val Cys Gly Pro Lys Gly Pro Gly Met His His His His His
225                 230                 235                 240

His

<210> SEQ ID NO 2
<211> LENGTH: 1273
<212> TYPE: PRT
<213> ORGANISM: Severe acute respiratory syndrome coronavirus 2
<220> FEATURE:
<221> NAME/KEY: misc_feature
<222> LOCATION: (22)..(49)
<223> OTHER INFORMATION: Xaa can be any naturally occurring amino acid

<400> SEQUENCE: 2

Met Phe Val Phe Leu Val Leu Leu Pro Leu Val Ser Ser Gln Cys Val
1               5                   10                  15

Asn Leu Thr Thr Arg Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
                35                  40                  45

Xaa Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
                100                 105                 110

Lys Thr Gln Ser Leu Leu Ile Val Asn Asn Ala Thr Asn Val Val Ile
                115                 120                 125

Lys Val Cys Glu Phe Gln Phe Cys Asn Asp Pro Phe Leu Gly Val Tyr
                130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175
```

```
Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
        210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
        290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
        370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
        450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
        530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
```

```
                595                 600                 605
        Ala Val Leu Tyr Gln Asp Val Asn Cys Thr Glu Val Pro Val Ala Ile
        610                 615                 620

His Ala Asp Gln Leu Thr Pro Thr Trp Arg Val Tyr Ser Thr Gly Ser
        625                 630                 635                 640

Asn Val Phe Gln Thr Arg Ala Gly Cys Leu Ile Gly Ala Glu His Val
                        645                 650                 655

Asn Asn Ser Tyr Glu Cys Asp Ile Pro Ile Gly Ala Gly Ile Cys Ala
                        660                 665                 670

Ser Tyr Gln Thr Gln Thr Asn Ser Pro Arg Arg Ala Arg Ser Val Ala
                        675                 680                 685

Ser Gln Ser Ile Ile Ala Tyr Thr Met Ser Leu Gly Ala Glu Asn Ser
        690                 695                 700

Val Ala Tyr Ser Asn Asn Ser Ile Ala Ile Pro Thr Asn Phe Thr Ile
        705                 710                 715                 720

Ser Val Thr Thr Glu Ile Leu Pro Val Ser Met Thr Lys Thr Ser Val
                        725                 730                 735

Asp Cys Thr Met Tyr Ile Cys Gly Asp Ser Thr Glu Cys Ser Asn Leu
                        740                 745                 750

Leu Leu Gln Tyr Gly Ser Phe Cys Thr Gln Leu Asn Arg Ala Leu Thr
                        755                 760                 765

Gly Ile Ala Val Glu Gln Asp Lys Asn Thr Gln Glu Val Phe Ala Gln
        770                 775                 780

Val Lys Gln Ile Tyr Lys Thr Pro Pro Ile Lys Asp Phe Gly Gly Phe
        785                 790                 795                 800

Asn Phe Ser Gln Ile Leu Pro Asp Pro Ser Lys Pro Ser Lys Arg Ser
                        805                 810                 815

Phe Ile Glu Asp Leu Leu Phe Asn Lys Val Thr Leu Ala Asp Ala Gly
                        820                 825                 830

Phe Ile Lys Gln Tyr Gly Asp Cys Leu Gly Asp Ile Ala Ala Arg Asp
                        835                 840                 845

Leu Ile Cys Ala Gln Lys Phe Asn Gly Leu Thr Val Leu Pro Pro Leu
        850                 855                 860

Leu Thr Asp Glu Met Ile Ala Gln Tyr Thr Ser Ala Leu Leu Ala Gly
        865                 870                 875                 880

Thr Ile Thr Ser Gly Trp Thr Phe Gly Ala Gly Ala Ala Leu Gln Ile
                        885                 890                 895

Pro Phe Ala Met Gln Met Ala Tyr Arg Phe Asn Gly Ile Gly Val Thr
                        900                 905                 910

Gln Asn Val Leu Tyr Glu Asn Gln Lys Leu Ile Ala Asn Gln Phe Asn
                        915                 920                 925

Ser Ala Ile Gly Lys Ile Gln Asp Ser Leu Ser Ser Thr Ala Ser Ala
        930                 935                 940

Leu Gly Lys Leu Gln Asp Val Val Asn Gln Asn Ala Gln Ala Leu Asn
        945                 950                 955                 960

Thr Leu Val Lys Gln Leu Ser Ser Asn Phe Gly Ala Ile Ser Ser Val
                        965                 970                 975

Leu Asn Asp Ile Leu Ser Arg Leu Asp Lys Val Glu Ala Glu Val Gln
                        980                 985                 990

Ile Asp Arg Leu Ile Thr Gly Arg Leu Gln Ser Leu Gln Thr Tyr Val
                        995                 1000                1005

Thr Gln Gln Leu Ile Arg Ala Ala Glu Ile Arg Ala Ser Ala Asn
                1010                1015                1020
```

```
Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Asp Ser Glu Pro
    1250                1255                1260

Val Leu Lys Gly Val Lys Leu His Tyr Thr
    1265                1270

<210> SEQ ID NO 3
<211> LENGTH: 212
<212> TYPE: PRT
<213> ORGANISM: Artificial Sequence
<220> FEATURE:
<223> OTHER INFORMATION: Synthetic construct

<400> SEQUENCE: 3

Lys Leu Thr Gly Gly Thr Thr Asn Leu Cys Pro Phe Gly Glu Val Phe
1               5                   10                  15

Asn Ala Thr Arg Phe Ala Ser Val Tyr Ala Trp Asn Arg Lys Arg Ile
            20                  25                  30

Ser Asn Cys Val Ala Asp Tyr Ser Val Leu Tyr Asn Ser Ala Ser Phe
        35                  40                  45

Ser Thr Phe Lys Cys Tyr Gly Val Ser Pro Thr Lys Leu Asn Asp Leu
    50                  55                  60

Cys Phe Thr Asn Val Tyr Ala Asp Ser Phe Val Ile Arg Gly Asp Glu
65                  70                  75                  80

Val Arg Gln Ile Ala Pro Gly Gln Thr Gly Lys Ile Ala Asp Tyr Asn
                85                  90                  95
```

Tyr Lys Leu Pro Asp Asp Phe Thr Gly Cys Val Ile Ala Trp Asn Ser
            100                 105                 110

Asn Asn Leu Asp Ser Lys Val Gly Gly Asn Tyr Asn Tyr Leu Tyr Arg
        115                 120                 125

Leu Phe Arg Lys Ser Asn Leu Lys Pro Phe Glu Arg Asp Ile Ser Thr
    130                 135                 140

Glu Ile Tyr Gln Ala Gly Ser Thr Pro Cys Asn Gly Val Glu Gly Phe
145                 150                 155                 160

Asn Cys Tyr Phe Pro Leu Gln Ser Tyr Gly Phe Gln Pro Thr Asn Gly
                165                 170                 175

Val Gly Tyr Gln Pro Tyr Arg Val Val Val Leu Ser Phe Glu Leu Leu
            180                 185                 190

His Ala Pro Ala Thr Val Cys Gly Pro Lys Gly Pro Gly Met His His
        195                 200                 205

His His His His
        210

<210> SEQ ID NO 4
<211> LENGTH: 69
<212> TYPE: PRT
<213> ORGANISM: Severe acute respiratory syndrome coronavirus 2

<400> SEQUENCE: 4

Ser Asn Asn Leu Asp Ser Lys Val Gly Gly Asn Tyr Asn Tyr Leu Tyr
1               5                   10                  15

Arg Leu Phe Arg Lys Ser Asn Leu Lys Pro Phe Glu Arg Asp Ile Ser
            20                  25                  30

Thr Glu Ile Tyr Gln Ala Gly Ser Thr Pro Cys Asn Gly Val Glu Gly
        35                  40                  45

Phe Asn Cys Tyr Phe Pro Leu Gln Ser Tyr Gly Phe Gln Pro Thr Asn
    50                  55                  60

Gly Val Gly Tyr Gln
65

<210> SEQ ID NO 5
<211> LENGTH: 17
<212> TYPE: PRT
<213> ORGANISM: Severe acute respiratory syndrome coronavirus 2

<400> SEQUENCE: 5

Ser Asn Phe Arg Val Gln Pro Thr Glu Ser Ile Val Arg Phe Pro Asn
1               5                   10                  15

Ile

<210> SEQ ID NO 6
<211> LENGTH: 18
<212> TYPE: PRT
<213> ORGANISM: Severe acute respiratory syndrome coronavirus 2

<400> SEQUENCE: 6

Thr Glu Ser Ile Val Arg Phe Pro Asn Ile Thr Asn Leu Cys Pro Phe
1               5                   10                  15

Gly Glu

<210> SEQ ID NO 7
<211> LENGTH: 17
<212> TYPE: PRT
<213> ORGANISM: Severe acute respiratory syndrome coronavirus 2

-continued

<400> SEQUENCE: 7

Pro Asn Ile Thr Asn Leu Cys Pro Phe Gly Glu Val Phe Asn Ala Thr
1               5                   10                  15

Arg

<210> SEQ ID NO 8
<211> LENGTH: 17
<212> TYPE: PRT
<213> ORGANISM: Severe acute respiratory syndrome coronavirus 2

<400> SEQUENCE: 8

Pro Phe Gly Glu Val Phe Asn Ala Thr Arg Phe Ala Ser Val Tyr Ala
1               5                   10                  15

Trp

<210> SEQ ID NO 9
<211> LENGTH: 17
<212> TYPE: PRT
<213> ORGANISM: Severe acute respiratory syndrome coronavirus 2

<400> SEQUENCE: 9

Ala Thr Arg Phe Ala Ser Val Tyr Ala Trp Asn Arg Lys Arg Ile Ser
1               5                   10                  15

Asn

<210> SEQ ID NO 10
<211> LENGTH: 17
<212> TYPE: PRT
<213> ORGANISM: Severe acute respiratory syndrome coronavirus 2

<400> SEQUENCE: 10

Tyr Ala Trp Asn Arg Lys Arg Ile Ser Asn Cys Val Ala Asp Tyr Ser
1               5                   10                  15

Val

<210> SEQ ID NO 11
<211> LENGTH: 17
<212> TYPE: PRT
<213> ORGANISM: Severe acute respiratory syndrome coronavirus 2

<400> SEQUENCE: 11

Ile Ser Asn Cys Val Ala Asp Tyr Ser Val Leu Tyr Asn Ser Ala Ser
1               5                   10                  15

Phe

<210> SEQ ID NO 12
<211> LENGTH: 16
<212> TYPE: PRT
<213> ORGANISM: Severe acute respiratory syndrome coronavirus 2

<400> SEQUENCE: 12

Ser Val Leu Tyr Asn Ser Ala Ser Phe Ser Thr Phe Lys Cys Tyr Gly
1               5                   10                  15

<210> SEQ ID NO 13
<211> LENGTH: 17
<212> TYPE: PRT
<213> ORGANISM: Severe acute respiratory syndrome coronavirus 2

<400> SEQUENCE: 13

Ala Ser Phe Ser Thr Phe Lys Cys Tyr Gly Val Ser Pro Thr Lys Leu
1               5                   10                  15
Asn

<210> SEQ ID NO 14
<211> LENGTH: 17
<212> TYPE: PRT
<213> ORGANISM: Severe acute respiratory syndrome coronavirus 2

<400> SEQUENCE: 14

Cys Tyr Gly Val Ser Pro Thr Lys Leu Asn Asp Leu Cys Phe Thr Asn
1               5                   10                  15
Val

<210> SEQ ID NO 15
<211> LENGTH: 17
<212> TYPE: PRT
<213> ORGANISM: Severe acute respiratory syndrome coronavirus 2

<400> SEQUENCE: 15

Lys Leu Asn Asp Leu Cys Phe Thr Asn Val Tyr Ala Asp Ser Phe Val
1               5                   10                  15
Ile

<210> SEQ ID NO 16
<211> LENGTH: 17
<212> TYPE: PRT
<213> ORGANISM: Severe acute respiratory syndrome coronavirus 2

<400> SEQUENCE: 16

Thr Asn Val Tyr Ala Asp Ser Phe Val Ile Arg Gly Asp Glu Val Arg
1               5                   10                  15
Gln

<210> SEQ ID NO 17
<211> LENGTH: 17
<212> TYPE: PRT
<213> ORGANISM: Severe acute respiratory syndrome coronavirus 2

<400> SEQUENCE: 17

Phe Val Ile Arg Gly Asp Glu Val Arg Gln Ile Ala Pro Gly Gln Thr
1               5                   10                  15
Gly

<210> SEQ ID NO 18
<211> LENGTH: 17
<212> TYPE: PRT
<213> ORGANISM: Severe acute respiratory syndrome coronavirus 2

<400> SEQUENCE: 18

Val Arg Gln Ile Ala Pro Gly Gln Thr Gly Lys Ile Ala Asp Tyr Asn
1               5                   10                  15
Tyr

<210> SEQ ID NO 19
<211> LENGTH: 17
<212> TYPE: PRT
<213> ORGANISM: Severe acute respiratory syndrome coronavirus 2

<400> SEQUENCE: 19

Gln Thr Gly Lys Ile Ala Asp Tyr Asn Tyr Lys Leu Pro Asp Asp Phe

```
<210> SEQ ID NO 20
<211> LENGTH: 17
<212> TYPE: PRT
<213> ORGANISM: Severe acute respiratory syndrome coronavirus 2

<400> SEQUENCE: 20

Tyr Asn Tyr Lys Leu Pro Asp Asp Phe Thr Gly Cys Val Ile Ala Trp
1               5                   10                  15
Asn

<210> SEQ ID NO 21
<211> LENGTH: 17
<212> TYPE: PRT
<213> ORGANISM: Severe acute respiratory syndrome coronavirus 2

<400> SEQUENCE: 21

Asp Phe Thr Gly Cys Val Ile Ala Trp Asn Ser Asn Asn Leu Asp Ser
1               5                   10                  15
Lys

<210> SEQ ID NO 22
<211> LENGTH: 17
<212> TYPE: PRT
<213> ORGANISM: Severe acute respiratory syndrome coronavirus 2

<400> SEQUENCE: 22

Ala Trp Asn Ser Asn Asn Leu Asp Ser Lys Val Gly Gly Asn Tyr Asn
1               5                   10                  15
Tyr

<210> SEQ ID NO 23
<211> LENGTH: 17
<212> TYPE: PRT
<213> ORGANISM: Severe acute respiratory syndrome coronavirus 2

<400> SEQUENCE: 23

Asp Ser Lys Val Gly Gly Asn Tyr Asn Tyr Leu Tyr Arg Leu Phe Arg
1               5                   10                  15
Lys

<210> SEQ ID NO 24
<211> LENGTH: 17
<212> TYPE: PRT
<213> ORGANISM: Severe acute respiratory syndrome coronavirus 2

<400> SEQUENCE: 24

Tyr Asn Tyr Leu Tyr Arg Leu Phe Arg Lys Ser Asn Leu Lys Pro Phe
1               5                   10                  15
Glu

<210> SEQ ID NO 25
<211> LENGTH: 17
<212> TYPE: PRT
<213> ORGANISM: Severe acute respiratory syndrome coronavirus 2

<400> SEQUENCE: 25

Phe Arg Lys Ser Asn Leu Lys Pro Phe Glu Arg Asp Ile Ser Thr Glu
1               5                   10                  15
```

Ile

<210> SEQ ID NO 26
<211> LENGTH: 17
<212> TYPE: PRT
<213> ORGANISM: Severe acute respiratory syndrome coronavirus 2

<400> SEQUENCE: 26

Pro Phe Glu Arg Asp Ile Ser Thr Glu Ile Tyr Gln Ala Gly Ser Thr
1               5                   10                  15

Pro

<210> SEQ ID NO 27
<211> LENGTH: 17
<212> TYPE: PRT
<213> ORGANISM: Severe acute respiratory syndrome coronavirus 2

<400> SEQUENCE: 27

Thr Glu Ile Tyr Gln Ala Gly Ser Thr Pro Cys Asn Gly Val Glu Gly
1               5                   10                  15

Phe

<210> SEQ ID NO 28
<211> LENGTH: 17
<212> TYPE: PRT
<213> ORGANISM: Severe acute respiratory syndrome coronavirus 2

<400> SEQUENCE: 28

Ser Thr Pro Cys Asn Gly Val Glu Gly Phe Asn Cys Tyr Phe Pro Leu
1               5                   10                  15

Gln

<210> SEQ ID NO 29
<211> LENGTH: 17
<212> TYPE: PRT
<213> ORGANISM: Severe acute respiratory syndrome coronavirus 2

<400> SEQUENCE: 29

Glu Gly Phe Asn Cys Tyr Phe Pro Leu Gln Ser Tyr Gly Phe Gln Pro
1               5                   10                  15

Thr

<210> SEQ ID NO 30
<211> LENGTH: 17
<212> TYPE: PRT
<213> ORGANISM: Severe acute respiratory syndrome coronavirus 2

<400> SEQUENCE: 30

Pro Leu Gln Ser Tyr Gly Phe Gln Pro Thr Asn Gly Val Gly Tyr Gln
1               5                   10                  15

Pro

<210> SEQ ID NO 31
<211> LENGTH: 17
<212> TYPE: PRT
<213> ORGANISM: Severe acute respiratory syndrome coronavirus 2

<400> SEQUENCE: 31

Tyr Gln Pro Tyr Arg Val Val Val Leu Ser Phe Glu Leu Leu His Ala
1               5                   10                  15

Pro

```
<210> SEQ ID NO 32
<211> LENGTH: 17
<212> TYPE: PRT
<213> ORGANISM: Severe acute respiratory syndrome coronavirus 2

<400> SEQUENCE: 32

Val Leu Ser Phe Glu Leu Leu His Ala Pro Ala Thr Val Cys Gly Pro
1               5                   10                  15

Lys

<210> SEQ ID NO 33
<211> LENGTH: 17
<212> TYPE: PRT
<213> ORGANISM: Severe acute respiratory syndrome coronavirus 2

<400> SEQUENCE: 33

His Ala Pro Ala Thr Val Cys Gly Pro Lys Lys Ser Thr Asn Leu Val
1               5                   10                  15

Lys

<210> SEQ ID NO 34
<211> LENGTH: 16
<212> TYPE: PRT
<213> ORGANISM: Severe acute respiratory syndrome coronavirus 2

<400> SEQUENCE: 34

Thr Asn Leu Cys Pro Phe Gly Glu Val Phe Asn Ala Thr Arg Phe Ala
1               5                   10                  15

<210> SEQ ID NO 35
<211> LENGTH: 21
<212> TYPE: PRT
<213> ORGANISM: Severe acute respiratory syndrome coronavirus 2

<400> SEQUENCE: 35

Glu Val Phe Asn Ala Thr Arg Phe Ala Ser Val Tyr Ala Trp Asn Arg
1               5                   10                  15

Lys Arg Ile Ser Asn
            20

<210> SEQ ID NO 36
<211> LENGTH: 26
<212> TYPE: PRT
<213> ORGANISM: Severe acute respiratory syndrome coronavirus 2

<400> SEQUENCE: 36

Asp Tyr Ser Val Leu Tyr Asn Ser Ala Ser Phe Ser Thr Phe Lys Cys
1               5                   10                  15

Tyr Gly Val Ser Pro Thr Lys Leu Asn Asp
            20                  25

<210> SEQ ID NO 37
<211> LENGTH: 25
<212> TYPE: PRT
<213> ORGANISM: Severe acute respiratory syndrome coronavirus 2

<400> SEQUENCE: 37

Asp Glu Val Arg Gln Ile Ala Pro Gly Gln Thr Gly Lys Ile Ala Asp
1               5                   10                  15

Tyr Asn Tyr Lys Leu Pro Asp Asp Phe
```

```
              20                  25

<210> SEQ ID NO 38
<211> LENGTH: 17
<212> TYPE: PRT
<213> ORGANISM: Severe acute respiratory syndrome coronavirus 2

<400> SEQUENCE: 38

Trp Asn Ser Asn Asn Leu Asp Ser Lys Val Gly Gly Asn Tyr Asn Tyr
1               5                   10                  15

Leu

<210> SEQ ID NO 39
<211> LENGTH: 23
<212> TYPE: PRT
<213> ORGANISM: Severe acute respiratory syndrome coronavirus 2

<400> SEQUENCE: 39

Arg Lys Ser Asn Leu Lys Pro Phe Glu Arg Asp Ile Ser Thr Glu Ile
1               5                   10                  15

Tyr Gln Ala Gly Ser Thr Pro
            20

<210> SEQ ID NO 40
<211> LENGTH: 24
<212> TYPE: PRT
<213> ORGANISM: Severe acute respiratory syndrome coronavirus 2

<400> SEQUENCE: 40

Ser Thr Glu Ile Tyr Gln Ala Gly Ser Thr Pro Cys Asn Gly Val Glu
1               5                   10                  15

Gly Phe Asn Cys Tyr Phe Pro Leu
            20

<210> SEQ ID NO 41
<211> LENGTH: 26
<212> TYPE: PRT
<213> ORGANISM: Severe acute respiratory syndrome coronavirus 2

<400> SEQUENCE: 41

Val Glu Gly Phe Asn Cys Tyr Phe Pro Leu Gln Ser Tyr Gly Phe Gln
1               5                   10                  15

Pro Thr Asn Gly Val Gly Tyr Gln Pro Tyr
            20                  25

<210> SEQ ID NO 42
<211> LENGTH: 23
<212> TYPE: PRT
<213> ORGANISM: Artificial Sequence
<220> FEATURE:
<223> OTHER INFORMATION: Synthetic construct

<400> SEQUENCE: 42

Glu Leu Leu His Ala Pro Ala Thr Val Cys Gly Pro Lys Gly Pro Gly
1               5                   10                  15

Met His His His His His His
            20

<210> SEQ ID NO 43
<211> LENGTH: 29
<212> TYPE: PRT
<213> ORGANISM: Artificial Sequence
<220> FEATURE:
```

```
<223> OTHER INFORMATION: Synthetic construct

<400> SEQUENCE: 43

Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu
            20                  25

<210> SEQ ID NO 44
<211> LENGTH: 6
<212> TYPE: PRT
<213> ORGANISM: Artificial Sequence
<220> FEATURE:
<223> OTHER INFORMATION: Synthetic construct

<400> SEQUENCE: 44

Lys Leu Thr Gly Gly Thr
1               5

<210> SEQ ID NO 45
<211> LENGTH: 196
<212> TYPE: PRT
<213> ORGANISM: Severe acute respiratory syndrome coronavirus 2

<400> SEQUENCE: 45

Thr Asn Leu Cys Pro Phe Gly Glu Val Phe Asn Ala Thr Arg Phe Ala
1               5                   10                  15

Ser Val Tyr Ala Trp Asn Arg Lys Arg Ile Ser Asn Cys Val Ala Asp
            20                  25                  30

Tyr Ser Val Leu Tyr Asn Ser Ala Ser Phe Ser Thr Phe Lys Cys Tyr
        35                  40                  45

Gly Val Ser Pro Thr Lys Leu Asn Asp Leu Cys Phe Thr Asn Val Tyr
    50                  55                  60

Ala Asp Ser Phe Val Ile Arg Gly Asp Glu Val Arg Gln Ile Ala Pro
65                  70                  75                  80

Gly Gln Thr Gly Lys Ile Ala Asp Tyr Asn Tyr Lys Leu Pro Asp Asp
                85                  90                  95

Phe Thr Gly Cys Val Ile Ala Trp Asn Ser Asn Asn Leu Asp Ser Lys
            100                 105                 110

Val Gly Gly Asn Tyr Asn Tyr Leu Tyr Arg Leu Phe Arg Lys Ser Asn
        115                 120                 125

Leu Lys Pro Phe Glu Arg Asp Ile Ser Thr Glu Ile Tyr Gln Ala Gly
130                 135                 140

Ser Thr Pro Cys Asn Gly Val Glu Gly Phe Asn Cys Tyr Phe Pro Leu
145                 150                 155                 160

Gln Ser Tyr Gly Phe Gln Pro Thr Asn Gly Val Gly Tyr Gln Pro Tyr
                165                 170                 175

Arg Val Val Val Leu Ser Phe Glu Leu Leu His Ala Pro Ala Thr Val
            180                 185                 190

Cys Gly Pro Lys
        195

<210> SEQ ID NO 46
<211> LENGTH: 4
<212> TYPE: PRT
<213> ORGANISM: Artificial Sequence
<220> FEATURE:
<223> OTHER INFORMATION: Synthetic construct

<400> SEQUENCE: 46
```

Gly Pro Gly Met
1

<210> SEQ ID NO 47
<211> LENGTH: 72
<212> TYPE: PRT
<213> ORGANISM: Severe acute respiratory syndrome coronavirus 2

<400> SEQUENCE: 47

Asn Ser Asn Asn Leu Asp Ser Lys Val Gly Asn Tyr Asn Tyr Leu
1               5                   10                  15

Tyr Arg Leu Phe Arg Lys Ser Asn Leu Lys Pro Phe Glu Arg Asp Ile
                20                  25                  30

Ser Thr Glu Ile Tyr Gln Ala Gly Ser Thr Pro Cys Asn Gly Val Glu
            35                  40                  45

Gly Phe Asn Cys Tyr Phe Pro Leu Gln Ser Tyr Gly Phe Gln Pro Thr
        50                  55                  60

Asn Gly Val Gly Tyr Gln Pro Tyr
65                  70

<210> SEQ ID NO 48
<211> LENGTH: 210
<212> TYPE: PRT
<213> ORGANISM: Artificial Sequence
<220> FEATURE:
<223> OTHER INFORMATION: Synthetic construct

<400> SEQUENCE: 48

Thr Gly Gly Thr Thr Asn Leu Cys Pro Phe Gly Glu Val Phe Asn Ala
1               5                   10                  15

Thr Arg Phe Ala Ser Val Tyr Ala Trp Asn Arg Lys Arg Ile Ser Asn
                20                  25                  30

Cys Val Ala Asp Tyr Ser Val Leu Tyr Asn Ser Ala Ser Phe Ser Thr
            35                  40                  45

Phe Lys Cys Tyr Gly Val Ser Pro Thr Lys Leu Asn Asp Leu Cys Phe
        50                  55                  60

Thr Asn Val Tyr Ala Asp Ser Phe Val Ile Arg Gly Asp Glu Val Arg
65                  70                  75                  80

Gln Ile Ala Pro Gly Gln Thr Gly Lys Ile Ala Asp Tyr Asn Tyr Lys
                85                  90                  95

Leu Pro Asp Asp Phe Thr Gly Cys Val Ile Ala Trp Asn Ser Asn Asn
            100                 105                 110

Leu Asp Ser Lys Val Gly Gly Asn Tyr Asn Tyr Leu Tyr Arg Leu Phe
        115                 120                 125

Arg Lys Ser Asn Leu Lys Pro Phe Glu Arg Asp Ile Ser Thr Glu Ile
130                 135                 140

Tyr Gln Ala Gly Ser Thr Pro Cys Asn Gly Val Glu Gly Phe Asn Cys
145                 150                 155                 160

Tyr Phe Pro Leu Gln Ser Tyr Gly Phe Gln Pro Thr Asn Gly Val Gly
                165                 170                 175

Tyr Gln Pro Tyr Arg Val Val Val Leu Ser Phe Glu Leu Leu His Ala
            180                 185                 190

Pro Ala Thr Val Cys Gly Pro Lys Gly Pro Gly Met His His His His
        195                 200                 205

His His
    210

<210> SEQ ID NO 49
<211> LENGTH: 7254
<212> TYPE: DNA
<213> ORGANISM: Artificial Sequence
<220> FEATURE:
<223> OTHER INFORMATION: Synthetic construct

<400> SEQUENCE: 49

| | | | | | |
|---|---|---|---|---|---|
| gaattcgcca | ccatgggaat | acttccttcc | cctggtatgc | ctgcgcttct | ttcactcgtg | 60 |
| tcccttctta | gcgtacttct | catgggctgc | gtcgccgaaa | agcttaccgg | tggtaccaca | 120 |
| aatctctgcc | catttgggga | agttttcaat | gcgacaagat | tcgctagtgt | ctacgcatgg | 180 |
| aaccggaaac | gaatcagcaa | ctgcgtagcg | gattactccg | tcttgtataa | ttccgcgtca | 240 |
| ttctctacgt | tcaagtgcta | tggtgtatcc | cccaccaaac | tcaacgactt | gtgctttacg | 300 |
| aatgtctatg | ccgattcatt | cgttatacgc | ggagacgagg | taagacaaat | agctccaggg | 360 |
| cagaccggga | aaattgcgga | ttataactac | aaactgccag | acgactttac | tgggtgtgtt | 420 |
| atcgcctgga | acagtaacaa | tttggactcc | aaagtcgggg | gtaactataa | ttacttgtat | 480 |
| agactgttcc | gcaaaagcaa | tctcaaaccc | ttcgagcggg | atatttccac | cgagatttat | 540 |
| caggcgggga | gtactccatg | caatgggcgtt | gagggattta | actgctattt | tccattgcaa | 600 |
| tcttacggtt | tccagcctac | gaatggagtc | ggatatcaac | cctacagggt | cgtcgtgctg | 660 |
| tcatttgaac | tcctgcatgc | ccccgctact | gtctgcgggc | caaggggggcc | cgggatgcat | 720 |
| caccatcatc | accattagct | cgaggctagc | ttgactgact | gagatacagc | gtaccttcag | 780 |
| ctcacagaca | tgataagata | cattgatgag | tttggacaaa | ccacaactag | aatgcagtga | 840 |
| aaaaaatgct | ttatttgtga | aatttgtgat | gctattgctt | tatttgtaac | cattataagc | 900 |
| tgcaataaac | aagttaacaa | caacaattgc | attcatttta | tgtttcaggt | tcaggggggag | 960 |
| gtgtgggagg | ttttttaaag | caagtaaaac | ctctacaaat | gtggtattgg | cccatctcta | 1020 |
| tcggtatcgt | agcataaccc | cttggggcct | ctaaacgggt | cttgaggggt | tttttgtgcc | 1080 |
| cctcgggccg | gattgctatc | taccggcatt | ggcgcagaaa | aaaatgcctg | atgcgacgct | 1140 |
| gcgcgtctta | tactcccaca | tatgccagat | tcagcaacgg | atacggcttc | cccaacttgc | 1200 |
| ccacttccat | acgtgtcctc | cttaccagaa | atttatcctt | aaggtcgtca | gctatcctgc | 1260 |
| aggcgatctc | tcgatttcga | tcaagacatt | cctttaatgg | tcttttctgg | acaccactag | 1320 |
| gggtcagaag | tagttcatca | aactttcttc | cctccctaat | ctcattggtt | accttgggct | 1380 |
| atcgaaactt | aattaaccag | tcaagtcagc | tacttggcga | gatcgacttg | tctgggtttc | 1440 |
| gactacgctc | agaattgcgt | cagtcaagtt | cgatctggtc | cttgctattg | caccctctgg | 1500 |
| gtttcgacta | cgctcagaat | tgcgtcagtc | aagttcgatc | tggtccttgc | tattgcaccc | 1560 |
| aaaaaggccg | cgttgctggc | gttttttccat | aggctccgcc | ccctgacga | gcatcacaaa | 1620 |
| aatcgacgct | caagtcagag | gtggcgaaac | ccgacaggac | tataaagata | ccaggcgttt | 1680 |
| cccccctggaa | gctccctcgt | gcgctctcct | gttccgaccc | tgccgcttac | cggatacctg | 1740 |
| tccgcctttc | tcccttcggg | aagcgtggcg | ctttctcata | gctcacgctg | taggtatctc | 1800 |
| agttcggtgt | aggtcgttcg | ctccaagctg | ggctgtgtgc | acgaaccccc | cgttcagccc | 1860 |
| gaccgctgcg | ccttatccgg | taactctcca | agctgggctg | tgtgcacgaa | ccccccgttc | 1920 |
| agcccgaccg | ctgcgcctta | tccggtaact | attagcagag | cgaggtatgt | aggcggtgct | 1980 |
| acagagttct | tgaagtggtg | gcctaactac | ggctacacta | gaagaacagt | atttggtatc | 2040 |
| tgcgctctgc | tgaagccagt | taccttcgga | aaaagagttg | gtagctcttg | atccggcaaa | 2100 |

```
caaaccaccg ctggtagcgg tggttttttt gtttgcaagc agcagattac gcgcagaaaa    2160
aaaggatctc aagaagatcc tttgatcttt tctacgggt ctgacgctca gtggaacgaa     2220
aactcacgtt aagggatttt ggtcatgaga ttatcaaaaa ggatcttcac ctagatcctt    2280
ttaaattaaa aatgaagttt taaatcaatc taaagtatat atgagtaaac ttggtctgac    2340
agttaccaat gcttaatcag tgaggcacct atctcagcga tctgtctatt tcgttcatcc    2400
atagttgcat ttaaatttcc gaactctcca aggccctcgt cggaaaatct tcaaaccttt    2460
cgtccgatcc atcttgcagg ctacctctcg aacgaactat cgcaagtctc ttggccggcc    2520
ttgcgccttg gctattgctt ggcagcgcct atcgccaggt attactccaa tcccgaatat    2580
ccgagatcgg gatcacccga gagaagttca acctacatcc tcaatcccga tctatccgag    2640
atccgaggaa tatcgaaatc ggggcgcgcc tggcctccgc gccgggtttt ggcgcctccc    2700
gcgggcgccc ccctcgtcac ggcgagcgct gccacgtcag acgaagggcg caggagcgtc    2760
ctgatccttc cgcccggacg ctcaggacag cggcccgctg ctcataagac tcggccttag    2820
aaccccagta tcagcagaag gacattttag gacgggactt gggtgactct agggcactgg    2880 ttttcttttcc agagagcgga acaggcgagg aaaagtagtc ccttctcggc gattctgcgg    2940
agggatctcc gtggggcggt aacgccgat gattatataa ggacgcgccg ggtgtggcac    3000
agctagttcc gtcgcagccg ggatttgggt cgcggttctt gtttgtggat cgctgtgatc    3060
gtcacttggt gagtagcggg ctgctgggct ggccggggct ttcgtggccg ccgggccgct    3120
cggtgggacg gaagcgtgtg gagagaccgc caagggctgt agtctgggtc cgcgagcaag    3180
gttgccctga actgggggtt gggggagcg cagcaaaatg gcggctgttc ccgagtcttg    3240 aatgaagac gcttgtgagg cgggctgtga ggtcgttgaa acaaggtggg gggcatggtg    3300
ggcggcaaga acccaaggtc ttgagccctt cgctaatgcg ggaaagctct tattcgggtg    3360
agatgggctg ggcaccatct ggggaccctg acgtgaagtt tgtcactgac tggagaactc    3420
ggtttgtcgt ctgttgcggg ggcggcagtt atggcggtgc cgttgggcag tgcacccgta    3480
cctttgggag cgcgcgccct cgtcgtgtcg tgacgtcacc cgttctgttg gcttataatg    3540
cagggtgggg ccacctgccg gtaggtgtgc ggtaggcttt tctccgtcgc aggacgcagg    3600
gttcgggcct agggtaggct ctcctgaatc gacaggcgcc ggacctctgg tgagggagg    3660 gataagtgag gcgtcagttt ctttggtcgg ttttatgtac ctatcttctt aagtagctga    3720
agctccggtt ttgaactatg cgctcggggt tggcgagtgt gttttgtgaa gttttttagg    3780
caccttttga aatgtaatca tttgggtcaa tatgtaattt tcagtgttag acttgtaaat    3840
tgtccgctaa attctggccg ttttttggctt ttttgttaga caacatgggt aaaaagcctg    3900
aactcaccgc gacgtctgtc gagaagtttc tgatcgaaaa gttcgacagc gtctccgacc    3960
tgatgcagct ctcggagggc gaagaatctc gtgctttcag cttcgatgta ggagggcgtg    4020
gatatgtcct gcgggtaaat agctgcgccg atggtttcta caaagatcgt tatgtttatc    4080
ggcactttgc atccgccgcg ctcccgattc cggaagtgct tgacattggg gagttcagcg    4140
agagcctgac ctattgcatc tcccgccgtg cacagggtgt cacgttgcaa gacctgcctg    4200
aaaccgaact gcccgctgtt ctgcagccgg tcgcggaggc aatggatgcc atcgctgccg    4260
ccgatcttag ccagacgagc gggttcggcc cattcggacc gcaaggaatc ggtcaataca    4320
ctacatggcg tgatttcata tgcgcgattg ctgatcccca tgtgtatcac tggcaaactg    4380
tgatggacga caccgtcagt gcgtccgtcg cgcaggctct cgatgagctg atgctttggg    4440
```

```
ccgaggactg ccccgaagtc cggcacctcg tgcacgcgga tttcggctcc aacaatgtcc   4500
tgacggacaa tggccgcata acagcggtca ttgactggag cgaggcgatg ttcggggatt   4560
cccaatacga ggtcgccaac atcttcttct ggaggccgtg gttggcttgt atggagcagc   4620
agacgcgcta cttcgagcgg aggcatccgg agcttgcagg atcgcccgg ctccgggcgt    4680 atatgctccg cattggtctt gaccaactct atcagagctt ggttgacggc aatttcgatg   4740
atgcagcttg ggcgcagggt cgatgcgacg caatcgtccg atccggagcc gggactgtcg   4800
ggcgtacaca aatcgcccgc agaagcgccg ccgtctggac cgatggctgt gtagaagtac   4860
tcgccgatag tggaaaccga cgccccagca ctcgtccgag ggcaaaggaa taagctagta   4920
tgtaagccta gtcttagata ataaaatcgc tatccatcga agatggatgt gtgttggttt   4980
tttgtgtgtg taacgctagg cgcgcctggt gtaccgagaa cgatcctctc agtgcgagtc   5040
tcgacgatcc atatcgttgc ttggcagtca gccagtcgga atccagcttg ggacccagga   5100
agtccaatcg tcagatattg tactcaagcc tggtcacggc agcgtaccga tctgtttaaa   5160
cctagatatt gatagtctga tcggtcaacg tataatcgag tcctagcttt tgcaaacatc   5220
tatcaagaga caggatcagc aggaggcttt cgcatgagta ttcaacattt ccgtgtcgcc   5280
cttattccct ttttgcggc attttgcctt cctgttttg ctcacccaga aacgctggtg     5340
aaagtaaaag atgctgaaga tcagttgggt gcgcgagtgg gttacatcga actggatctc   5400
aacagcggta agatccttga gagttttcgc cccgaagaac gctttccaat gatgagcact   5460
tttaaagttc tgctatgtgg cgcggtatta tcccgtattg acgccgggca agagcaactc   5520
ggtcgccgca tacactattc tcagaatgac ttggttgagt attcaccagt cacagaaaag   5580
catcttacgg atggcatgac agtaagagaa ttatgcagtg ctgccataac catgagtgat   5640
aacactgcgg ccaacttact tctgacaacg attggaggac cgaaggagct aaccgctttt   5700
ttgcacaaca tgggggatca tgtaactcgc cttgatcgtt gggaaccgga gctgaatgaa   5760
gccataccaa acgacgagcg tgacaccacg atgcctgtag caatggcaac aaccttgcgt   5820
aaactattaa ctggcgaact acttactcta gcttcccggc aacagttgat agactggatg   5880
gaggcggata aagttgcagg accacttctg cgctcggccc ttccggctgg ctggtttatt   5940
gctgataaat ctggagccgg tgagcgtggg tctcgcggta tcattgcagc actggggcca   6000
gatggtaagc cctcccgtat cgtagttatc tacacgacgg ggagtcaggc aactatggat   6060
gaacgaaata gacagatcgc tgagataggt gcctcactga ttaagcattg gtaaccgatt   6120
ctaggtgcat tggcgcagaa aaaaatgcct gatgcgacgc tgcgcgtctt atactcccac   6180
atatgccaga ttcagcaacg gatacggctt ccccaacttg cccacttcca tacgtgtcct   6240
ccttaccaga aatttatcct taagatcgtt taaactcgac tctggctcta tcgaatctcc   6300
gtcgtttcga gcttacgcga acagccgtgg cgctcatttg ctcgtcgggc atcgaatctc   6360
gtcagctatc gtcagcttac cttttttggca gcgatcgcgg ctcccgacat cttgaccat   6420 tagctccaca ggtatcttct tccctctagt ggtcataaca gcagcttcag ctacctctca   6480
attcaaaaaa cccctcaaga cccgtttaga ggccccaagg ggttatgcta tcaatcgttg   6540
cgttacacac acaaaaaacc aacacacatc catcttcgat ggatagcgat tttattatct   6600
aactgctgat cgagtgtagc cagatctagt aatcaattac ggggtcatta gttcatagcc   6660
catatatgga gttccgcgtt acataactta cggtaaatgg cccgcctggc tgaccgccca   6720
acgacccccg cccattgacg tcaataatga cgtatgttcc catagtaacg ccaatagtga   6780 cttttccattg acgtcaatgg gtggagtatt tacggtaaac tgcccacttg gcagtacatc   6840
```

```
aagtgtatca tatgccaagt acgcccccta ttgacgtcaa tgacggtaaa tggcccgcct    6900
ggcattatgc ccagtacatg acctttatggg actttcctac ttggcagtac atctacgtat    6960
tagtcatcgc tattaccatg ctgatgcggt tttggcagta catcaatggg cgtggatagc    7020
ggtttgactc acggggattt ccaagtctcc accccattga cgtcaatggg agtttgtttt    7080
ggcaccaaaa tcaacgggac tttccaaaat gtcgtaacaa ctccgcccca ttgacgcaaa    7140
tgggcggtag gcgtgtacgg tgggaggtct atataagcag agctggttta gtgaaccgtc    7200
agatcagatc tttgtcgatc ctaccatcca ctcgacacac ccgccagcgg ccgc          7254
```

<210> SEQ ID NO 50
<211> LENGTH: 143
<212> TYPE: PRT
<213> ORGANISM: Artificial Sequence
<220> FEATURE:
<223> OTHER INFORMATION: Synthetic construct

<400> SEQUENCE: 50

```
Met Arg Arg Cys Ala Ser Tyr Thr Pro Thr Tyr Ala Arg Phe Ser Asn
1               5                   10                  15

Gly Tyr Gly Phe Pro Asn Leu Pro Thr Ser Ile Arg Val Leu Leu Thr
            20                  25                  30

Arg Asn Leu Ser Leu Arg Ser Ser Ala Ile Leu Gln Ala Ile Ser Arg
        35                  40                  45

Phe Arg Ser Arg His Ser Phe Asn Gly Leu Phe Trp Thr Pro Leu Gly
    50                  55                  60

Val Arg Ser Ser Ser Asn Phe Leu Pro Ser Leu Ile Ser Leu Val
65                  70                  75                  80

Thr Leu Gly Tyr Arg Asn Leu Ile Asn Gln Ser Ser Gln Leu Leu Gly
                85                  90                  95

Glu Ile Asp Leu Ser Gly Phe Arg Leu Arg Ser Glu Leu Arg Gln Ser
            100                 105                 110

Ser Ser Ile Trp Ser Leu Leu Leu His Pro Phe Ser Asp Tyr Glu Phe
        115                 120                 125

His Leu Asn His Val Ser Lys Arg Pro Ala Lys Gly Gln Glu Pro
    130                 135                 140
```

<210> SEQ ID NO 51
<211> LENGTH: 169
<212> TYPE: PRT
<213> ORGANISM: Artificial Sequence
<220> FEATURE:
<223> OTHER INFORMATION: Synthetic construct

<400> SEQUENCE: 51

```
Met Val Pro Ser Pro Ser His Pro Asn Lys Ser Phe Pro Ala Leu Ala
1               5                   10                  15

Lys Gly Ser Arg Pro Trp Val Leu Ala Ala His His Ala Pro His Leu
            20                  25                  30

Val Ser Thr Thr Ser Gln Pro Ala Gln Ala Ser Ser Ile Gln Asp
        35                  40                  45

Ser Gly Thr Ala Ala Ile Leu Leu Arg Ser Pro Gln Pro Pro Val Gln
    50                  55                  60

Gly Asn Leu Ala Arg Gly Pro Arg Leu Gln Leu Ala Val Ser Pro
65                  70                  75                  80

His Ala Ser Val Pro Pro Ser Gly Pro Ala Ala Thr Lys Ala Pro Ala
                85                  90                  95
```

```
Ser Pro Ala Ala Arg Tyr Ser Pro Ser Asp Asp His Ser Asp Pro Gln
            100                 105                 110

Thr Arg Thr Ala Thr Gln Ile Pro Ala Ala Thr Glu Leu Ala Val Pro
        115                 120                 125

His Pro Ala Arg Pro Tyr Ile Ile Ile Gly Val His Arg Pro Thr Glu
    130                 135                 140

Ile Pro Pro Gln Asn Arg Arg Glu Gly Thr Thr Phe Pro Arg Leu Phe
145                 150                 155                 160

Arg Ser Leu Glu Arg Lys Pro Val Pro
                165

<210> SEQ ID NO 52
<211> LENGTH: 97
<212> TYPE: PRT
<213> ORGANISM: Artificial Sequence
<220> FEATURE:
<223> OTHER INFORMATION: Synthetic construct

<400> SEQUENCE: 52

Met Pro Pro Thr Leu Phe Gln Arg Pro His Ser Pro His Lys Arg
1               5                   10                  15

Leu Pro Phe Lys Thr Arg Glu Gln Pro Pro Phe Cys Cys Ala Pro Pro
                20                  25                  30

Asn Pro Gln Phe Arg Ala Thr Leu Leu Ala Asp Pro Asp Tyr Ser Pro
            35                  40                  45

Trp Arg Ser Leu His Thr Leu Pro Ser His Arg Ala Ala Arg Arg Pro
        50                  55                  60

Arg Lys Pro Arg Pro Ala Gln Gln Pro Ala Thr His Gln Val Thr Ile
65                  70                  75                  80

Thr Ala Ile His Lys Gln Glu Pro Arg Pro Lys Ser Arg Leu Arg Arg
                85                  90                  95

Asn

<210> SEQ ID NO 53
<211> LENGTH: 79
<212> TYPE: PRT
<213> ORGANISM: Artificial Sequence
<220> FEATURE:
<223> OTHER INFORMATION: Synthetic construct

<400> SEQUENCE: 53

Met Arg Glu Ser Ser Tyr Ser Gly Glu Met Gly Trp Ala Pro Ser Gly
1               5                   10                  15

Asp Pro Asp Val Lys Phe Val Thr Asp Trp Arg Thr Arg Phe Val Val
                20                  25                  30

Cys Cys Gly Gly Gly Ser Tyr Gly Ala Val Gly Gln Cys Thr Arg
            35                  40                  45

Thr Phe Gly Ser Ala Arg Pro Arg Arg Val Val Thr Ser Pro Val Leu
        50                  55                  60

Leu Ala Tyr Asn Ala Gly Trp Gly His Leu Pro Val Gly Val Arg
65                  70                  75

<210> SEQ ID NO 54
<211> LENGTH: 342
<212> TYPE: PRT
<213> ORGANISM: Artificial Sequence
<220> FEATURE:
<223> OTHER INFORMATION: Synthetic construct
```

<400> SEQUENCE: 54

```
Met Gly Lys Lys Pro Glu Leu Thr Ala Thr Ser Val Glu Lys Phe Leu
1               5                   10                  15

Ile Glu Lys Phe Asp Ser Val Ser Asp Leu Met Gln Leu Ser Glu Gly
            20                  25                  30

Glu Glu Ser Arg Ala Phe Ser Phe Asp Val Gly Gly Arg Gly Tyr Val
        35                  40                  45

Leu Arg Val Asn Ser Cys Ala Asp Gly Phe Tyr Lys Asp Arg Tyr Val
    50                  55                  60

Tyr Arg His Phe Ala Ser Ala Ala Leu Pro Ile Pro Glu Val Leu Asp
65                  70                  75                  80

Ile Gly Glu Phe Ser Glu Ser Leu Thr Tyr Cys Ile Ser Arg Arg Ala
            85                  90                  95

Gln Gly Val Thr Leu Gln Asp Leu Pro Glu Thr Glu Leu Pro Ala Val
        100                 105                 110

Leu Gln Pro Val Ala Glu Ala Met Asp Ala Ile Ala Ala Ala Asp Leu
    115                 120                 125

Ser Gln Thr Ser Gly Phe Gly Pro Phe Gly Pro Gln Gly Ile Gly Gln
130                 135                 140

Tyr Thr Thr Trp Arg Asp Phe Ile Cys Ala Ile Ala Asp Pro His Val
145                 150                 155                 160

Tyr His Trp Gln Thr Val Met Asp Asp Thr Val Ser Ala Ser Val Ala
            165                 170                 175

Gln Ala Leu Asp Glu Leu Met Leu Trp Ala Glu Asp Cys Pro Glu Val
        180                 185                 190

Arg His Leu Val His Ala Asp Phe Gly Ser Asn Asn Val Leu Thr Asp
    195                 200                 205

Asn Gly Arg Ile Thr Ala Val Ile Asp Trp Ser Glu Ala Met Phe Gly
210                 215                 220

Asp Ser Gln Tyr Glu Val Ala Asn Ile Phe Phe Trp Arg Pro Trp Leu
225                 230                 235                 240

Ala Cys Met Glu Gln Gln Thr Arg Tyr Phe Glu Arg Arg His Pro Glu
            245                 250                 255

Leu Ala Gly Ser Pro Arg Leu Arg Ala Tyr Met Leu Arg Ile Gly Leu
        260                 265                 270

Asp Gln Leu Tyr Gln Ser Leu Val Asp Gly Asn Phe Asp Asp Ala Ala
    275                 280                 285

Trp Ala Gln Gly Arg Cys Asp Ala Ile Val Arg Ser Gly Ala Gly Thr
290                 295                 300

Val Gly Arg Thr Gln Ile Ala Arg Arg Ser Ala Ala Val Trp Thr Asp
305                 310                 315                 320

Gly Cys Val Glu Val Leu Ala Asp Ser Gly Asn Arg Arg Pro Ser Thr
            325                 330                 335

Arg Pro Arg Ala Lys Glu
        340
```

<210> SEQ ID NO 55
<211> LENGTH: 256
<212> TYPE: PRT
<213> ORGANISM: Artificial Sequence
<220> FEATURE:
<223> OTHER INFORMATION: Synthetic construct

<400> SEQUENCE: 55

Met Pro Pro Leu Glu Val Ala Arg Leu Leu Leu His Thr Ser Gln Pro

```
            1               5                   10                  15
        Arg Pro Pro Glu Glu Asp Val Gly Asp Leu Val Leu Gly Ile Pro Glu
                        20                  25                  30
        His Arg Leu Ala Pro Val Asn Asp Arg Cys Tyr Ala Ala Ile Val Arg
                        35                  40                  45
        Gln Asp Ile Val Gly Ala Glu Ile Arg Val His Glu Val Pro Asp Phe
                50                      55                  60
        Gly Ala Val Leu Gly Pro Lys His Gln Leu Ile Glu Ser Leu Arg Asp
        65                      70                  75                  80
        Gly Arg Thr Asp Gly Val Val His His Ser Leu Pro Val Ile His Met
                            85                  90                  95
        Gly Ile Ser Asn Arg Ala Tyr Glu Ile Thr Pro Cys Ser Val Leu Thr
                        100                 105                 110
        Asp Ser Leu Arg Ser Glu Trp Ala Glu Pro Ala Arg Leu Ala Lys Ile
                    115                 120                 125
        Gly Gly Ser Asp Gly Ile His Cys Leu Arg Asp Arg Leu Gln Asn Ser
                130                 135                 140
        Gly Gln Phe Gly Phe Arg Gln Val Leu Gln Arg Asp Thr Leu Cys Thr
        145                 150                 155                 160
        Ala Gly Asp Ala Ile Gly Gln Ala Leu Ala Glu Leu Pro Asn Val Lys
                            165                 170                 175
        His Phe Arg Asn Arg Glu Arg Gly Gly Cys Lys Val Pro Ile Asn Ile
                        180                 185                 190
        Thr Ile Phe Val Glu Thr Ile Gly Ala Ala Ile Tyr Pro Gln Asp Ile
                    195                 200                 205
        Ser Thr Pro Ser Tyr Ile Glu Ala Glu Ser Thr Arg Phe Phe Ala Leu
                210                 215                 220
        Arg Glu Leu His Gln Val Gly Asp Ala Val Gly Leu Phe Asp Gln Lys
        225                 230                 235                 240
        Leu Leu Asp Arg Arg Gly Glu Phe Arg Leu Phe Thr His Val Val
                            245                 250                 255

<210> SEQ ID NO 56
<211> LENGTH: 286
<212> TYPE: PRT
<213> ORGANISM: Artificial Sequence
<220> FEATURE:
<223> OTHER INFORMATION: Synthetic construct

<400> SEQUENCE: 56

Met Ser Ile Gln His Phe Arg Val Ala Leu Ile Pro Phe Phe Ala Ala
        1               5                   10                  15
        Phe Cys Leu Pro Val Phe Ala His Pro Glu Thr Leu Val Lys Val Lys
                        20                  25                  30
        Asp Ala Glu Asp Gln Leu Gly Ala Arg Val Gly Tyr Ile Glu Leu Asp
                        35                  40                  45
        Leu Asn Ser Gly Lys Ile Leu Glu Ser Phe Arg Pro Glu Glu Arg Phe
                    50                  55                  60
        Pro Met Met Ser Thr Phe Lys Val Leu Leu Cys Gly Ala Val Leu Ser
        65                      70                  75                  80
        Arg Ile Asp Ala Gly Gln Glu Gln Leu Gly Arg Arg Ile His Tyr Ser
                            85                  90                  95
        Gln Asn Asp Leu Val Glu Tyr Ser Pro Val Thr Glu Lys His Leu Thr
                        100                 105                 110
        Asp Gly Met Thr Val Arg Glu Leu Cys Ser Ala Ala Ile Thr Met Ser
```

```
                115                 120                 125
Asp Asn Thr Ala Ala Asn Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285

<210> SEQ ID NO 57
<211> LENGTH: 88
<212> TYPE: PRT
<213> ORGANISM: Artificial Sequence
<220> FEATURE:
<223> OTHER INFORMATION: Synthetic construct

<400> SEQUENCE: 57

Met Ile Pro Arg Asp Pro Arg Ser Pro Ala Pro Asp Leu Ser Ala Ile
1               5                   10                  15

Asn Gln Pro Ala Gly Arg Ala Glu Arg Arg Ser Gly Pro Ala Thr Leu
            20                  25                  30

Ser Ala Ser Ile Gln Ser Ile Asn Cys Cys Arg Glu Ala Arg Val Ser
        35                  40                  45

Ser Ser Pro Val Asn Ser Leu Arg Lys Val Val Ala Ile Ala Thr Gly
    50                  55                  60

Ile Val Val Ser Arg Ser Ser Phe Gly Met Ala Ser Phe Ser Ser Gly
65                  70                  75                  80

Ser Gln Arg Ser Arg Arg Val Thr
                85

<210> SEQ ID NO 58
<211> LENGTH: 144
<212> TYPE: PRT
<213> ORGANISM: Artificial Sequence
<220> FEATURE:
<223> OTHER INFORMATION: Synthetic construct

<400> SEQUENCE: 58

Met Arg Arg Cys Ala Ser Tyr Thr Pro Thr Tyr Ala Arg Phe Ser Asn
1               5                   10                  15

Gly Tyr Gly Phe Pro Asn Leu Pro Thr Ser Ile Arg Val Leu Leu Thr
            20                  25                  30

Arg Asn Leu Ser Leu Arg Ser Phe Lys Leu Asp Ser Gly Ser Ile Glu
        35                  40                  45
```

Ser Pro Ser Phe Arg Ala Tyr Ala Asn Ser Arg Gly Ala His Leu Leu
    50                  55                  60

Val Gly His Arg Ile Ser Ser Ala Ile Val Ser Leu Pro Phe Trp Gln
65                  70                  75                  80

Arg Ser Arg Leu Pro Thr Ser Trp Thr Ile Ser Ser Thr Gly Ile Phe
                85                  90                  95

Phe Pro Leu Val Val Ile Thr Ala Ala Ser Ala Thr Ser Gln Phe Lys
                100                 105                 110

Lys Pro Leu Lys Thr Arg Leu Glu Ala Pro Arg Gly Tyr Ala Ile Asn
            115                 120                 125

Arg Cys Val Thr His Thr Lys Asn Gln His Thr Ser Ile Phe Asp Gly
        130                 135                 140

<210> SEQ ID NO 59
<211> LENGTH: 723
<212> TYPE: DNA
<213> ORGANISM: Artificial Sequence
<220> FEATURE:
<223> OTHER INFORMATION: Synthetic construct

<400> SEQUENCE: 59

| | | | | | | |
|---|---|---|---|---|---|---|
| atgggaatac | ttccttcccc | tggtatgcct | gcgcttcttt | cactcgtgtc | ccttcttagc | 60 |
| gtacttctca | tgggctgcgt | cgccgaaaag | cttaccggtg | gtaccacaaa | tctctgccca | 120 |
| tttggggaag | ttttcaatgc | gacaagattc | gctagtgtct | acgcatggaa | ccggaaacga | 180 |
| atcagcaact | gcgtagcgga | ttactccgtc | ttgtataatt | ccgcgtcatt | ctctacgttc | 240 |
| aagtgctatg | tgtatccccc | accaaaactc | aacgactgt | gctttacgaa | tgtctatgcc | 300 |
| gattcattcg | ttatacgcgg | agacgaggta | agacaaatag | ctccagggca | gaccgggaaa | 360 |
| attgcggatt | ataactacaa | actgccagac | gactttactg | ggtgtgttat | cgcctggaac | 420 |
| agtaacaatt | tggactccaa | agtcgggggt | aactataatt | acttgtatag | actgttccgc | 480 |
| aaaagcaatc | tcaaacccttt | cgagcggat | atttccaccg | agatttatca | ggcggggagt | 540 |
| actccatgca | atggggttga | gggatttaac | tgctattttc | cattgcaatc | ttacggtttc | 600 |
| cagcctacga | atggagtcgg | atatcaaccc | tacagggtcg | tcgtgctgtc | atttgaactc | 660 |
| ctgcatgccc | ccgctactgt | ctgcgggcca | aaggggcccg | ggatgcatca | ccatcatcac | 720 |
| cat | | | | | | 723 |

<210> SEQ ID NO 60
<211> LENGTH: 636
<212> TYPE: DNA
<213> ORGANISM: Artificial Sequence
<220> FEATURE:
<223> OTHER INFORMATION: Synthetic construct

<400> SEQUENCE: 60

| | | | | | | |
|---|---|---|---|---|---|---|
| aagcttaccg | gtggtaccac | aaatctctgc | ccatttgggg | aagttttcaa | tgcgacaaga | 60 |
| ttcgctagtg | tctacgcatg | gaaccggaaa | cgaatcagca | actgcgtagc | ggattactcc | 120 |
| gtcttgtata | attccgcgtc | attctctacg | ttcaagtgct | atggtgtatc | ccccaccaaa | 180 |
| ctcaacgact | gtgctttac | gaatgtctat | gccgattcat | tcgttatacg | cggagacgag | 240 |
| gtaagacaaa | tagctccagg | gcagaccggg | aaaattgcgg | attataacta | caaactgcca | 300 |
| gacgacttta | ctgggtgtgt | tatcgcctgg | aacagtaaca | atttggactc | caaagtcggg | 360 |
| ggtaactata | attacttgta | tagactgttc | cgcaaaagca | atctcaaacc | cttcgagcgg | 420 |
| gatatttcca | ccgagattta | tcaggcgggg | agtactccat | gcaatggggt | tgagggattt | 480 |

```
aactgctatt ttccattgca atcttacggt ttccagccta cgaatggagt cggatatcaa      540
ccctacaggg tcgtcgtgct gtcatttgaa ctcctgcatg ccccgctac tgtctgcggg       600 ccaaagggc ccgggatgca tcaccatcat caccat                                 636

<210> SEQ ID NO 61
<211> LENGTH: 588
<212> TYPE: DNA
<213> ORGANISM: Severe acute respiratory syndrome coronavirus 2

<400> SEQUENCE: 61
acaaatctct gcccatttgg ggaagttttc aatgcgacaa gattcgctag tgtctacgca       60
tggaaccgga aacgaatcag caactgcgta gcggattact ccgtcttgta taattccgcg      120
tcattctcta cgttcaagtg ctatggtgta tcccccacca aactcaacga cttgtgcttt     180
acgaatgtct atgccgattc attcgttata cgcggagacg aggtaagaca aatagctcca     240
gggcagaccg ggaaaattgc ggattataac tacaaactgc cagacgactt tactgggtgt    300
gttatcgcct ggaacagtaa caatttggac tccaaagtcg ggggtaacta taattacttg    360
tatagactgt tccgcaaaag caatctcaaa cccttcgagc gggatatttc caccgagatt    420
tatcaggcgg ggagtactcc atgcaatggg gttgagggat ttaactgcta ttttccattg    480
caatcttacg gtttccagcc tacgaatgga gtcggatatc aaccctacag ggtcgtcgtg   540
ctgtcatttg aactcctgca tgccccgct actgtctgcg ggccaaag                   588

<210> SEQ ID NO 62
<211> LENGTH: 207
<212> TYPE: DNA
<213> ORGANISM: Severe acute respiratory syndrome coronavirus 2

<400> SEQUENCE: 62
agtaacaatt tggactccaa agtcgggggt aactataatt acttgtatag actgttccgc       60
aaaagcaatc tcaaaccctt cgagcgggat atttccaccg agatttatca ggcggggagt     120
actccatgca atggggttga gggatttaac tgctattttc cattgcaatc ttacggtttc     180
cagcctacga atggagtcgg atatcaa                                          207
```

What is claimed is:

1. An immunogenic composition comprising:
   a fragment of the Severe acute respiratory syndrome coronavirus 2 (SARS-CoV-2) spike protein, wherein the fragment is the receptor-binding domain (RBD) as set forth in SEQ ID NO: 45, and wherein the RBD is N-glycosylated;
   an adjuvant; and
   a carrier.

2. The composition of claim 1, wherein the immunogenic composition induces neutralizing antibodies against SARS-CoV-2.

3. An immunogenic composition comprising:
   a polypeptide comprising the amino acid sequence as set forth in SEQ ID NO: 3, wherein the polypeptide is N-glycosylated;
   an adjuvant; and
   a carrier.

4. The composition of claim 1, wherein said fragment comprises SEQ ID NO: 4.

5. The composition of claim 1, wherein said fragment comprises one or more amino acid substitutions so that said fragment is not naturally occurring.

6. A method of preventing or delaying the onset of Coronavirus Disease 2019 (COVID-19) or of reducing at least one symptom of COVID-19 in a subject, comprising the step of providing an effective amount of the composition of claim 1 to the subject.

7. The method of claim 6, wherein the composition is provided to the subject once.

8. The method of claim 6, wherein the composition is provided to the subject more than once.

9. The method of claim 6, wherein the composition is provided subsequently to the subject within weeks, months, or years of the first providing step.

10. The method of claim 6, wherein the subject displays one or more symptoms of COVID-19.

11. The method of claim 6, wherein the subject lacks any symptoms of COVID-19.

12. The method of claim 6, wherein the subject has been exposed to COVID-19.

13. The method of claim 6, wherein the subject has come into contact with a subject that has COVID-19.

14. The method of claim 6, wherein the subject is a child, an elderly person, exposed to a bioweapon or at risk thereof, is a member of the military, or is a health care worker.

* * * * *